US012215314B2

(12) United States Patent
Wang et al.

(10) Patent No.: US 12,215,314 B2
(45) Date of Patent: Feb. 4, 2025

(54) INTEGRATIVE DNA AND RNA LIBRARY PREPARATIONS AND USES THEREOF

(71) Applicants: Yexun Wang, Ellicott City, MD (US); Quan Peng, Clarksburg, MD (US); Daniel Kim, Brunswick, MD (US); QIAGEN Sciences, LLC, Germantown, MD (US)

(72) Inventors: Yexun Wang, Ellicott City, MD (US); Quan Peng, Clarksburg, MD (US); Daniel Kim, Brunswick, MD (US)

(73) Assignee: QIAGEN Sciences, LLC, Germantown, MD (US)

( * ) Notice: Subject to any disclaimer, the term of this patent is extended or adjusted under 35 U.S.C. 154(b) by 239 days.

(21) Appl. No.: 17/041,724

(22) PCT Filed: Mar. 26, 2019

(86) PCT No.: PCT/US2019/024107
§ 371 (c)(1),
(2) Date: Sep. 25, 2020

(87) PCT Pub. No.: WO2019/191122
PCT Pub. Date: Oct. 3, 2019

(65) Prior Publication Data
US 2021/0024920 A1  Jan. 28, 2021

Related U.S. Application Data

(60) Provisional application No. 62/648,174, filed on Mar. 26, 2018.

(51) Int. Cl.
*C12N 15/10* (2006.01)
*C12Q 1/6806* (2018.01)

(52) U.S. Cl.
CPC ....... *C12N 15/1065* (2013.01); *C12Q 1/6806* (2013.01)

(58) Field of Classification Search
CPC .................. C12N 15/1065; C12Q 1/6806
(Continued)

(56) References Cited

U.S. PATENT DOCUMENTS 4,683,195 A  7/1987 Mullis et al.
4,683,202 A  7/1987 Mullis
(Continued)

FOREIGN PATENT DOCUMENTS

WO    2005082098 A2    9/2005
WO    2006073504 A2    7/2006
(Continued)

OTHER PUBLICATIONS

Blanco et al., "Highly Efficient DNA Synthesis by the Phage o29 DNA Polymerase," The Journal of Biological Chemistry, 1989, vol. 264(15), pp. 8935-8940, American Society for Biochemistry and Molecular Biology Publications, Bethesda, Maryland.
(Continued)

*Primary Examiner* — Aaron A Priest
*Assistant Examiner* — Randi Lynn Beil
(74) *Attorney, Agent, or Firm* — Potomac Law Group, PLLC; Judith U. Kim

(57) ABSTRACT

The invention relates to integrated DNA and RNA library preparations and methods of making and uses thereof, wherein the DNA molecules are labelled with a tag identifying the molecule as being a DNA molecule and the RNA molecules are labelled with a tag identifying the molecule as being a RNA molecule. The methods do not require physical separation of DNA and RNA. The methods output two separate libraries from DNA and RNA, respectively, which helps flexible manipulation on downstream sequencing plat- (Continued)

Figure 1:
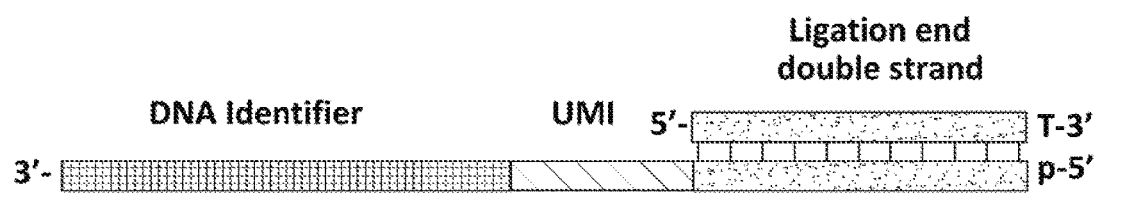
Figure 1:
Figure 1:

forms. The application also claims the DNA library and the cDNA library produced by the method and the DNA tag and the RNA tag used in the method.

16 Claims, 2 Drawing Sheets

Specification includes a Sequence Listing.

(58) Field of Classification Search
USPC .............................................................. 506/4
See application file for complete search history.

(56) References Cited

U.S. PATENT DOCUMENTS

| | | | |
|---|---|---|---|
| 4,965,188 A | 10/1990 | Mullis et al. | |
| 6,432,360 B1 | 8/2002 | Church | |
| 6,485,944 B1 | 11/2002 | Church et al. | |
| 6,511,803 B1 | 1/2003 | Church et al. | |
| 7,425,431 B2 | 9/2008 | Church et al. | |
| 2008/0269068 A1 | 10/2008 | Church et al. | |
| 2009/0018024 A1 | 1/2009 | Church et al. | |
| 2010/0129874 A1 | 5/2010 | Mitra et al. | |
| 2018/0002749 A1* | 1/2018 | Larson | C12Q 1/6869 |
| 2018/0080021 A1* | 3/2018 | Reuter | C12N 15/1065 |

FOREIGN PATENT DOCUMENTS

| | | | | |
|---|---|---|---|---|
| WO | 2014164486 A1 | 10/2014 | | |
| WO | 2014201273 A1 | 12/2014 | | |
| WO | 2018005811 A1 | 1/2018 | | |
| WO | WO-2018057820 A1 * | 3/2018 | ............. | A61K 48/00 |
| WO | 2018126278 A2 | 7/2018 | | |

OTHER PUBLICATIONS

Dey et al., "Integrated genome and transcriptome sequencing of the same cell," Nature Biotechnology, 2015, vol. 33, pp. 285-289, Springer Nature, London, United Kingdom.

International Search Report and Written Opinion dated Jul. 2, 2019 for International Application No. PCT/US2019/024107.

Kivioja et al., "Counting absolute numbers of molecules using unique molecular identifiers," Nature Methods, 2012, vol. 9(1), pp. 72-74, Nature Publishing Group, London, United Kingdom.

Kwok, "High-throughput genotyping assay approaches," Pharmacogenomics, 2000, vol. 1(1), pp. 1-5, Ashley Publications Ltd.

Landegren et al., "Reading Bits of Genetic Information: Methods for Single-Nucleotide Polymorphism Analysis," Genome Research, 1998, vol. 8, pp. 769-776, Cold Spring Harbor Laboratory Research, Cold Spring Harbor, New York.

Lizardi et al., "Mutation detection and single-molecule counting using isothermal rolling-circle amplification," Nature Genetics, 1998, vol. 19, pp. 225-232, Springer Nature, London, United Kingdom.

MacAulay et al., "G&T-seq: parallel sequencing of single-cell genomes and transcriptomes," Nature Methods, 2015, vol. 12(6), pp. 519-522 (7 pages), Nature Publishing Group, London, United Kingdom.

Mertes et al., "Combined ultra-low input mRNA and whole-genome sequencing of human embryonic stem cells," BMC Genomics, 2015, vol. 16(925), pp. 1-11, Springer Nature, London, United Kingdom.

Notomi et al., "Loop-mediated isothermal amplification of DNA," Nucleic Acids Research, 2000, vol. 28(12), pp. i-vii, Oxford University Press, Oxford, United Kingdom.

Porreca et al., "Multiplex amplification of large sets of human exons," Nature Methods, 2007, vol. 4(11), pp. 931-936, Nature Publishing Group, London, United Kingdom.

Reuter et al., "Simul-seq: combined DNA and RNA sequencing for whole-genome and transcriptome profiling," Nature Methods, 2016, vol. 13(11), pp. 953-961, Nature Publishing Group, London, United Kingdom.

Shendure, et al., "Accurate Multiplex Polony Sequencing of an Evolved Bacterial Genome," Science, 2005, Vo. 309 (5741), pp. 1728-1732, American Association for the Advancement of Science, Pennsylvania.

Shi, "Enabling large-Scale Pharmacogenetic Studies by High-Throughput Mutation Detection and Genotyping Technologies," Clinical Chemistry, 2001, vol. 47(2), pp. 164-172, Oxford University Press, Oxford, United Kingdom.

Wu et al., "The Ligation Amplification Reaction (LAR)—Amplification of Specific DNA Sequences Using Sequential Rounds of Template-Dependent Ligation," Genomics, 1989, vol. 4(4), pp. 560-569, Elsevier, Amsterdam, Netherlands.

* cited by examiner

DNA tag molecule that can be ligated to 3' end of double strand DNA fragments.

RNA tag molecule that can be used to add a 5' tag to RNA-derived cDNA fragments through reverse transcription.

RNA tag molecule that can be used to add a 3' tag to RNA-derived cDNA through template switching in RT.

1. gDNA and RNA together

2. Enzymatic fragmentation
   - DNA fragment, end polish
   - RNA fragment

3. RNA Polishing
   - DNA no change

4. DNA label by ligation
   - RNA no change

5. RNA label by TS-RT
   - DNA no change

6. Co DNA/RNA target enrichment

7. Library amplification
   - DNA library by DNA label
   - RNA library by RNA label

INTEGRATIVE DNA AND RNA LIBRARY PREPARATIONS AND USES THEREOF

REFERENCE TO SEQUENCE LISTING SUBMITTED ELECTRONICALLY

The content of the electronically submitted sequence listing in ASCII text file (Name: 2495-0002US01 Sequence Listing ST25.txt; Size: 82 KB; and Date of Creation: Sep. 24, 2020) filed with the application is incorporated herein by reference in its entirety.

BACKGROUND OF THE INVENTION

Paired DNA and RNA profiling enables researchers to gain more biological insights regarding the correlation between genotype and phenotype using samples from the same set of cell population.

To fully understand the complex biological systems, researchers are getting more and more interested in multi-omic information, a full view of genomic, transcriptomic and proteomic data and their interactions. As the first step, paired DNA and RNA profiling are made possible with the advancement of sequencing technology. Traditional approaches, however, usually required preparing DNA and RNA samples in parallel, which meant the data obtained were not necessarily from the same set of cell population. Thus, these separate workflows might yield less correlative DNA and RNA data due to the heterogeneity of the sample. In addition, they added extra time and effort because of doubled workload.

In order to circumvent the disadvantage of separate workflow, researchers tried to integrate them. DR-seq (Dey S S et al., *Nat. Biotechnol.* 33:285-289 (2015)) and G&T-seq (Macaulay I C et al., i Nat. Methods. 12:519-22 (2015)) were among the first few attempts of integrative analysis of genomic DNA and mRNA from a single cell. However, these methods were designed specifically for single cell applications.

Another group developed an integrated DNA and RNA sequencing workflow, named Simul-seq. Reuter J A et al., *Nat. Methods* 13:953-958 (2016). It is a streamlined approach to profiling whole genome and transcriptome from the same set of cell population. Simul-seq is designed for whole genome and transcriptome sequencing.

There remains a need for improved, integrated DNA and RNA preparations amenable for sequencing analysis.

BRIEF SUMMARY OF THE INVENTION

Disclosed herein are methods for preparing DNA and cDNA libraries from a sample, comprising: ligating a DNA tag to an end of a DNA molecule in a sample, wherein the DNA tag comprises a unique molecular identifier (UMI) and a DNA identifier; and performing reverse transcription of a RNA molecule in the sample in the presence of a RNA tag, wherein the RNA tag comprises a RNA identifier, a UMI, and a poly(T).

In some embodiments, the reverse transcription is performed in the presence of a second RNA tag, wherein the second RNA tag comprises a RNA identifier, a UMI, and a template switching oligonucleotide (TSO).

In some embodiments, the methods further comprise amplifying the tagged DNA and tagged cDNA for enrichment with a set of gene specific primers. In some embodiments, the methods further comprise separating the amplified sample into first and second samples.

In some embodiments, the DNA and RNA molecules are obtained from a biological sample. In some embodiments, the DNA and RNA molecules are fragmented DNA and RNA from the biological sample.

In some embodiments, the DNA molecule contains polished ends for ligation. In some embodiments, the RNA molecule is polyadenylated.

In some embodiments, the methods do not require ribosomal depletion.

In further embodiments, the methods further comprise further amplifying the first sample with primers specific for the DNA tag. The amplification can generate a DNA library corresponding to the DNA molecules in the sample.

In further embodiments, the methods further comprise further amplifying the second sample with primers specific for the RNA tag. The amplification generates a cDNA library corresponding to the RNA molecules in a sample.

In some embodiments, the methods further comprise sequencing the DNA or cDNA library. The DNA library can be used for, but not limited to, DNA variant detection, copy number analysis, fusion gene detection, or structural variant detection. The cDNA library can be used for, but not limited to, RNA variant detection, gene expression analysis, or fusion gene detection. The libraries can be also used for paired DNA and RNA profiling.

Also disclosed herein are DNA libraries made by the methods disclosed herein. Further disclosed are cDNA libraries made by the methods disclosed herein.

Also disclosed herein are DNA tags comprising a unique molecular identifier (UMI) and a DNA identifier. In some embodiments, in the DNA tags, the UMI and the DNA identifier can be positioned in a 5' to 3' direction.

Also disclosed herein are RNA tags comprising a RNA identifier, a UMI, and a poly(T). In some embodiments, in the RNA tags, the RNA identifier, the UMI, and the poly(T) are positioned in a 5' to 3' direction. Also disclosed herein are RNA tags comprising a RNA identifier, a UMI, and a template switching oligonucleotide (TSO). In some embodiments, in the RNA tags, the RNA identifier, the UMI, and the TSO are positioned in a 5' to 3' direction.

Disclosed herein are compositions comprising at least 2 of the above described tags. Also disclosed herein are compositions comprising the DNA tag and the 2 different RNA tags as described above.

Further disclosed herein are methods for preparing targeted DNA and cDNA libraries, comprising:
(a) obtaining purified DNA and RNA from a biological sample;
(b) fragmenting the DNA and RNA;
(c) polishing the ends of the double stranded DNA fragments for ligation;
(d) polishing the RNA fragments by polyadenylation;
(e) ligating a DNA tag to a 3' end of the polished DNA fragments, wherein the DNA tag comprises in a 5' to 3' direction a unique molecular identifier (UMI) and a DNA identifier;
(f) performing reverse transcription of the polished RNA fragments in the presence of a first RNA tag, wherein the first RNA tag comprises in a 5' to 3' direction a RNA identifier, a UMI, and a poly(T), and a second RNA tag, wherein the second RNA tag comprises in a 5' to 3' direction a RNA identifier, a UMI, and a template switching oligonucleotide (TSO);
(g) amplifying the tagged DNA and tagged cDNA for enrichment with a set of gene specific primers;
(h) separating the amplified sample into first and second samples;

(i) amplifying the first sample with primers specific for the DNA tag; and (j) amplifying the second sample with primers specific for the RNA tag.

BRIEF DESCRIPTION OF THE DRAWINGS/FIGURES

FIG. 1. Exemplary DNA and RNA tag molecules.

Figure 2:
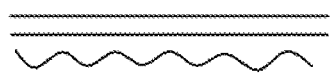
Figure 2:
Figure 2:
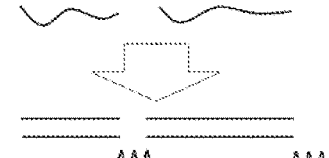
Figure 2:
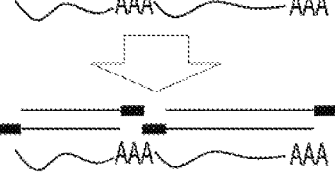
Figure 2:
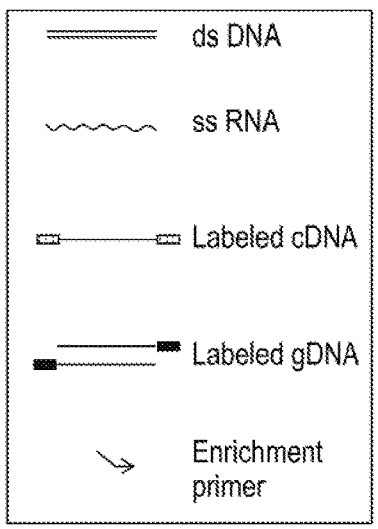
Figure 2:
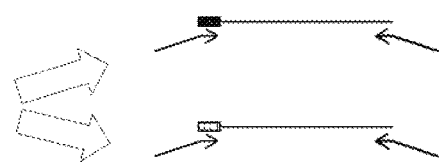

FIG. 2. Exemplary process for generating DNA and cDNA libraries.

DETAILED DESCRIPTION OF THE INVENTION

Disclosed herein are innovative approaches for integrative DNA and cDNA library preparations for analysis, such as by next-generation sequencing (NGS) analysis, without physical separation of DNA and RNA. These approaches integrate UMI (unique molecular index) technology and optionally, targeted enrichment technology, seamlessly into the workflow, which improve utilization of sequencing capacity and accuracy of the results. In addition, these methods output two separate DNA and cDNA libraries from DNA and RNA, respectively, which allow flexible manipulation on downstream sequencing platform. Compared to standalone DNA library and cDNA library methods, these approaches reduce sample consumption, simplify the experimental process, and can help researchers gain biological insights in genotype and phenotype correlations and molecular mechanisms of diseases.

Methods are described herein to prepare targeted DNA and cDNA libraries without the necessity of physical separation of genomic DNA (gDNA) and mRNA. The process involves three modules: (1) assign different DNA and RNA tag molecules to each individual DNA and RNA fragment, respectively, without separating them in the system; optionally, (2) amplify and enrich a subset of the tagged DNA and RNA fragments (target enrichment); and (3) differentially PCR amplify the tagged DNA and tagged cDNA in the (enriched) product to output two libraries corresponding to the original DNA and RNA, respectively.

The DNA and RNA tag molecules used in the first module are oligonucleotides comprising at least 1) an identifying sequence to distinguish a DNA library or RNA library, and 2) a UMI sequence for identifying each individual nucleic acid molecule.

The DNA and RNA tags are essential for the final separation of DNA and cDNA libraries in module 3, where they can serve as specific amplification primer sites for DNA and RNA. The UMI sequence helps improve accuracy for both DNA and RNA NGS analysis. Exemplary tag molecules are illustrated in FIG. 1.

Two types of RNA tag molecules can be used in order to sequence the single stranded RNA from both directions, and thus, two different mechanisms can be used to attach the RNA specific sequence. Only one type of DNA tag molecule is needed because the DNA tag molecule can be ligated to both ends of the double stranded DNA.

The targeted enrichment reaction (module 2) enables focused view on relevant regions of interest, and provides economic utilization of NGS sequencing capacity. It also mitigates the necessity for extra treatment of the sample associated with whole genome or transcriptome workflow, such as ribosomal RNA depletion. The enrichment is done in the same reaction for both DNA and RNA. Depending on the applications, the enrichment primer pool can be the same if the target DNA and RNA regions are the same. If different regions are of interest for the DNA and RNA, users can simply mix the corresponding enrichment primer pools, and put them into the same reaction.

Module 3 enables separated output of DNA and cDNA libraries. The sequencing depth requirements for DNA and cDNA are usually quite different, and they vary depending on the applications. The output from the methods disclosed herein gives users flexibility so that sequencing capacity can be allocated individually according to specific needs. In addition, since the samples have already been partially amplified in module 2, the separation has negligible effect on sample loss.

FIG. 2 illustrates one exemplary, optimized way to utilize the methods disclosed herein. It starts with purified (not necessarily separated) gDNA and RNA from a biological sample (step 1). The total nucleic acids are fragmented by enzymatic digestion (for DNA) and by heat hydrolysis (for RNA). The double stranded DNA fragments are end polished so that they are ready for ligation (step 2). The fragmented RNAs are end polished by polyadenylation (step 3). In the next few steps, DNA fragments are ligated to DNA tag molecules (step 4), and the RNA fragments are attached with RNA tag molecules (on both ends) by template switching reverse transcription (step 5). With both DNA and RNA tags in place, the sample is subjected to targeted enrichment reaction by a set of gene specific primers, in which the regions of interest are amplified and enriched (step 6). Finally, the sample is split into two samples, and further amplified by primers specific for the DNA tag and RNA tag, respectively, and with proper NGS adapter sequences compatible with, e.g., Illumina NGS platform (step 7). The final products are two separate DNA and cDNA libraries resulted from the original DNA and RNA material, respectively, and are ready for sequencing.

Disclosed herein are methods for preparing DNA and cDNA libraries from a sample, comprising: ligating a DNA tag to an end of a DNA molecule in a sample, wherein the DNA tag comprises a unique molecular identifier (UMI) and a DNA identifier; and performing reverse transcription of a RNA molecule in the sample in the presence of a RNA tag, wherein the RNA tag comprises a RNA identifier, a UMI, and a poly(T). The methods do not require physical separation of the DNA and RNA from the sample.

In some embodiments, the reverse transcription is performed in the presence of a second RNA tag, wherein the second RNA tag comprises a RNA identifier, a UMI, and a template switching oligonucleotide (TSO).

In some embodiments, the methods can include ribosomal depletion. Alternatively, in some embodiments, the methods do not require ribosomal depletion. Methods for ribosomal depletion are known in the art, e.g., using RiboZero gold (Illumina: MRZG126).

The term "sample" can include RNA, DNA, a single cell, multiple cells, fragments of cells, or an aliquot of body fluid, taken from a subject (e.g., a mammalian subject, an animal subject, a human subject, or a non-human animal subject). Samples can be selected by one of skill in the art using any known means known including but not limited to centrifugation, venipuncture, blood draw, excretion, swabbing, biopsy, needle aspirate, lavage sample, scraping, surgical incision, laser capture microdissection, gradient separation, or intervention or other means known in the art. The term "mammal" or "mammalian" as used herein includes both humans and non-humans and include but is not limited to humans, non-human primates, canines, felines, murines, bovines, equines, and porcines.

As used herein, the term "biological sample" is intended to include, but is not limited to, tissues, cells, biological fluids and isolates thereof, isolated from a subject, as well as tissues, cells, and fluids present within a subject.

As used herein, a "single cell" refers to one cell. Single cells useful in the methods described herein can be obtained from a tissue of interest, or from a biopsy, blood sample, or cell culture. Additionally, cells from specific organs, tissues, tumors, neoplasms, or the like can be obtained and used in the methods described herein. In general, cells from any population can be used in the methods, such as a population of prokaryotic or eukaryotic organisms, including bacteria or yeast.

A single cell suspension can be obtained using standard methods known in the art including, for example, enzymatically using trypsin or papain to digest proteins connecting cells in tissue samples or releasing adherent cells in culture, or mechanically separating cells in a sample. Samples can also be selected by one of skill in the art using one or more markers known to be associated with a sample of interest.

Methods for manipulating single cells are known in the art and include fluorescence activated cell sorting (FACS), micromanipulation and the use of semi-automated cell pickers (e.g., the Quixell™ cell transfer system from Stoelting Co.). Individual cells can, for example, be individually selected based on features detectable by microscopic observation, such as location, morphology, or reporter gene expression.

Once a desired sample has been identified, the sample is prepared and the cell(s) are lysed to release cellular contents including DNA and RNA, such as gDNA and mRNA, using methods known to those of skill in the art. Lysis can be achieved by, for example, heating the cells, or by the use of detergents or other chemical methods, or by a combination of these. Any suitable lysis method known in the art can be used.

Nucleic acids from a cell such as DNA or RNA are isolated using methods known to those of skill in the art.

The term "polynucleotide(s)" or "oligonucleotide(s)" refers to nucleic acids such as DNA molecules and RNA molecules and analogs thereof (e.g., DNA or RNA generated using nucleotide analogs or using nucleic acid chemistry). As desired, the polynucleotides can be made synthetically, e.g., using art-recognized nucleic acid chemistry or enzymatically using, e.g., a polymerase, and, if desired, can be modified. Typical modifications include methylation, biotinylation, and other art-known modifications. In addition, a polynucleotide can be single-stranded or double-stranded and, where desired, linked to a detectable moiety. In some aspects, a polynucleotide can include hybrid molecules, e.g., comprising DNA and RNA.

"G," "C," "A," "T" and "U" each generally stands for a nucleotide that contains guanine, cytosine, adenine, thymidine and uracil as a base, respectively. However, it will be understood that the term "ribonucleotide" or "nucleotide" can also refer to a modified nucleotide or a surrogate replacement moiety. The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in nucleotide sequences by a nucleotide containing, for example, inosine. In another example, adenine and cytosine anywhere in the oligonucleotide can be replaced with guanine and uracil, respectively, to form G-U Wobble base pairing with the target mRNA. Sequences containing such replacement moieties are suitable for the compositions and methods described herein.

The term "DNA" refers to chromosomal DNA, plasmid DNA, phage DNA, or viral DNA that is single stranded or double stranded. DNA can be obtained from prokaryotes or eukaryotes.

The term "genomic DNA" or "gDNA" refers to chromosomal DNA.

The term "messenger RNA" or "mRNA" refers to an RNA that is without introns and that can be translated into a polypeptide.

The term "cDNA" refers to a DNA that is complementary or identical to an mRNA, in either single stranded or double stranded form.

As used herein, "polymerase" and its derivatives, generally refers to any enzyme that can catalyze the polymerization of nucleotides (including analogs thereof) into a nucleic acid strand. Typically but not necessarily, such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain. Optionally, the polymerase can possess 5' exonuclease activity or terminal transferase activity. In some embodiments, the polymerase can be optionally reactivated, for example through the use of heat, chemicals or re-addition of new amounts of polymerase into a reaction mixture. In some embodiments, the polymerase can include a hot-start polymerase or an aptamer based polymerase that optionally can be reactivated.

The term "extension" and its variants, as used herein, when used in reference to a given primer, comprises any in vivo or in vitro enzymatic activity characteristic of a given polymerase that relates to polymerization of one or more nucleotides onto an end of an existing nucleic acid molecule. Typically but not necessarily such primer extension occurs in a template-dependent fashion; during template-dependent extension, the order and selection of bases is driven by established base pairing rules, which can include Watson-Crick type base pairing rules or alternatively (and especially in the case of extension reactions involving nucleotide analogs) by some other type of base pairing paradigm. In one non-limiting example, extension occurs via polymerization of nucleotides on the 3'OH end of the nucleic acid molecule by the polymerase.

As used herein, the terms "ligating," "ligation," and their derivatives refer generally to the act or process for covalently linking two or more molecules together, for example, covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, for example embodiments wherein the nucleic acid molecules to be ligated include conventional nucleotide residues, the ligation can include forming a covalent bond between a 5' phosphate group of one nucleic acid and a 3' hydroxyl group of a second nucleic acid thereby forming a ligated nucleic acid molecule. In some embodiments, any means for joining nicks or bonding a 5'phosphate to a 3' hydroxyl between adjacent nucleotides can be employed. In an exemplary embodiment, an enzyme such as a ligase can be used. Generally for the purposes of this disclosure, an amplified target sequence can be ligated to an adapter to generate an adapter-ligated amplified target sequence.

As used herein, "ligase" and its derivatives, refers generally to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases can include, but not limited to, T4 DNA ligase, T4 RNA ligase, and *E. coli* DNA ligase.

As used herein, "ligation conditions" and its derivatives, generally refers to conditions suitable for ligating two molecules to each other. In some embodiments, the ligation conditions are suitable for sealing nicks or gaps between nucleic acids. As defined herein, a "nick" or "gap" refers to a nucleic acid molecule that lacks a directly bound 5' phosphate of a mononucleotide pentose ring to a 3' hydroxyl of a neighboring mononucleotide pentose ring within internal nucleotides of a nucleic acid sequence. As used herein, the term nick or gap is consistent with the use of the term in the art. Typically, a nick or gap can be ligated in the presence of an enzyme, such as ligase at an appropriate temperature and pH. In some embodiments, T4 DNA ligase can join a nick between nucleic acids at a temperature of about 70° C.-72° C.

As used herein, "blunt-end ligation" and its derivatives, refers generally to ligation of two blunt-end double-stranded nucleic acid molecules to each other. A "blunt end" refers to an end of a double-stranded nucleic acid molecule wherein substantially all of the nucleotides in the end of one strand of the nucleic acid molecule are base paired with opposing nucleotides in the other strand of the same nucleic acid molecule. A nucleic acid molecule is not blunt ended if it has an end that includes a single-stranded portion greater than two nucleotides in length, referred to herein as an "overhang." In some embodiments, the end of nucleic acid molecule does not include any single stranded portion, such that every nucleotide in one strand of the end is based paired with opposing nucleotides in the other strand of the same nucleic acid molecule. In some embodiments, the ends of the two blunt ended nucleic acid molecules that become ligated to each other do not include any overlapping, shared or complementary sequence. Typically, blunted-end ligation excludes the use of additional oligonucleotide adapters to assist in the ligation of the double-stranded amplified target sequence to the double-stranded adapter, such as patch oligonucleotides as described in Mitra and Varley, US2010/0129874. In some embodiments, blunt-ended ligation includes a nick translation reaction to seal a nick created during the ligation process.

The term "amplicon" refers to the amplified product of a nucleic acid amplification reaction, e.g., RT-PCR.

The terms "reverse-transcriptase PCR" and "RT-PCR" refer to a type of PCR where the starting material is mRNA. The starting mRNA is enzymatically converted to complementary DNA or "cDNA" using a reverse transcriptase enzyme. The cDNA is then used as a template for a PCR reaction.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.). Amplification methods include PCR methods known to those of skill in the art and also include rolling circle amplification (Blanco et al., J. Biol. Chem., 264, 8935-8940, 1989), hyperbranched rolling circle amplification (Lizard et al., Nat. Genetics, 19, 225-232, 1998), and loop-mediated isothermal amplification (Notomi et al., Nucl. Acids Res., 28, e63, 2000), each of which is hereby incorporated by reference in its entirety.

The term "hybridize" refers to a sequence specific non-covalent binding interaction with a complementary nucleic acid. Hybridization can occur to all or a portion of a nucleic acid sequence. Those skilled in the art will recognize that the stability of a nucleic acid duplex, or hybrids, can be determined by the Tm. Additional guidance regarding hybridization conditions can be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, Vol. 3, 1989.

As used herein, "incorporating" a sequence into a polynucleotide refers to covalently linking a series of nucleotides with the rest of the polynucleotide, for example at the 3' or 5' end of the polynucleotide, by phosphodiester bonds, wherein the nucleotides are linked in the order prescribed by the sequence. A sequence has been "incorporated" into a polynucleotide, or equivalently the polynucleotide "incorporates" the sequence, if the polynucleotide contains the sequence or a complement thereof. Incorporation of a sequence into a polynucleotide can occur enzymatically (e.g., by ligation or polymerization) or using chemical synthesis (e.g., by phosphoramidite chemistry).

As used herein, the terms "amplify" and "amplification" refer to enzymatically copying the sequence of a polynucleotide, in whole or in part, so as to generate more polynucleotides that also contain the sequence or a complement thereof. The sequence being copied is referred to as the template sequence. Examples of amplification include DNA-templated RNA synthesis by RNA polymerase, RNA-templated first-strand cDNA synthesis by reverse transcriptase, and DNA-templated PCR amplification using a thermostable DNA polymerase. Amplification includes all primer-extension reactions. Amplification includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., "PCR protocols: a guide to method and applications" Academic Press, Incorporated (1990) (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting amplification reaction are commercially available. Primers useful to amplify sequences from a particular gene region are preferably complementary to, and hybridize specifically to sequences in the target region or in its flanking regions and can be prepared using the polynucleotide sequences provided herein. Nucleic acid sequences generated by amplification can be sequenced directly.

The term "associated" is used herein to refer to the relationship between a sample and the DNA molecules, RNA molecules, or other polynucleotides originating from or derived from that sample. A polynucleotide is associated with a sample if it is an endogenous polynucleotide, i.e., it occurs in the sample at the time the sample is selected, or is derived from an endogenous polynucleotide. For example, the mRNAs endogenous to a cell are associated with that cell. cDNAs resulting from reverse transcription of these mRNAs, and DNA amplicons resulting from PCR amplification of the cDNAs, contain the sequences of the mRNAs and are also associated with the cell. The polynucleotides associated with a sample need not be located or synthesized in the sample, and are considered associated with the sample even after the sample has been destroyed (for example, after a cell has been lysed). Molecular barcoding or other techniques can be used to determine which polynucleotides in a mixture are associated with a particular sample.

When hybridization occurs in an antiparallel configuration between two single-stranded polynucleotides, the reaction is called "annealing" and those polynucleotides are described as "complementary". As used herein, and unless otherwise indicated, the term "complementary," when used to describe a first nucleotide sequence in relation to a second nucleotide sequence, refers to the ability of a polynucleotide comprising the first nucleotide sequence to hybridize and form a duplex structure under certain conditions with a polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing. Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences include base-pairing of a region of a polynucleotide comprising a first nucleotide sequence to a region of a polynucleotide comprising a second nucleotide sequence over the length or a portion of the length of one or both nucleotide sequences. Such sequences can be referred to as "complementary" with respect to each other herein. However, where a first sequence is referred to as "substantially complementary" with respect to a second sequence herein, the two sequences can be complementary, or they can include one or more, but generally not more than about 5, 4, 3, or 2 mismatched base pairs within regions that are base-paired. For two sequences with mismatched base pairs, the sequences will be considered "substantially complementary" as long as the two nucleotide sequences bind to each other via base-pairing.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

In some embodiments, the double stranded DNA fragments can be end polished so that they are amenable for ligation. For example, the ends of the DNA fragments can be polished to have blunt ends. As known in the art, this can be achieved with enzymes that can either fill in or remove the protruding strand. Another method is to perform the ligation in the presence of short synthetic oligonucleotides, called "adaptors," which have been prepared in such a way as to eventually ligate with one terminus to the fragment and make the fragment amenable for ligation with polynucleotides of interest such as DNA or RNA tags. As such, the DNA fragments can be ligated to DNA tags.

In some embodiments, the RNA fragments are end polished by polyadenylation. The RNA fragments can be attached to RNA tags, e.g., on both ends, by template switching reverse transcription.

A "DNA tag" or "DNA tag molecule" is a polynucleotide comprising a DNA identifier and a UMI. A DNA tag can be a deoxyribopolynucleotide. A "DNA identifier" is a polynucleotide sequence assigned to distinguish a gDNA molecule from a RNA molecule. A DNA tag can be ligated to the 5' or 3' end of double stranded DNA fragments.

A "RNA tag" or "RNA tag molecule" is a polynucleotide comprising a RNA identifier and a UMI. A RNA tag can be a deoxyribopolynucleotide. A "RNA identifier" is a polynucleotide sequence assigned to distinguish a cDNA molecule from a gDNA molecule. A RNA tag can further comprise poly(T). Alternatively, a RNA tag can further comprise a template switching oligonucleotide (TSO). A RNA tag can be used to add a 5' tag to RNA-derived cDNA fragments through reverse transcription. In some embodiments, a RNA tag can be used to add a 3' tag to RNA-derived cDNA through template switching in reverse transcription.

Two types of RNA tags are helpful because in order to sequence the single stranded RNA from both directions, two different mechanisms can be used to attach the RNA specific sequence. Only one type of DNA tag is needed because the DNA tag can be ligated to both ends of the double stranded DNA.

A composition can comprise at least 2 of the tags described above, e.g., a DNA tag and a RNA tag. A composition can also comprise the 3 tags described above, e.g., a DNA tag and the 2 types of RNA tags.

Unique molecular indices or identifiers (UMIs; also called Random Molecular Tags (RMTs)) are short sequences or "barcodes" of bases used to tag each DNA or RNA molecule (fragment) prior to library amplification, thereby aiding in the identification of each individual nucleic acid molecule, or PCR duplicates. Kivioja, T. et al., *Nat. Methods* 9:72-74 (2012), and Suppl. If two reads align to the same location and have the same UMI, it is highly likely that they are PCR duplicates originating from the same fragment prior to amplification. UMIs can also be used to detect and quantify unique mRNA transcripts. In some embodiments, DNA tags containing the same DNA identifier sequence contain different UMI sequences. In some embodiments, RNA tags containing the same RNA identifier sequence contain different UMI sequences.

The concept of UMIs is that prior to any amplification, each original target molecule is 'tagged' by a unique barcode sequence. This DNA sequence must be long enough to provide sufficient permutations to assign each founder molecule a unique barcode. In some embodiments, a UMI sequence contains randomized nucleotides and is incorporated into the DNA or RNA tag. For example, a 12-base random sequence provides $4^{12}$ or 16,777,216 UMI's for each target molecule in the sample.

In some embodiments, the RNA tag is a single-stranded DNA molecule and serves as a primer for reverse transcription. The RNA tag can be generated using a DNA polymerase (DNAP). Here, the binding site of the RNA tag is an RNA binding site (e.g., an mRNA binding site) and contains a sequence region complementary to a sequence region in one or more RNAs. In some embodiments, the binding site is complementary to a sequence region common to all RNAs in the sample to which the barcode adapter is added. For example, the binding site can be a poly(T) tract, which is complementary to the poly(A) tails of eukaryotic mRNAs. Alternatively or in addition, the binding site can include a random sequence tract. Upon adding the RNA tag to the RNAs associated with a sample, reverse transcription can occur and first strands of cDNA can be synthesized, such that the RNA identifier sequence is incorporated into the first strands of cDNA. It will be recognized that reverse transcription requires appropriate conditions, for example the presence of an appropriate buffer and reverse transcriptase enzyme, and temperatures appropriate for annealing of the barcode adapter to RNAs and the activity of the enzyme. It will also be recognized that reverse transcription, involving a DNA primer and an RNA template, is most efficient when the 3' end of the primer is complementary to the template and can anneal directly to the template. Accordingly, the RNA tag can be designed so that the binding site occurs at the 3' end of the adapter molecule.

As described above, the present methods can employ a reverse transcriptase enzyme that adds one or more non-templated nucleotides (such as Cs) to the end of a nascent cDNA strand upon reaching the 5' end of the template RNA. These nucleotides form a 3' DNA overhang at one end of the RNA/DNA duplex. If a second RNA molecule contains a sequence region, for example, a poly-G tract at its 3' end that is complementary to the non-templated nucleotides, and binds to the non-templated nucleotides, the reverse transcriptase can switch templates and continue extending the cDNA, now using the second RNA molecule as a template. Such a second RNA molecule is referred to herein and known in the art as a template-switching oligo (TSO).

In embodiments of the present methods, a second RNA tag comprising a RNA identifier, UMI, and TSO can serve as a template-switching oligonucleotide for reverse transcription. Thus, the RNA identifier sequence is incorporated into the first strand of cDNA after template switching, and is present in DNA molecules resulting from amplification (for example, by PCR) of the first strand of cDNA. In these embodiments, any reverse transcriptase that has template switching activity can be used. The binding site of the first RNA tag is a cDNA binding site and preferably occurs at the 3' end of the adapter molecule. The binding site can include a G-tract (comprising one or more G nucleotides), or any other sequence that is at least partially complementary to that of the 3' overhang generated by the reverse transcriptase. It will be recognized that the overhang sequence, and thus an appropriate sequence for the binding site of the barcode adapter, can depend on the choice of reverse transcriptase used in the method.

Methods for reverse transcription and template switching are well known in the art. A procedure frequently referred to as "SMART" (switching mechanism at the 5' end of the RNA transcript) can generate full-length cDNA libraries, even from single-cell-derived RNA samples. This strategy relies on the intrinsic properties of Moloney murine leukemia virus (MMLV) reverse transcriptase and the use of a unique template switching oligonucleotide (TS oligo, or TSO). Moloney Murine Leukemia Virus Reverse Transcriptase (M-MLV RT) is an RNA-dependent DNA polymerase that can be used in cDNA synthesis with long messenger RNA templates (>5 kb). The enzyme is a product of the pol gene of M-MLV and consists of a single subunit with a molecular weight of 71 kDa. During first-strand synthesis, upon reaching the 5' end of the RNA template, the terminal transferase activity of the MMLV reverse transcriptase adds a few additional nucleotides (mostly deoxycytidine) to the 3' end of the newly synthesized cDNA strand. These bases function as a TS oligo-anchoring site. Upon base pairing between the TS oligo and the appended deoxycytidine stretch, the reverse transcriptase "switches" template strands, from cellular RNA to the TS oligo, and continues replication to the 5' end of the TS oligo. By doing so, the resulting cDNA contains the complete 5' end of the transcript, and universal sequences of choice can be added to the reverse transcription product. Along with tagging of the cDNA 3' end by oligo dT primers, this approach makes it possible to efficiently amplify the entire full-length transcript pool in a completely sequence-independent manner.

A TS oligo can be a DNA oligo sequence that carries 3 riboguanosines (rGrGrG) at its 3' end. The complementarity between these consecutive rG bases and the 3' dC extension of the cDNA molecule allows the subsequent template switching. The 3' most rG can also be replaced with a locked nucleic acid base (LNA) to enhance thermostability of the LNA monomer, which would be advantageous for base pairing.

The TSO can include a 3' portion comprising a plurality of guanosines or guanosine analogues that base pair with cytosine. Non-limiting examples of guanosines or guanosine analogues useful in the methods described herein include, but are not limited to, deoxyriboguanosine, riboguanosine, locked nucleic acid-guanosine, and peptide nucleic acid-guanosine. The guanosines can be ribonucleosides or locked nucleic acid monomers.

The TSO can include a 3' portion including at least 2, at least 3, at least 4, at least 5, or 2, 3, 4, or 5, or 2-5 guanosines, or guanosine analogues that base pair with cytosine. The presence of a plurality of guanosines (or guanosine analogues that base pair with cytosine) allows the TSO to anneal transiently to the exposed cytosines at the 3' end of the first strand of cDNA. This causes the reverse transcriptase to switch template and continue to synthesis a strand complementary to the TSO. In one aspect of the invention, the 3' end of the TSO can be blocked, for example by a 3' phosphate group, to prevent the TSO from functioning as a primer during cDNA synthesis.

Before the tagged cDNA samples are pooled, synthesis of cDNA can be stopped, for example by removing or inactivating the reverse transcriptase. This prevents cDNA synthesis by reverse transcription from continuing in the pooled samples.

As used herein, "amplified target sequences" and its derivatives, refers generally to a nucleic acid sequence produced by the amplification of/amplifying the target sequences using target-specific primers and the methods provided herein. The amplified target sequences can be either of the same sense (the positive strand produced in the second round and subsequent even-numbered rounds of amplification) or antisense (i.e., the negative strand produced during the first and subsequent odd-numbered rounds of amplification) with respect to the target sequences. For the purposes of this disclosure, the amplified target sequences are typically less than 50% complementary to any portion of another amplified target sequence in the reaction.

The term "polymerase chain reaction" ("PCR") of Mullis (U.S. Pat. Nos. 4,683,195, 4,683,202, and 4,965,188) refers to a method for increasing the concentration of a segment of a target sequence in a mixture of nucleic acid sequences without cloning or purification. This process for amplifying the target sequence consists of introducing a large excess of two oligonucleotide primers to the nucleic acid sequence mixture containing the desired target sequence, followed by a precise sequence of thermal cycling in the presence of a polymerase (e.g., DNA polymerase). The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

The methods disclosed herein can further comprise amplifying the tagged DNA the tagged cDNA for enrichment with a set of gene specific primers. Target enrichment can be achieved with, e.g., an SPE primer pool, DNA boosting primer, and RNA boosting primer. Amplicon-based next-generation sequencing (NGS) assays offer many advantages for targeted enrichment. For example, QIAseq NGS panels employ unique molecular indices (UMI's) to correct for PCR amplification bias and use single primer extension (SPE) technology which provides design flexibility and highly-specific target enrichment. The concept of UMIs is that prior to any amplification, each original target molecule is 'tagged' by a unique barcode sequence. This DNA sequence must be long enough to provide sufficient permutations to assign each founder molecule a unique barcode. In its current form, a 12-base random sequence provides $4^{12}$ or 16,777,216 UMI's for each target molecule in the sample.

As used herein, the term "primer" includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers usually have a length in the range of between 3 to 36 nucleotides, also 5 to 24 nucleotides, also from 14 to 36 nucleotides. Primers within the scope of the invention include orthogonal primers, amplification primers, constructions primers and the like. Pairs of primers can flank a sequence of interest or a set of sequences of interest. Primers and probes can be degenerate in sequence. Primers within the scope of the present invention bind adjacent to a target sequence. A "primer" can be considered a short polynucleotide, generally with a free 3'-OH group that binds to a target or template potentially present in a sample of interest by hybridizing with the target, and thereafter promoting polymerization of a polynucleotide complementary to the target. Primers of the instant invention are comprised of nucleotides ranging from 17 to 30 nucleotides. In some embodiments, the primer is at least 17 nucleotides, or alternatively, at least 18 nucleotides, or alternatively, at least 19 nucleotides, or alternatively, at least 20 nucleotides, or alternatively, at least 21 nucleotides, or alternatively, at least 22 nucleotides, or alternatively, at least 23 nucleotides, or alternatively, at least 24 nucleotides, or alternatively, at least 25 nucleotides, or alternatively, at least 26 nucleotides, or alternatively, at least 27 nucleotides, or alternatively, at least 28 nucleotides, or alternatively, at least 29 nucleotides, or alternatively, at least 30 nucleotides, or alternatively at least 50 nucleotides, or alternatively at least 75 nucleotides or alternatively at least 100 nucleotides.

As used herein, "target-specific primer" and its derivatives, refers generally to a single stranded or double-stranded polynucleotide, typically an oligonucleotide, that includes at least one sequence that is at least 50% complementary, typically at least 75% complementary or at least 85% complementary, more typically at least 90% complementary, more typically at least 95% complementary, more typically at least 98% or at least 99% complementary, or 100% identical, to at least a portion of a nucleic acid molecule that includes a target sequence. In such instances, the target-specific primer and target sequence are described as "corresponding" to each other. In some embodiments, the target-specific primer is capable of hybridizing to at least a portion of its corresponding target sequence (or to a complement of the target sequence); such hybridization can optionally be performed under standard hybridization conditions or under stringent hybridization conditions. In some embodiments, the target-specific primer is not capable of hybridizing to the target sequence, or to its complement, but is capable of hybridizing to a portion of a nucleic acid strand including the target sequence, or to its complement. In some embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the target sequence itself; in other embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the nucleic acid molecule other than the target sequence. In some embodiments, the target-specific primer is substantially non-complementary to other target sequences present in the sample; optionally, the target-specific primer is substantially non-complementary to other nucleic acid molecules present in the sample. In some embodiments, nucleic acid molecules present in the sample that do not include or correspond to a target sequence (or to a complement of the target sequence) are referred to as "non-specific" sequences or "non-specific nucleic acids". In some embodiments, the target-specific primer is designed to include a nucleotide sequence that is substantially complementary to at least a portion of its corresponding target sequence. In some embodiments, a target-specific primer is at least 95% complementary, or at least 99% complementary, or 100% identical, across its entire length to at least a portion of a nucleic acid molecule that includes its corresponding target sequence. In some embodiments, a target-specific primer can be at least 90%, at least 95% complementary, at least 98% complementary or at least 99% complementary, or 100% identical, across its entire length to at least a portion of its corresponding target sequence. In some embodiments, a forward target-specific primer and a reverse target-specific primer define a target-specific primer pair that can be used to amplify the target sequence via template-dependent primer extension. Typically, each primer of a target-specific primer pair includes at least one sequence that is substantially complementary to at least a portion of a nucleic acid molecule including a corresponding target sequence but that is less than 50% complementary to at least one other target sequence in the sample. In some embodiments, amplification can be performed using multiple target-specific primer pairs in a single amplification reaction, wherein each primer pair includes a forward target-specific primer and a reverse target-specific primer, each including at least one sequence that substantially complementary or substantially identical to a corresponding target sequence in the sample, and each primer pair having a different corresponding target sequence. In some embodiments, the target-specific primer can be substantially non-complementary at its 3' end or its 5' end to any other target-specific primer present in an amplification reaction. In some embodiments, the target-specific primer can include minimal cross hybridization to other target-specific primers in the amplification reaction. In some embodiments, target-specific primers include minimal cross-hybridization to non-specific sequences in the amplification reaction mixture. In some embodiments, the target-specific primers include minimal self-complementarity. In some embodiments, the target-specific primers can include one or more cleavable groups located at the 3' end. In some embodiments, the target-specific primers can include one or more cleavable groups located near or about a central nucleotide of the target-specific primer. In some embodiments, one of more targets-specific primers includes only non-cleavable nucleotides at the 5' end of the target-specific primer. In some embodiments, a target specific primer includes minimal nucleotide sequence overlap at the 3' end or the 5' end of the primer as compared to one or more different target-specific primers, optionally in the same amplification reaction. In some embodiments 1, 2, 3, 4, 5, 6, 7, 8, 9, 10 or more, target-specific primers in a single reaction mixture include one or more of the above embodiments. In some embodiments, substantially all of the plurality of target-specific primers in a single reaction mixture includes one or more of the above embodiments.

Primer design is based on single primer extension, in which each genomic target is enriched by one target-specific primer and one universal primer—a strategy that removes conventional two target-specific primer design restriction and reduces the amount of required primers. All primers required for a panel are pooled into an individual primer pool to reduce panel handling and the number of pools required for enrichment and library construction.

The booster panel is a pool of up to 100 primers that can be used to boost the performance of certain primers in any panel (cataloged, extended, or custom), or to extend the contents of an existing custom panel. The primers are delivered as a single pool that can be spiked into the existing panel.

After removing unused adapters, a limited number of PCR cycles can be conducted using an adapter primer and a pool of single primers, each carrying a gene specific sequence and a 5' universal sequence. During this process, each single primer repeatedly samples the same target locus from different DNA templates. Afterwards, additional PCR cycles can be conducted using universal primers to attach complete adapter sequences and to amplify the library to the desired quantity.

Compared to existing targeted enrichment approaches, the SPE method relies on single end adapter ligation, which inherently has a much higher efficiency than requiring adapters to ligate to both ends of the dsDNA fragment. More DNA molecules will be available for the downstream PCR enrichment step. PCR enrichment efficiency using one primer is also better than conventional two primer approach, due to the absence of an efficiency constraint from a second primer. During the initial PCR cycles, primers have repeated opportunities to convert (i.e. capture) maximal amount of original DNA molecules into amplicons.

All three features help to increase the efficiency of capturing rare mutations in the sample. In addition, incorporated UMI's within the amplicon are the key to estimating the number of DNA molecules captured and to greatly reduce sequencing errors in downstream analysis. Single primer extension also permits discovery of unknown structural variants, such as gene fusions.

The targeted enriched sample of DNA (e.g., gDNA) and cDNA are split into 2 separate samples. A first sample can be amplified by polymerase chain reaction (PCR) using primers specific for the DNA tag to generate a DNA library corresponding to the DNA in the sample. A second sample can be amplified by PCR using primers specific for the RNA tag to generate a cDNA library corresponding to the RNA in the sample.

A real-time polymerase chain reaction (Real-Time PCR), also known as quantitative polymerase chain reaction (qPCR), is a laboratory technique of molecular biology based on the polymerase chain reaction (PCR). It monitors the amplification of a targeted DNA molecule during the PCR, i.e. in real-time, and not at its end, as in conventional PCR. Real-time PCR can be used quantitatively (quantitative real-time PCR), and semi-quantitatively, i.e. above/below a certain amount of DNA molecules (semi quantitative real-time PCR). Other types of PCRs include but are not limited to nested PCR (used to analyze DNA sequences coming from different organisms of the same species but that can differ for a single nucleotide (SNIPS) and to ensure amplification of the sequence of interest in each of the organism analyzed) and Inverse-PCR (usually used to clone a region flanking an insert or a transposable element).

Two common methods for the detection of PCR products in real-time PCR are: (1) non-specific fluorescent dyes that intercalate with any double-stranded DNA, and (2) sequence-specific DNA probes consisting of oligonucleotides that are labeled with a fluorescent reporter which permits detection only after hybridization of the probe with its complementary sequence.

Methods and kits for performing PCR are well known in the art. PCR is a reaction in which replicate copies are made of a target polynucleotide using a pair of primers or a set of primers consisting of an upstream and a downstream primer, and a catalyst of polymerization, such as a DNA polymerase, and typically a thermally-stable polymerase enzyme. Methods for PCR are well known in the art, and taught, for example in MacPherson et al. (1991) PCR 1: A Practical Approach (IRL Press at Oxford University Press).

Embodiments of the invention provide 2 separate libraries for flexible manipulation downstream: a DNA library based on the original DNA and a cDNA library based on the original RNA produced by any of the methods described herein. The DNA library or cDNA library can be sequenced to provide an analysis of gene expression in single cells or in a plurality of single cells.

The amplified DNA or cDNA library can be sequenced and analyzed using methods known to those of skill in the art, e.g., by next-generation sequencing (NGS). In certain exemplary embodiments, RNA expression profiles are determined using any sequencing methods known in the art. Determination of the sequence of a nucleic acid sequence of interest can be performed using a variety of sequencing methods known in the art including, but not limited to, sequencing by synthesis (SBS), sequencing by hybridization (SBH), sequencing by ligation (SBL) (Shendure et al. (2005) Science 309:1728), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (U.S. Ser. No. 12/027,039, filed Feb. 6, 2008; Porreca et al (2007) Nat. Methods 4:931), polymerized colony (POLONY) sequencing (U.S. Pat. Nos. 6,432,360, 6,485,944 and 6,511,803, and PCT/US05/06425); nanogrid rolling circle sequencing (ROLONY) (US2009/0018024), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., using platforms such as Roche 454, Illumina Solexa, AB-SOLiD, Helicos, Complete Genomics, Polonator platforms and the like, can also be utilized. A variety of light-based sequencing technologies are known in the art (Landegren et al. (1998) Genome Res. 8:769-76; Kwok (2000) Pharmacogenomics 1:95-100; and Shi (2001) Clin. Chem. 47:164-172).

Embodiments of the invention also provide methods for analyzing gene expression in a plurality of single cells, the method comprising the steps of preparing a cDNA library using the method described herein and sequencing the cDNA library. A "gene" refers to a polynucleotide containing at least one open reading frame (ORF) that is capable of encoding a particular polypeptide or protein after being transcribed and translated. Any of the polynucleotide sequences described herein can be used to identify larger fragments or full-length coding sequences of the gene with which they are associated. Methods of isolating larger fragment sequences are known to those of skill in the art.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression can include splicing of the mRNA in a eukaryotic cell.

The cDNA library can be sequenced by any suitable screening method. In particular, the cDNA library can be sequenced using a high-throughput screening method, such as Applied Biosystems' SOLiD sequencing technology, or Illumina's Genome Analyzer. In one aspect of the invention, the cDNA library can be shotgun sequenced. The number of reads can be at least 10,000, at least 1 million, at least 10 million, at least 100 million, or at least 1000 million. In another aspect, the number of reads can be from 10,000 to 100,000, or alternatively from 100,000 to 1 million, or alternatively from 1 million to 10 million, or alternatively from 10 million to 100 million, or alternatively from 100 million to 1000 million. A "read" is a length of continuous nucleic acid sequence obtained by a sequencing reaction.

The DNA or gDNA library generated by the methods disclosed herein can be useful for, but not limited to, DNA variant detection, copy number analysis, fusion gene detection and structural variant detection. The cDNA library generated by the methods disclosed herein can be useful for, but not limited to, RNA variant detection, gene expression analysis, and fusion gene detection. The DNA and cDNA libraries can also be used for paired DNA and RNA profiling.

The expression profiles described herein are useful in the field of predictive medicine in which diagnostic assays, prognostic assays, pharmacogenomics, and monitoring clinical trials are used for prognostic (predictive) purposes to thereby treat an individual prophylactically. Accordingly, some embodiments relate to diagnostic assays for determining the expression profile of nucleic acid sequences (e.g., RNAs), in order to determine whether an individual is at risk of developing a disorder and/or disease. Such assays can be used for prognostic or predictive purposes to thereby prophylactically treat an individual prior to the onset of the disorder and/or disease. Accordingly, in certain exemplary embodiments, methods of diagnosing and/or prognosing one or more diseases and/or disorders using one or more of expression profiling methods described herein are provided.

Some embodiments pertain to monitoring the influence of agents (e.g., drugs or other compounds administered either to inhibit or to treat or prevent a disorder and/or disease) on the expression profile of nucleic acid sequences (e.g., RNAs) in clinical trials. Accordingly, in certain exemplary embodiments, methods of monitoring one or more diseases and/or disorders before, during and/or subsequent to treatment with one or more agents using one or more of expression profiling methods described herein are provided.

Monitoring the influence of agents (e.g., drug compounds) on the level of expression of a marker of the invention can be applied not only in basic drug screening, but also in clinical trials. For example, the effectiveness of an agent to affect an expression profile can be monitored in clinical trials of subjects receiving treatment for a disease and/or disorder associated with the expression profile. In certain exemplary embodiments, the methods for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting one or more expression profiled in the pre-administration sample; (iii) obtaining one or more post-administration samples from the subject; (iv) detecting one or more expression profiles in the post-administration samples; (v) comparing the one or more expression profiled in the pre-administration sample with the one or more expression profiles in the post-administration sample or samples; and (vi) altering the administration of the agent to the subject accordingly.

The expression profiling methods described herein allow the quantitation of gene expression. Thus, not only tissue specificity, but also the level of expression of a variety of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the time course of expression of one or more nucleic acid sequences (e.g., genes, mRNAs and the like) in an expression profile can be monitored. This can occur in various biological contexts, as disclosed herein, for example development of a disease and/or disorder, progression of a disease and/or disorder, and processes, such a cellular alterations associated with the disease and/or disorder.

The expression profiling methods described herein are also useful for ascertaining the effect of the expression of one or more nucleic acid sequences (e.g., genes, mRNAs and the like) on the expression of other nucleic acid sequences (e.g., genes, mRNAs and the like) in the same cell or in different cells. This provides, for example, for a selection of alternate molecular targets for therapeutic intervention if the ultimate or downstream target cannot be regulated.

The expression profiling methods described herein are also useful for ascertaining differential expression patterns of one or more nucleic acid sequences (e.g., genes, mRNAs and the like) in normal and abnormal cells. This provides a battery of nucleic acid sequences (e.g., genes, mRNAs and the like) that could serve as a molecular target for diagnosis or therapeutic intervention.

EXAMPLES

Starting Material: Purified genomic DNA and total RNA. For example, 50 ng gDNA and 50 ng total RNA was purified from THP-1 cell line. Ideally, the relative amount of gDNA and RNA should represent the content in the sample.

DNA/RNA Fragmentation:

|  | uL | final conc. |
|---|---|---|
| DNA/RNA sample | X |  |
| H$_2$O | 11.8 − x |  |
| 10× Fragmentation Buffer | 2 | 1× |
| 100 mM dATP | 0.6 | 3 mM |
| Exonuclease I (20 U/uL) | 1.6 | 1.6 U/uL |
| 5× Fragmentation Enzyme Mix | 4 | 1× |
|  | Total volume: 20 uL | |

Incubate in thermocycler with heated lid on for 4° C. 1 min → 32° C. 15 min → 75° C. 10 min → 80° C. 20 min → 4° C. hold RNA Polyadenylation:

|  | uL | final conc. |
|---|---|---|
| Sample from previous step | 20 |  |
| H$_2$O | 0.5 |  |
| 10 mM ATP | 1.25 | 0.5 mM |
| 10 mM 3'-dATP (blocker) | 1.25 | 0.5 mM |
| T4 Polynucleotide Kinase (10 U/uL) | 1 | 0.4 U/uL |
| E. coli Poly(A) Polymerase (5 U/uL) | 1 | 0.2 U/uL |
|  | Total volume: 25 uL | |

Incubate in thermocycler with heated lid on for 4° C. 1 min → 30° C. → 10 min 4° C. hold DNA Ligation:

|  | uL | final conc. |
|---|---|---|
| Sample from previous step | 25 |  |
| 5× Ligation Buffer | 10 | 1× |
| 50 uM DNA ligation Adaptor | 2.8 | 2.8 uM |
| 50% PEG-6000 | 7.2 | 7.2% |
| T4 DNA ligase (600 U/uL) | 5 | 60 U/uL |
|  | Total volume: 50 uL | |

Incubate in thermocycler with heated lid OFF for 4° C. 1 min → 20° C. 15 min → 4° C. hold Purification: Add 50 uL of ice cold water to the 50 uL sample from previous step to make 100 uL total. Do 2 rounds of 1.2× Ampure XP beads purification following manufacturer's manual with the following exceptions: 1st round elution in 52 uL water; and 2nd round elution in 13 uL water.

Reverse Transcription:

|  | uL | final conc. |
|---|---|---|
| Sample from previous step | 12.87 |  |
| 7.5 uM TSON10T18NV oligo | 1 | 300 nM |
| 25 uM TSON10forTS oligo | 1 | 1 uM |
| 5× SuperScript II Buffer | 5 | 1× |
| 25 mM each dNTP mix | 1 | 1 mM each |
| 0.1M DTT | 1.25 | 5 mM |
| RNase Inhibitor (40 U/uL) | 0.63 | 1 U/uL |
| 300 mM MgCl$_2$ | 0.5 | 6 mM |
| 150 mM MnCl$_2$ | 0.5 | 3 mM |
| MMLV Reverse Trancriptase RNase H− (200 U/uL) | 1.25 | 10 U/uL |
|  | Total volume: 25 uL | |

Incubate in thermocycler with heated lid on for 4° C. 1 min → 25° C. 10 min → 42° C. 45 min → 70° C. 15 min → 4° C. hold Purification: Add 75 uL of ice cold water to the 25 uL sample from previous step to make 100 uL total. Do 1 round of 1.2× Ampure XP beads purification following manufacturer's manual, and elute in 16.8 uL water.

Target Enrichment:

|  | uL | final conc. |
|---|---|---|
| Sample from previous step | 16.8 | |
| 5× V2 Buffer | 8 | 1× |
| 2 mM each dNTP mix | 4 | 0.2 mM each |
| 100 nM each SPE primer pool | 8 | 20 nM each |
| 10 uM DNA boosting primer | 0.8 | 400 nM |
| 10 uM RNA boosting primer | 0.8 | 400 nM |
| Hot-Star Taq Polymerase (6 U/uL) | 1.6 | 0.24 U/uL |
| | Total volume: 40 uL | |
| Incubate in thermocycler with heated lid on for 95° C. 13 min → 98° C. 2 min → 8 cycles of (98° C. 15 sec → 68° C. 10 min) → 72° C. 5 min → 4° C. hold | | |

Purification: Add 60 uL of ice cold water to the 40 uL sample from previous step to make 100 uL total. Do double size selection 0.5×/0.5× with Ampure XP beads following manufacturer's manual, and elute in 22 uL water.

qPCR (real-time) to determine final amplification cycles:

| | For DNA library | | For RNA library | |
|---|---|---|---|---|
| | uL | final conc. | uL | final conc. |
| Sample from previous step | 2 | | 2 | |
| 5× V2 Buffer | 2 | 1× | 2 | 1× |
| 2 mM each dNTP mix | 1 | 0.2 mM each | 1 | 0.2 mM each |
| H₂O | 2.1 | | 2.1 | |
| 20× EveGreen Dye | 0.5 | 1× | 0.5 | 1× |
| 4 uM IL2N5RS2 Universal primer | 1 | 400 nM | 1 | 400 nM |
| 4 uM DNA Universal Primer | 1 | 400 nM | 0 | 0 |
| 4 uM RNA Universal Primer | 0 | 0 | 1 | 400 nM |
| Hot-Star Taq Polymerase (6 U/uL) | 0.4 | 0.24 U/uL | 0.4 | 0.24 U/uL |
| | Total volume: 10 uL | | Total volume: 10 uL | |
| Run on ABI 7900 real time instrument: 95° C. 13 min → 98° C. 2 min → 30 cycles of (98° C. 15 sec → 62° C. 2 min). Record the counts for both samples | | | | |

Universal PCR:

| | For DNA library | | For RNA library | |
|---|---|---|---|---|
| | uL | final conc. | uL | final conc. |
| Sample from Target Enrichment | 9 | | 9 | |
| 5× V2 Buffer | 5 | 1× | 5 | 1× |
| 2 mM each dNTP mix | 2.5 | 0.2 mM each | 2.5 | 0.2 mM each |
| 4 uM IL2N5RS2 Universal primer | 2.5 | 400 nM | 2.5 | 400 nM |
| 4 uM DNA Universal Primer | 2.5 | 400 nM | 0 | 0 |
| 4 uM RNA Universal Primer | 0 | 0 | 2.5 | 400 nM |
| H₂O | 2.5 | | 2.5 | |
| Hot-Star Taq Polymerase (6 U/uL) | 1 | 0.24 U/uL | 1 | 0.24 U/uL |
| | Total volume: 25 uL | | Total volume: 25 uL | |
| Incubate in thermocycler with heated lid on for 95° C. 13 min → 98° C. 2 min → "X" cycles of (98° C. 15 sec → 62° C. 2 min) → 72° C. 5 min → 4° C. hold (X = Ct + 4) for DNA sample and RNA sample respectively. For example, if Ct = 19 for DNA, and 15 for RNA, then run 23 cycles for DNA, and 19 cycles for RNA | | | | |

Purification: Add 75 uL of ice cold water to each of the 25 uL sample from previous step to make 100 uL total. Do 1 round of 1.2× Ampure XP beads purification following manufacturer's manual, and elute in 20 uL water.

Library Quantification using Agilent Bioanalyzer High Sensitivity DNA chip: Dilute the purified libraries to 2 ng/uL. Load 1 uL of this diluted sample on the bioanalyzer. Obtain molar concentration of the libraries based on bionanlyzer's electropherogram. The libraries are ready for sequencing.

Following the workflow, with 50 ng gDNA and 50 ng total RNA input, we obtained 675 ng of DNA library and 455 ng of RNA library. The same amount of 50 ng total RNA was also used with QIAseq Targeted RNAscan Panels system from QIAGEN for comparison purpose. The same amount of 50 ng gDNA was also used with QIAseq Targeted DNA Panels system from QIAGEN for comparison purpose. The samples were then put on Illumina's MiSeq machine for sequencing.

Results:

As shown in Table 1, compared to the standalone RNA library prep workflow (QIAseq Targeted RNAscan Panels system from QIAGEN), our method achieved around 24% of its enrichment efficiency on the $1^{st}$ strand cDNA, and around 40% of its enrichment efficiency on the $2^{nd}$ strand cDNA. Since RNAscan workflow had strand bias toward the $1^{st}$ strand, our method had less bias and improved strand balance. The effect of enrichment efficiency on RNA analysis deserves further exploration.

TABLE 1

| Workflow | RNAScan | Ours |
|---|---|---|
| Average UMIs/primer $1^{st}$ strand | 11061 | 2681 |
| Average UMIs/primer $2^{nd}$ strand | 5279 | 2077 |
| Ratio $2^{nd}/1^{st}$ | 0.48 | 0.77 |

UMI per SPE primer for RNA sample: Primers were divided into two groups based on the RNA strand they detected. As shown in Table 2, compared to the standalone DNA library prep workflow (QIAseq Targeted DNA Panels system from QIAGEN), our method achieved slightly better enrichment efficiency. Both of the methods had comparable sequencing specificity and uniformity.

TABLE 2

| Workflow | Targeted DNA Panels | Ours |
|---|---|---|
| Average UMIs/primer | 1471 | 1701 |
| Average reads/UMI | 3.4 | 3.0 |
| Overall specificity (on-target reads/all reads) | 87% | 90% |
| Coverage uniformity (T50) | 24.9 | 21.6 |

Sequencing specs for DNA sample in both methods: Sequence coverage uniformity was measured by T50, the percentage of total sequence throughput captured by the bottom 50% of a target region. In the perfect uniform scenario, the T50 value equals to 50.

Cross talk between DNA and RNA was also evaluated since they remained in the same reaction. Using the same 50 ng of DNA and RNA from THP-1 cell line, the effective leaking signal from RNA to DNA was only 0.75% of the real DNA signal, as measured by the total UMIs of the primers detecting both RNA and DNA. In this case, only the extremely highly expressed genes might have an effect on corresponding DNA copy number analysis. However, if DNA copy number analysis was limited on intron regions, this effect should disappear. The effective leaking signal from DNA to RNA was around 3% on average by the same measurement. Since there were only a few copies of genome DNA in each cell in most cases, this kind of leaking could only affect those extremely low expressing genes (less than 0.1 copy per cell), which might be lower than the background noise level. In conclusion, our method demonstrated minimal cross talk between DNA and RNA samples which might not have any significant effect in real cases.

The DNA library prepared by our method can be used for DNA variant detection, and copy number analysis. The RNA library prepared by our method is suitable for gene expression analysis, fusion gene detection, and RNA variant detection. Multi-modal NGS panels can be developed based on our proposed method, and be used for biomarker screening, or targeted eQTL analysis.

Adaptor for ligation:

| Equal molar mix and annealing of the following 2 oligos to make double strand adaptor (DNA ligation Adaptor) | | |
|---|---|---|
| SEQ ID NO: 1 | /5Phos/GGACTCCAATACGCTAAG AAAGATCGGAAGAGCACACGTCTG/ 3ddC/ | PAGE Purified |
| SEQ ID NO: 2 | ATT+GGAG+TCC*T/3Phos/ | STD desalt |

Reverse Transcription Oligos:

| | | |
|---|---|---|
| SEQ ID NO: 3 TSON10T18 NV oligo | CGACTCACTATAGGGCTGGAATTCTGA CGNNNNNNNNNNNACGTTTTTTTTTTT TTTTTNV | PAGE Purified |
| SEQ ID NO: 4 TSON10for TS oligo | /5Me-isodC//iisodG//iisodG/ TAATACGACTCACTATAGGGCTGGAAT TCTGACGATCTGCrGrGrG | PAGE Purified |

Target Enrichment Oligos:

| | | |
|---|---|---|
| SEQ ID NO: 5 DNA boosting primer | AGCAGTGGTATCAACGCAGAGTCAAGC AGAAGACGGCATACGAGATTCCGAAAC GTGACTGGAGTTCAGACGTGTGCTCTT CCGATCTTTCTTAGCGT | STD desalt |
| SEQ ID NO: 6 RNA boosting primer | GTGAGTGATGGTTGAGGATGTGTGCAA GCAGAAGACGGCATACGAGATTACGTA CGGTGACTGGAGTTCAGACGTGTGCTC TTCCGATCTCGACTCACTATAGGGCTG GAATTCT | STD desalt |

For each primer, the first set of underlined nucleotides is priming site for PCR amplification in Universal PCR reactions, the second set of underlined nucleotides in the middle is the sample idx (index) region, which can be replaced with respective sample index sequences, and the third set of underlined nucleotides is part of DNA or RNA identifier used for PCR amplification in target enrichment reactions.

uPCR Primers:

| | | |
|---|---|---|
| SEQ ID NO: 7 IL2N5RS2 Universal primer | AATGATACGGCGACCACCGAGAT CTACACTCTTTCCCTACACGACG CTCTTCCGATCTNNNNNAATGTA CAGTATTGCGTTTTG | PAGE Purified |
| SEQ ID NO: 8 DNA Universal Primer | AAGCAGTGGTATCAACGCAGAGT | STD desalt |
| SEQ ID NO: 9 RNA Universal Primer | GTGAGTGATGGTTGAGGATGTGT G | STD desalt |

SPE Primer Pool (equal molar mix of the following oligos):

SEQ ID NO: 10
AATGTACAGTATTGCGTTTTGAGCCCCAAGTCCTATGAGAACCTCTG

SEQ ID NO: 11
AATGTACAGTATTGCGTTTTGTGGCACCAGCGATCAGGTCCTTTAT

SEQ ID NO: 12
AATGTACAGTATTGCGTTTTGCTGAGTGGAGTCACAGCGGAGATAGT

SEQ ID NO: 13
AATGTACAGTATTGCGTTTTGTGTTCCACCAGTAACAACAGTTGAATGTCC

SEQ ID NO: 14
AATGTACAGTATTGCGTTTTGGTGTGAGGAACATACTAGTGCTTTGCAAGT

SEQ ID NO: 15
AATGTACAGTATTGCGTTTTGTTCAAAGTTGGGTCTGCTTCAGTCCAAAG

SEQ ID NO: 16
AATGTACAGTATTGCGTTTTGCCCCCAGCTTCTTCTCTCTGCACTAAG

SEQ ID NO: 17
AATGTACAGTATTGCGTTTTGGCCTTCCCAACATGCATTCTAACTTCTTCC

SEQ ID NO: 18
AATGTACAGTATTGCGTTTTGCCAGCTACTCTCAAAATCAGCATCCTTTGG

SEQ ID NO: 19
AATGTACAGTATTGCGTTTTGCCAGTCCTTCTGTGAGTCTATCCTCAGTTC

SEQ ID NO: 20
AATGTACAGTATTGCGTTTTGAGAGCGAACCAAGAATGCCTGTTTACAG

SEQ ID NO: 21
AATGTACAGTATTGCGTTTTGGAGAGGCACGAGAACACACATCTATTCTG

SEQ ID NO: 22
AATGTACAGTATTGCGTTTTGTTCTCTTCAGAAGTTCCTTCGTCATCCTT

SEQ ID NO: 23
AATGTACAGTATTGCGTTTTGTGATGACATGCCCCATCACTAAAACAC

SEQ ID NO: 24
AATGTACAGTATTGCGTTTTGTGATAGAGACATGATGTAACCGTGGGAATTTCTTC

SEQ ID NO: 25
AATGTACAGTATTGCGTTTTGCGTTCTAAGAGAGTGACAGAAAGGTAAAGAGGAG

SEQ ID NO: 26
AATGTACAGTATTGCGTTTTGATCACAAAGTATCTTTTTCTGTGGCTTAGAAATCTT

-continued

SEQ ID NO: 27
AATGTACAGTATTGCGTTTTGTCAAATGTTAGCTCATTTTTGTTAATGGT
GGCTTTT

SEQ ID NO: 28
AATGTACAGTATTGCGTTTTGTGTCACATTATAAAGATTCAGGCAATGTT
TGTTAGT

SEQ ID NO: 29
AATGTACAGTATTGCGTTTTGAGTTTGTATGCAACATTTCTAAAGTTACC
TACTTGT

SEQ ID NO: 30
AATGTACAGTATTGCGTTTTGAAAATCTGTTTTCCAATAAATTCTCAGAT
CCAGGAA

SEQ ID NO: 31
AATGTACAGTATTGCGTTTTGCGACCCAGTTACCATAGCAATTTAGTGAA
ATAACTA

SEQ ID NO: 32
AATGTACAGTATTGCGTTTTGAGAGGCGCTATGTGTATTATTATAGCTAC
CTGTTAA

SEQ ID NO: 33
AATGTACAGTATTGCGTTTTGCGTTTTTGACAGTTTGACAGTTAAAGGCA
TTTCC

SEQ ID NO: 34
AATGTACAGTATTGCGTTTTGCTGTCCTTATTTTGGATATTTCTCCCAAT
GAAAGTA

SEQ ID NO: 35
AATGTACAGTATTGCGTTTTGGACTTTTTGCAAATGTTTAACATAGGTGA
CAGATTT

SEQ ID NO: 36
AATGTACAGTATTGCGTTTTGAAGTAGAAAATGGAAGTCTATGTGATCAA
GAAATCG

SEQ ID NO: 37
AATGTACAGTATTGCGTTTTGGGCCTCTTAAAGATCATGTTTGTTACAGT
GCTTA

SEQ ID NO: 38
AATGTACAGTATTGCGTTTTGACAAGATTGGTCAGGAAAAGAGAATTGTT
CCTATAA

SEQ ID NO: 39
AATGTACAGTATTGCGTTTTGAGACCCTGTCTCAAAAGTAAAAGTAAGT
TAACATG

SEQ ID NO: 40
AATGTACAGTATTGCGTTTTGTCAGTGTCTTCCAAATCCTTATGTATAGC
AGCAAT

SEQ ID NO: 41
AATGTACAGTATTGCGTTTTGAGGGTCGAGGAAGCCAGTTTACATCAA

SEQ ID NO: 42
AATGTACAGTATTGCGTTTTGAACAAAAGATATTTTCAATATTTCTGCG
CAGGTTT

SEQ ID NO: 43
AATGTACAGTATTGCGTTTTGGTCTCGACTTGAATTGCAAAAGATGTTA
GAAAAGC

SEQ ID NO: 44
AATGTACAGTATTGCGTTTTGAAAATGTTGGCAGTCATAACATTTGAAAC
TAATGGA

SEQ ID NO: 45
AATGTACAGTATTGCGTTTTGAGCCTCAAACAGGTTGGTTTTAAATTTGA
AGTCT

SEQ ID NO: 46
AATGTACAGTATTGCGTTTTGCCTCTGTGTGTATGTTTTAACTACAAAGC
GAAACA

SEQ ID NO: 47
AATGTACAGTATTGCGTTTTGGATTCACCTGGTAATGAGGAAAACAGCTT
TAAAATC

SEQ ID NO: 48
AATGTACAGTATTGCGTTTTGAGATCTGCTGAAAAGAAATTTGTTAAAGC
ACAATT

SEQ ID NO: 49
AATGTACAGTATTGCGTTTTGCGGCATCCCCTACATCGAGACCTC

SEQ ID NO: 50
AATGTACAGTATTGCGTTTTGCAGGGAGCAGATCAAACGGGTGAAG

SEQ ID NO: 51
AATGTACAGTATTGCGTTTTGCAAGTCTTTTGAGGACATCCACCAGTACA
G

SEQ ID NO: 52
AATGTACAGTATTGCGTTTTGACGTGCCTGTTGGACATCCTGGATA

SEQ ID NO: 53
AATGTACAGTATTGCGTTTTGCCTGTACTGGTGGATGTCCTCAAAAGACT

SEQ ID NO: 54
AATGTACAGTATTGCGTTTTGCCCTGAGGAGCGATGACGGAATATAAGC

SEQ ID NO: 55
AATGTACAGTATTGCGTTTTGGTCGTATTCGTCCACAAAATGGTTCTGGA
TC

SEQ ID NO: 56
AATGTACAGTATTGCGTTTTGTGACTGGCAATTGTGTCAACAGGTGAAAA

SEQ ID NO: 57
AATGTACAGTATTGCGTTTTGCGCCAGCTGGAGTTTGGTCATGTTT

SEQ ID NO: 58
AATGTACAGTATTGCGTTTTGAATCCCTCTCATCACAATTTCATTCCACA
ATAGTTT

SEQ ID NO: 59
AATGTACAGTATTGCGTTTTGTCAACAACAAAGAGAATCATGAAATCAAC
CCTAGC

SEQ ID NO: 60
AATGTACAGTATTGCGTTTTGGATATGGAGCCAGCGTGTTCCGATT

SEQ ID NO: 61
AATGTACAGTATTGCGTTTTGGGCGCGGAAAGTCCTCACTCTC

SEQ ID NO: 62
AATGTACAGTATTGCGTTTTGTATGGTGAGGTTCGGCGTGTTTAAACG

SEQ ID NO: 63
AATGTACAGTATTGCGTTTTGTGGTGACAAAGTTAGAAGGGTCCATGG

SEQ ID NO: 64
AATGTACAGTATTGCGTTTTGCTTCTTTACCACCCCAGATACGACGACTA

SEQ ID NO: 65
AATGTACAGTATTGCGTTTTGCGCTCGTGGTGGTAGTCGTCGTAT

SEQ ID NO: 66
AATGTACAGTATTGCGTTTTGCCAGGAGGCCCTTTCTGTTTACAACC

SEQ ID NO: 67
AATGTACAGTATTGCGTTTTGCCCACAAGCCCAAAATATTCTACTCACTT
TGC

SEQ ID NO: 68
AATGTACAGTATTGCGTTTTGATCGCCTGCATCAAGGAAAAGGTAATGG

SEQ ID NO: 69
AATGTACAGTATTGCGTTTTGCGCGTAAGGATAGCAACTGAGGTTATCAC

SEQ ID NO: 70
AATGTACAGTATTGCGTTTTGCGACCTGACGTAACCCCTTGCTTATC

SEQ ID NO: 71
AATGTACAGTATTGCGTTTTGGGAAATGCTCTCACGTAGTCTCTCATGTC
T

SEQ ID NO: 72
AATGTACAGTATTGCGTTTTGGTCATAACCCGAAGAACAATGTTGCCACT
A

SEQ ID NO: 73
AATGTACAGTATTGCGTTTTGGTCAGCTCAGGATAAAGCACGGATGGATA

SEQ ID NO: 74
AATGTACAGTATTGCGTTTTGCTCAGGATAAAAGCTTCCTTCTTAACAAG
TTTTTCC

SEQ ID NO: 75
AATGTACAGTATTGCGTTTTGAGAGATTGTTCCCTTGCATTGACCTCTTT
TTC

SEQ ID NO: 76
AATGTACAGTATTGCGTTTTGCCCCTCACCTTTGGAATTTACAGTCTGAA

SEQ ID NO: 77
AATGTACAGTATTGCGTTTTGTAGGTTCTTCAGGTCTCTACACTCTCCTT
TAAACT

SEQ ID NO: 78
AATGTACAGTATTGCGTTTTGGAGAAGGAGTGCAATGCCAAGATTATGAT
CC

SEQ ID NO: 79
AATGTACAGTATTGCGTTTTGGACGTTCTCCATTGTATTGGCAGTAACCA

SEQ ID NO: 80
AATGTACAGTATTGCGTTTTGCACATCTCACAGGCTCTAAAGGAATTCTA
TATCCTA

SEQ ID NO: 81
AATGTACAGTATTGCGTTTTGGAGGCAAGAGGTGAGTAGTACCAATACTG
TC

SEQ ID NO: 82
AATGTACAGTATTGCGTTTTGGAGCCCCTCCGCTTACTTGTAATCTG

SEQ ID NO: 83
AATGTACAGTATTGCGTTTTGCCAGTAAAACGTATTGAGAAAAAGGTAAA
AGCGTTA

SEQ ID NO: 84
AATGTACAGTATTGCGTTTTGGCTCAGAATAAATCGTAACAATCTCAAAG
TGCATTT

SEQ ID NO: 85
AATGTACAGTATTGCGTTTTGTGAGGTGTCCACAGGGCTCAATCTTTAC

SEQ ID NO: 86
AATGTACAGTATTGCGTTTTGCCCCTTGTATCAGTAAAGGCTATATAATA
CCGAATT

SEQ ID NO: 87
AATGTACAGTATTGCGTTTTGTCATGAAGAGAGTATCATCAGCTCGTTCA
TCATC

SEQ ID NO: 88
AATGTACAGTATTGCGTTTTGTGTCCTTTCTGCCGATGTGAAATTAAAGG
TAC

SEQ ID NO: 89
AATGTACAGTATTGCGTTTTGTCGCCCCAAATAATTTCCTGCGAACA

SEQ ID NO: 90
AATGTACAGTATTGCGTTTTGCTCATACCTCCATTCCAAGCTTTCATTGT
CTC

SEQ ID NO: 91
AATGTACAGTATTGCGTTTTGCCTGCCCTTATTTTTAACAGCAGGAACGA
AT

SEQ ID NO: 92
AATGTACAGTATTGCGTTTTGTCGATAGCGAAAGTCCTCTTTGGTCAG

SEQ ID NO: 93
AATGTACAGTATTGCGTTTTGGTTAAAGACCAACCACTAACTAAGAGACT
TTCCAAG

SEQ ID NO: 94
AATGTACAGTATTGCGTTTTGAAACCTCTTCCAGTACCTTCTTCATGGTT
CT

SEQ ID NO: 95
AATGTACAGTATTGCGTTTTGTTTCCAGGTGATGTGCTCTATGAACTCCT
T

SEQ ID NO: 96
AATGTACAGTATTGCGTTTTGGGAGCGGTGCAACAGTTCAATGGT

SEQ ID NO: 97
AATGTACAGTATTGCGTTTTGCATCCGTGGATAATGTGCACCATAACC

SEQ ID NO: 98
AATGTACAGTATTGCGTTTTGTCGGAGAGCCTGGACTGTTTGAAATC

SEQ ID NO: 99
AATGTACAGTATTGCGTTTTGAAGCCAGGTCTTCCCGATGAGAGAG

SEQ ID NO: 100
AATGTACAGTATTGCGTTTTGGGCACTCCGTGGATTTCAAACAGTC

SEQ ID NO: 101
AATGTACAGTATTGCGTTTTGCAGATATCTGCTGCCCTTTTACCTTATGG
TTT

SEQ ID NO: 102
AATGTACAGTATTGCGTTTTGTGTAGACTGCTTTGGGATTACGTCTATCAGTTG

SEQ ID NO: 103
AATGTACAGTATTGCGTTTTGGGAAAGGAGAAAAAGGAAGTGCTACCTGAAC

SEQ ID NO: 104
AATGTACAGTATTGCGTTTTGTTTTTCTCCCTTCCTCCTTTGAACAAACAG

SEQ ID NO: 105
AATGTACAGTATTGCGTTTTGACAGCTTTAGGAAAATGGAATCTCTTACCTCCTC

SEQ ID NO: 106
AATGTACAGTATTGCGTTTTGGGGTGTTATGGTCGCGTTGGATTTCTG

SEQ ID NO: 107
AATGTACAGTATTGCGTTTTGGCTACGGCGTGCAACTCACAGAAC

SEQ ID NO: 108
AATGTACAGTATTGCGTTTTGACCGACCTCTTCCAGCGCTACTT

SEQ ID NO: 109
AATGTACAGTATTGCGTTTTGCGGGCAGGGCTTACTTACCTTGG

SEQ ID NO: 110
AATGTACAGTATTGCGTTTTGTAGCTACTGCCTGCCTTCGAAGAACGAT

SEQ ID NO: 111
AATGTACAGTATTGCGTTTTGTGTGGGTGGAAAAAGATGTGGTTAAGAAACAAC

SEQ ID NO: 112
AATGTACAGTATTGCGTTTTGCCCCCATATAGCTTAATCTGATGGGCATC

SEQ ID NO: 113
AATGTACAGTATTGCGTTTTGGAAAGAGCATCAGGAACAAGCCTTGAGTAC

SEQ ID NO: 114
AATGTACAGTATTGCGTTTTGTTGAGATGCCTGACAACCTTTACACCTTTG

SEQ ID NO: 115
AATGTACAGTATTGCGTTTTGCTCTAGGGCTGAGGGAATATGCATCTCT

SEQ ID NO: 116
AATGTACAGTATTGCGTTTTGCGTACCCAGAAGACAATGGCCTAGCTAT

SEQ ID NO: 117
AATGTACAGTATTGCGTTTTGGGGCAGCACAGATTCCCTTAACCA

SEQ ID NO: 118
AATGTACAGTATTGCGTTTTGCCATACCTTGGCTATCCCCTGAAAGTTG

SEQ ID NO: 119
AATGTACAGTATTGCGTTTTGGCCCTGATGCTCATGGAGTGTTCCT

SEQ ID NO: 120
AATGTACAGTATTGCGTTTTGCCTGGTGGTTGGGAGACGACTAC

SEQ ID NO: 121
AATGTACAGTATTGCGTTTTGTGCTGACAGGACACAGAACAAGATACCT

SEQ ID NO: 122
AATGTACAGTATTGCGTTTTGGGTACAGGTATCTTGTTCTGTGTCCTGTCAG

SEQ ID NO: 123
AATGTACAGTATTGCGTTTTGGAGTCCCGGGCTCGATTCACAG

SEQ ID NO: 124
AATGTACAGTATTGCGTTTTGCTGGTCAGAGAGGTGTGTACTGATTGTCT

SEQ ID NO: 125
AATGTACAGTATTGCGTTTTGAGGAAAGATCAATTACATTCACAAGTTCACACTTCT

SEQ ID NO: 126
AATGTACAGTATTGCGTTTTGCTGCACAGTTCAGAGGATATTTAAGCTCAATGAC

SEQ ID NO: 127
AATGTACAGTATTGCGTTTTGCACAGACCGTCATGCATTTCTGACACTC

SEQ ID NO: 128
AATGTACAGTATTGCGTTTTGAGGCTGGTACCTGCTCTTCTTCAATC

SEQ ID NO: 129
AATGTACAGTATTGCGTTTTGCGAAATCAAACAGTTGTCTATCAGAGCCTGTC

SEQ ID NO: 130
AATGTACAGTATTGCGTTTTGACAAAAGAAAAGAAGTCATGTCTGTATGTGGAAA

SEQ ID NO: 131
AATGTACAGTATTGCGTTTTGTCCAGGATAATACACATCACAGTAAATAACACTCTG

SEQ ID NO: 132
AATGTACAGTATTGCGTTTTGCATCCTCTTTGTCATCAAGCTACAGTCTTTTTGA

SEQ ID NO: 133
AATGTACAGTATTGCGTTTTGCTCCCATTTTTGTGCATCTTTGTTGCTGTC

SEQ ID NO: 134
AATGTACAGTATTGCGTTTTGCAGAACTGCCTATTCCTAACTGACTCATCATTTC

SEQ ID NO: 135
AATGTACAGTATTGCGTTTTGGAATTCTGTTTCATCGCTGAGTGACACTCTTTT

SEQ ID NO: 136
AATGTACAGTATTGCGTTTTGTTTTTACCTTTGCTTTTACCTTTTTGTACTTGTGAC

SEQ ID NO: 137
AATGTACAGTATTGCGTTTTGAGAAGGAGTCTGGAATAGAAAGGCTAACAGAA

SEQ ID NO: 138
AATGTACAGTATTGCGTTTTGCACAAGATGTGCCAAGGGAATTGTATGC

SEQ ID NO: 139
AATGTACAGTATTGCGTTTTGAAGAGTCAATAGGTCAGAGAGTTTTATGTTCTTCCA

SEQ ID NO: 140
AATGTACAGTATTGCGTTTTGACTGATCTTCTCAAAGTCGTCATCCTTCAGT

SEQ ID NO: 141
AATGTACAGTATTGCGTTTTGACCCTGAGAAATAATCCAATTACCTGTTAATCAAGG

SEQ ID NO: 142
AATGTACAGTATTGCGTTTTGAAAAGGTATTGAGTAAAATCAGTCTTCCTTCTACCC

SEQ ID NO: 143
AATGTACAGTATTGCGTTTTGCCTTCCTCCCTCTTTCTTTCATAAAACCTCTCTT

SEQ ID NO: 144
AATGTACAGTATTGCGTTTTGGCCAGAGCCACCCAACTCTTAAGG

SEQ ID NO: 145
AATGTACAGTATTGCGTTTTGTGGAAGAGGAATTTAATAACGAACGTTTTAAGAGGA

SEQ ID NO: 146
AATGTACAGTATTGCGTTTTGGCATCTACTGCCGAGGATGTTCCAAG

SEQ ID NO: 147
AATGTACAGTATTGCGTTTTGCACAGTGAGCTCAAGTGCGACATCA

SEQ ID NO: 148
AATGTACAGTATTGCGTTTTGCCGACTGGCCATCTCCTCGTAG

SEQ ID NO: 149
AATGTACAGTATTGCGTTTTGGTACCAGCGCGACTACGAGGAGAT

SEQ ID NO: 150
AATGTACAGTATTGCGTTTTGTCTTTTCTGTCAAATGGAGATGATCTCTTCTGACTC

SEQ ID NO: 151
AATGTACAGTATTGCGTTTTGGGGAGCCCATCATCTGCAAAAACATCC

SEQ ID NO: 152
AATGTACAGTATTGCGTTTTGAAGCTGAAGAAGATGTGGAAAAGTCCCAATG

SEQ ID NO: 153
AATGTACAGTATTGCGTTTTGGCGTGGGATGTTTTTGCAGATGATGG

SEQ ID NO: 154
AATGTACAGTATTGCGTTTTGCGACGCTGAGGACGCTATGGATG

SEQ ID NO: 155
AATGTACAGTATTGCGTTTTGGCTGAGGCGCGTCTTCGAGAAG

SEQ ID NO: 156
AATGTACAGTATTGCGTTTTGGCGCTTGTCGTGAAAGCGAACGA

SEQ ID NO: 157
AATGTACAGTATTGCGTTTTGGCTGCCCGCCCAGTTGTTACT

SEQ ID NO: 158
AATGTACAGTATTGCGTTTTGAGACTCTGGACTGATGAAGCAATTCTGAGT

SEQ ID NO: 159
AATGTACAGTATTGCGTTTTGTCACCGGTGACACCTTAAAACCAAAGC

SEQ ID NO: 160
AATGTACAGTATTGCGTTTTGGGCTCCTTTGTACCTCCTCCATCTTGATC

SEQ ID NO: 161
AATGTACAGTATTGCGTTTTGGTCAGTTGTCTAACAATAACAAAGATCTGCTCTTGG

SEQ ID NO: 162
AATGTACAGTATTGCGTTTTGGGTGGGCAGCAAGAAAAAGTCCAGTAAA

SEQ ID NO: 163
AATGTACAGTATTGCGTTTTGGCCAAGGCTTTCTCTGGCATGATCTTTT

SEQ ID NO: 164
AATGTACAGTATTGCGTTTTGGGATAACTTTCTCAGCATTTCCACCAGTTTCAAG

SEQ ID NO: 165
AATGTACAGTATTGCGTTTTGTGTCCCTAAGTTGAGTAAAATGATAGAGAATGAGTC

SEQ ID NO: 166
AATGTACAGTATTGCGTTTTGGCTGCCAGAAATCCAGCATCCAAAATTTG

SEQ ID NO: 167
AATGTACAGTATTGCGTTTTGGTCGCTTTCTTTTCTTAGTGCCAGGAAACT

SEQ ID NO: 168
AATGTACAGTATTGCGTTTTGACAGTCGAGACGATTCATGAGGGAACTTC

SEQ ID NO: 169
AATGTACAGTATTGCGTTTTGGGAAAGCTCGGCGTGTTGGATAAGAAG

SEQ ID NO: 170
AATGTACAGTATTGCGTTTTGACGCCACAAGTGACTGAAAGTTGGAAG

SEQ ID NO: 171
AATGTACAGTATTGCGTTTTGTGATGGGCTGGAGATTTGGCATAGTTTTC

SEQ ID NO: 172
AATGTACAGTATTGCGTTTTGCTATGCACCCACTTTCAACACAGTTAGGT

SEQ ID NO: 173
AATGTACAGTATTGCGTTTTGGCTTGGTCAGAAGTGCTGTTGTTGTC

SEQ ID NO: 174
AATGTACAGTATTGCGTTTTGCGTGGGCCAGAAAGTTGTCCACAATG

SEQ ID NO: 175
AATGTACAGTATTGCGTTTTGGGGATATGGATTCTCGTGGTAGAAGGTGTAA

SEQ ID NO: 176
AATGTACAGTATTGCGTTTTGCTAATCACCAAGTTCCAAGTGTTCAGAATCTCC

SEQ ID NO: 177
AATGTACAGTATTGCGTTTTGACCGTAATAACCAAGGTTCATCATAGGCATTGAT

SEQ ID NO: 178
AATGTACAGTATTGCGTTTTGTCCCAGTGGAAGTTACTATGCACCCTAT

SEQ ID NO: 179
AATGTACAGTATTGCGTTTTGTGCTTATGCTTGTGTTTGTGTTTCCTCTTATGG

SEQ ID NO: 180
AATGTACAGTATTGCGTTTTGGCTTCTGTTTCTCCTTATGCTTGTTCTTCTCAC

SEQ ID NO: 181
AATGTACAGTATTGCGTTTTGCCTGAGTGGTCTTTTTGCAGGCAAAG

SEQ ID NO: 182
AATGTACAGTATTGCGTTTTGCCGGCCACAAAGCTTCTAAGAACAAC

SEQ ID NO: 183
AATGTACAGTATTGCGTTTTGGCGGTTCATCTTGAAGGCTTGGATGT

-continued

SEQ ID NO: 184
AATGTACAGTATTGCGTTTTGTTCAGTGAAATGAACCCTTCGAATGACAA
G

SEQ ID NO: 185
AATGTACAGTATTGCGTTTTGCTCCTCCTCCTCTTTGCGTTTCTTGTC

SEQ ID NO: 186
AATGTACAGTATTGCGTTTTGGCAGCAGAGAAACAAATGAAGGACAAACA
G

SEQ ID NO: 187
AATGTACAGTATTGCGTTTTGTAAGGAGGAGGAAGAAGACAAGAAACGCA
AA

SEQ ID NO: 188
AATGTACAGTATTGCGTTTTGTAAGGCAGGTCTGTGAGCACAAAATTTGG

SEQ ID NO: 189
AATGTACAGTATTGCGTTTTGTGGAGCTGACCAGTGACAATGACC

SEQ ID NO: 190
AATGTACAGTATTGCGTTTTGGGCCAAGAAGTCGGTGGACAAGAAC

SEQ ID NO: 191
AATGTACAGTATTGCGTTTTGGCGCAGGCGGTCATTGTCACTG

SEQ ID NO: 192
AATGTACAGTATTGCGTTTTGTTGCTGTTCTTGTCCACCGACTTCTTG

SEQ ID NO: 193
AATGTACAGTATTGCGTTTTGGCAGTGCGCGATCTGGAACTG

SEQ ID NO: 194
AATGTACAGTATTGCGTTTTGCGGCGGCGACTTTGACTACCC

SEQ ID NO: 195
AATGTACAGTATTGCGTTTTGGAGCACGAGACGTCCATCGACATC

SEQ ID NO: 196
AATGTACAGTATTGCGTTTTGCGGCCAGGAACTCGTCGTTGAA

SEQ ID NO: 197
AATGTACAGTATTGCGTTTTGGCCATGCCGGGAGAACTCTAACTC

SEQ ID NO: 198
AATGTACAGTATTGCGTTTTGTGTAACCCTCCTAAGTGTTCATACGTTGT
CTTG

SEQ ID NO: 199
AATGTACAGTATTGCGTTTTGGTCTTGGTCTCTGTTATATCTTGAGTCTA
GAACAGT

SEQ ID NO: 200
AATGTACAGTATTGCGTTTTGCAGGAGAACATGGAGGCGAGAAGAAAAT

SEQ ID NO: 201
AATGTACAGTATTGCGTTTTGGGGAAAGATTGGATGCCGGGAATCAAC

SEQ ID NO: 202
AATGTACAGTATTGCGTTTTGCGGAGGCTTGATTAGGTAGGAGGTG

SEQ ID NO: 203
AATGTACAGTATTGCGTTTTGGCGGCAGCTCAACGAGAATAAACA

SEQ ID NO: 204
AATGTACAGTATTGCGTTTTGGCCCGCATCCTTACTCCGCTTATC

SEQ ID NO: 205
AATGTACAGTATTGCGTTTTGGCTGGTTTCAAGGTAAGTGGACTCTTCC

SEQ ID NO: 206
AATGTACAGTATTGCGTTTTGGGGAATGACTGACGGAGAATCCCAAC

SEQ ID NO: 207
AATGTACAGTATTGCGTTTTGCTAAGACCGAGAGCCTGTAGGAGCTTT

-continued

SEQ ID NO: 208
AATGTACAGTATTGCGTTTTGGCCGGGCTTGTCTGGTCATCT

SEQ ID NO: 209
AATGTACAGTATTGCGTTTTGCAGCTCACCTCCAAAAAGGCAAAATTCTT
G

SEQ ID NO: 210
AATGTACAGTATTGCGTTTTGGCAGGAGGCCATGATGGATTTCTTCAA

SEQ ID NO: 211
AATGTACAGTATTGCGTTTTGCATGAGTGAAAGGAAAGAGGAAATCCCAA
TCC

SEQ ID NO: 212
AATGTACAGTATTGCGTTTTGCCTATCTTCCACAGTACTTACACAACTTC
CTAAGC

SEQ ID NO: 213
AATGTACAGTATTGCGTTTTGCTCGCCGTAGACTGTCCAGGTTTT

SEQ ID NO: 214
AATGTACAGTATTGCGTTTTGCTCACCTGATCCGTGACGTTGATGTC

SEQ ID NO: 215
AATGTACAGTATTGCGTTTTGGCCCTGATGGACTCTCGGCTACT

SEQ ID NO: 216
AATGTACAGTATTGCGTTTTGGAGAAAGATCAGGAACACTTGTCCCCTAC
TAG

SEQ ID NO: 217
AATGTACAGTATTGCGTTTTGGTCCTCCACGATCTCCTCATACTCCTC

SEQ ID NO: 218
AATGTACAGTATTGCGTTTTGTCGATGGACTTGACAAGCCCGTACTT

SEQ ID NO: 219
AATGTACAGTATTGCGTTTTGCTGGACGACGAGGAGTATGAGGAGATC

SEQ ID NO: 220
AATGTACAGTATTGCGTTTTGTACCAGAAGTCCCGGCGGTGATAAG

SEQ ID NO: 221
AATGTACAGTATTGCGTTTTGGTTCACCTCTGTGTTTGACTGCCAGAAA

SEQ ID NO: 222
AATGTACAGTATTGCGTTTTGCAATGAGTATTCTCTTCATTTCAGGTCAG
TTGATTT

SEQ ID NO: 223
AATGTACAGTATTGCGTTTTGGGCTGCTTTCTTGAAGGCTATTGGGTAT

SEQ ID NO: 224
AATGTACAGTATTGCGTTTTGAGGAGACTGGAATTCTCGAATAAGGATTA
ACA

SEQ ID NO: 225
AATGTACAGTATTGCGTTTTGGCATAGTTAAAACCTGTGTTTGGTTTTGT
AGGTCTT

SEQ ID NO: 226
AATGTACAGTATTGCGTTTTGCTCTGTGTTGGCGGATACCCTTCCATA

SEQ ID NO: 227
AATGTACAGTATTGCGTTTTGGGCATTCCTTCTTTATTGCCCTTCTTAAA
AGC

SEQ ID NO: 228
AATGTACAGTATTGCGTTTTGGCTGCTGGTCTGGCTACTATGATCTCTAC

```
                                                         SEQ ID NO: 229
AATGTACAGTATTGCGTTTTGGCACACAGCTTTTAAGAAGGGCAATAAAG

AAG
                                                         SEQ ID NO: 230
AATGTACAGTATTGCGTTTTGTGTATGTTTAATTCTGTACATGAGCATTT

CATCAGT
                                                         SEQ ID NO: 231
AATGTACAGTATTGCGTTTTGATTTCATACCTTGCTTAATGGGTGTAGAT

ACCAAAA
                                                         SEQ ID NO: 232
AATGTACAGTATTGCGTTTTGTTGGCGTCAAATGTGCCACTATCACTC

SEQ ID NO: 233
AATGTACAGTATTGCGTTTTGTTCTCTTTCAAGCTATGATTTAGGCATAG

AGAATCG
                                                         SEQ ID NO: 234
AATGTACAGTATTGCGTTTTGCTGCAGTTGTAGGTTATAACTATCCATTT

GTCTGAA
                                                         SEQ ID NO: 235
AATGTACAGTATTGCGTTTTGCCCTAGGTCAGATCACCCAGTCAGTTAAA

AC
                                                         SEQ ID NO: 236
AATGTACAGTATTGCGTTTTGTGGTTAAAGGTCAGCCCACTTACCAGATA

TG
                                                         SEQ ID NO: 237
AATGTACAGTATTGCGTTTTGGGGTATGCTCCCCATTTAGAGGATAAGG

SEQ ID NO: 238
AATGTACAGTATTGCGTTTTGACGTCAGATCTACAGCGAACACAACTACT

SEQ ID NO: 239
AATGTACAGTATTGCGTTTTGAGTGGTGCCAGACTCACATTCAGTTCTAA

SEQ ID NO: 240
AATGTACAGTATTGCGTTTTGCTTGGCCAGTTCCTTTCTCTAATGTATCA

TCTC
                                                         SEQ ID NO: 241
AATGTACAGTATTGCGTTTTGAAGTTTTCTTGTCTAGTATCACTTTCCCT

CATAGG
                                                         SEQ ID NO: 242
AATGTACAGTATTGCGTTTTGGGGCTCAACAGATGGTATGTGTTCTCTG

SEQ ID NO: 243
AATGTACAGTATTGCGTTTTGGCTCTCGTTTCTAACAGTTCTTTGCATTG

GATA
                                                         SEQ ID NO: 244
AATGTACAGTATTGCGTTTTGGAGGTGACCTTCAAAGTCAGAGGCTGTAT

SEQ ID NO: 245
AATGTACAGTATTGCGTTTTGGAGCAACCATCCCATCTGTCCTTGTAAC

SEQ ID NO: 246
AATGTACAGTATTGCGTTTTGGGACAAGGATGAGAAACCCAATTGGAACC

SEQ ID NO: 247
AATGTACAGTATTGCGTTTTGCGGTCCGCCAAAAGATCCCAGATTC

SEQ ID NO: 248
AATGTACAGTATTGCGTTTTGGGAGGCCACTAACCCACTTGTGATG

SEQ ID NO: 249
AATGTACAGTATTGCGTTTTGTCCAGTTTCCTAGAGGATGTAATGGGATT

TGTC
                                                         SEQ ID NO: 250
AATGTACAGTATTGCGTTTTGTCACATTTGGAGATGAGAAACGAGGTGTT

CT
                                                         SEQ ID NO: 251
AATGTACAGTATTGCGTTTTGCCCTTGGCCTGTAACATTGCTCTGATC

SEQ ID NO: 252
AATGTACAGTATTGCGTTTTGCACCTCGTTTCTCATCTCCAAATGTGATC

TC
                                                         SEQ ID NO: 253
AATGTACAGTATTGCGTTTTGCCAGTAGCTTTCCTGTTCTCGGCATT

SEQ ID NO: 254
AATGTACAGTATTGCGTTTTGGCAGCGTCAAGAATGAGAAGACTTTTGTG

SEQ ID NO: 255
AATGTACAGTATTGCGTTTTGTTGCCCTTCTGGAAATTACCCCGAGA

SEQ ID NO: 256
AATGTACAGTATTGCGTTTTGAGTTCCACCAGCTTTAATTATTCCTCTAG

CTCTC
                                                         SEQ ID NO: 257
AATGTACAGTATTGCGTTTTGGTTTCCCATGGCCATAATTTATTATCTCA

CCACAA
                                                         SEQ ID NO: 258
AATGTACAGTATTGCGTTTTGGTCACGATGACTGTATTGGACCCTCAA

SEQ ID NO: 259
AATGTACAGTATTGCGTTTTGTCCAGACCTTTGCTTTAGATTGGCAATTA

TTACTG
                                                         SEQ ID NO: 260
AATGTACAGTATTGCGTTTTGCCCTAACAACACAGAAGCAAAGCGTTCTT

T
                                                         SEQ ID NO: 261
AATGTACAGTATTGCGTTTTGCGCCCTCCTACCACCTGTACTACG

SEQ ID NO: 262
AATGTACAGTATTGCGTTTTGACTATCCAGGCGCCTTCACCTACTC

SEQ ID NO: 263
AATGTACAGTATTGCGTTTTGCTCCTAGGCGGTATCATCCTGGGTAG

SEQ ID NO: 264
AATGTACAGTATTGCGTTTTGTCTGATTCTCTTCAGATACAAGGCAGATC

C
                                                         SEQ ID NO: 265
AATGTACAGTATTGCGTTTTGGCAGATACTTGGACTTGAGTAGGCTTATT

AAACC
                                                         SEQ ID NO: 266
AATGTACAGTATTGCGTTTTGGCGGCTCTATAAAGAATTGTCCTTATTTT

CGAACTT
                                                         SEQ ID NO: 267
AATGTACAGTATTGCGTTTTGGTTCGAGGCCTTTCTCTGAGCATCAAG

SEQ ID NO: 268
AATGTACAGTATTGCGTTTTGACATCGGCAGAAACTAGATGATCAGACCA

A
```

SEQ ID NO: 269
AATGTACAGTATTGCGTTTTGTTTAGGAAATCCACAATACTTTTTCTGAT
CTCTTCC

SEQ ID NO: 270
AATGTACAGTATTGCGTTTTGGCCACCAACCTCATTCTGTTTTGTTCTCT
ATC

SEQ ID NO: 271
AATGTACAGTATTGCGTTTTGCTGCATTTGTCCTTTGACTGGTGTTTAGG
T

SEQ ID NO: 272
AATGTACAGTATTGCGTTTTGCTTCGACCGACAAACCTGAGGTCATTAAA
TC

SEQ ID NO: 273
AATGTACAGTATTGCGTTTTGCCCCACATCCCAAGCTAGGAAGACC

SEQ ID NO: 274
AATGTACAGTATTGCGTTTTGCGGGCCAGTACCTTGAAAGCGATG

SEQ ID NO: 275
AATGTACAGTATTGCGTTTTGCTAACTCAATCGGCTTGTTGTGATGCGTA
T

SEQ ID NO: 276
AATGTACAGTATTGCGTTTTGCCCTCCTGGACTGTTAGTAACTTAGTCTC
C

SEQ ID NO: 277
AATGTACAGTATTGCGTTTTGCCCTCCGAGCTCCGCGAAAAT

SEQ ID NO: 278
AATGTACAGTATTGCGTTTTGGTGCTAAAAAGTGTAAGAAGAAATGAGCT
AGCAAAA

SEQ ID NO: 279
AATGTACAGTATTGCGTTTTGCATATGCCTCAGTTTGAATTCCTCTCACA
AACAA

SEQ ID NO: 280
AATGTACAGTATTGCGTTTTGGGGAGAAGAAAGAGAGATGTAGGGCTAGA
G

SEQ ID NO: 281
AATGTACAGTATTGCGTTTTGGCAAGCACTTCTGTTTTTGTCTTTTCAGT
TTCG

SEQ ID NO: 282
AATGTACAGTATTGCGTTTTGTCTCTGATATACTTGGATTGGTAATTGAG
AAAGTCT

SEQ ID NO: 283
AATGTACAGTATTGCGTTTTGGTTTGATATCTTCCCAGCAAAATAATCAG
CTCTCAT

SEQ ID NO: 284
AATGTACAGTATTGCGTTTTGTAGCCAACCTCTTTTCGATGAGCTCACTA
G

SEQ ID NO: 285
AATGTACAGTATTGCGTTTTGTGGAACAGACAAACTATCGACTGAAGTTG
T

SEQ ID NO: 286
AATGTACAGTATTGCGTTTTGGAGGCTGAGTGCAAATTTGGTCTGGAA

SEQ ID NO: 287
AATGTACAGTATTGCGTTTTGGATGGTGGTGGTTGTCTCTGATGATTACC

SEQ ID NO: 288
AATGTACAGTATTGCGTTTTGGCAAGGCGAGTCCAGAACCAAGATT

SEQ ID NO: 289
AATGTACAGTATTGCGTTTTGTCAGAAGCGACTGATCCCCATCAAGT

SEQ ID NO: 290
AATGTACAGTATTGCGTTTTGCATATGGTCACATCACCTTAACTAAACCC
ATGTTT

SEQ ID NO: 291
AATGTACAGTATTGCGTTTTGTTTCTCGGTACTGTTTATTTTGAACAAAA
CCAATCC

SEQ ID NO: 292
AATGTACAGTATTGCGTTTTGCCTCCTCCCCAAATTCCAGGAACAATATG
A

SEQ ID NO: 293
AATGTACAGTATTGCGTTTTGTGTGCGTCATTTTATTTGGGAAAATTTGA
TACTAAC

SEQ ID NO: 294
AATGTACAGTATTGCGTTTTGCATGCAGGAGAAGTCATCCCCCTTC

SEQ ID NO: 295
AATGTACAGTATTGCGTTTTGTCTGAAAACTGGTGGTTGCCTCTAGGTTA
A

SEQ ID NO: 296
AATGTACAGTATTGCGTTTTGGCCCCTTTCTTGCTCTTCTTGGACTTG

SEQ ID NO: 297
AATGTACAGTATTGCGTTTTGCCAAGCCAAGCCAAGCTGGATATTGTG

SEQ ID NO: 298
AATGTACAGTATTGCGTTTTGCACTCACATTGTGCAGCTTGTAGTAGAG

SEQ ID NO: 299
AATGTACAGTATTGCGTTTTGGCAAAGCGTCTGCATTTGAAGGAGTTT

SEQ ID NO: 300
AATGTACAGTATTGCGTTTTGCCCTCCCGAGAACTTGCCGGTTAA

SEQ ID NO: 301
AATGTACAGTATTGCGTTTTGGCTCCCCACCACAAAAACGCAAATG

SEQ ID NO: 302
AATGTACAGTATTGCGTTTTGGTGTCACTGACGGAGAGCATGAAGATG

SEQ ID NO: 303
AATGTACAGTATTGCGTTTTGCCACCCAAAGAAGTGTCTCCTGACC

SEQ ID NO: 304
AATGTACAGTATTGCGTTTTGTCCGTCAGTGACACCTGGTACTTGAC

SEQ ID NO: 305
AATGTACAGTATTGCGTTTTGCCCTAGCTCTGCCTACCCTGATCTTTC

SEQ ID NO: 306
AATGTACAGTATTGCGTTTTGACGAGGTGGACGTCTTCTTCAATCAC

SEQ ID NO: 307
AATGTACAGTATTGCGTTTTGGCCCTGCGAGTCGAGGTGATTG

SEQ ID NO: 308
AATGTACAGTATTGCGTTTTGCCATGACTCTCAGGAATTGGCCCTATACT
TAG

-continued

SEQ ID NO: 309
AATGTACAGTATTGCGTTTTGCTTGGGACCTTCATTTCTATATAACCCCT
ATCTGG

SEQ ID NO: 310
AATGTACAGTATTGCGTTTTGTGCCAGGAAACTTTTCATTGTGCCTCTC

SEQ ID NO: 311
AATGTACAGTATTGCGTTTTGGTTACCCCATGGAACTTACCAAGCACTAG

SEQ ID NO: 312
AATGTACAGTATTGCGTTTTGGTATGAAATTCGCTGGAGGGTCATTGAAT
CAAT

SEQ ID NO: 313
AATGTACAGTATTGCGTTTTGCAGGAAGGAGCACTTACGTTTTAGCATCT
TC

SEQ ID NO: 314
AATGTACAGTATTGCGTTTTGGATTTTGAGAAATTCCCTTAATATCCCCA
TGCTCAA

SEQ ID NO: 315
AATGTACAGTATTGCGTTTTGCACAACCACATGTGTCCAGTGAAAATCC

SEQ ID NO: 316
AATGTACAGTATTGCGTTTTGTGCTTTCATCAGCAGGGTTCAATCCAAA

SEQ ID NO: 317
AATGTACAGTATTGCGTTTTGCATTTACATCATCACAGAGTATTGCTTCT
ATGGAGA

SEQ ID NO: 318
AATGTACAGTATTGCGTTTTGGTGATCTCTGGATGTCGGAATATTTAGAA
ACCTCT

SEQ ID NO: 319
AATGTACAGTATTGCGTTTTGATCTTTTGAAAACAATGGTGACTACATGG
ACATGAA

SEQ ID NO: 320
AATGTACAGTATTGCGTTTTGGGTCTAAAAAGGTCTGTGTTCCTTGAACT
TACA

SEQ ID NO: 321
AATGTACAGTATTGCGTTTTGCCAGCACCAATACATTTAATTTCTTTTCT
GCAGAC

SEQ ID NO: 322
AATGTACAGTATTGCGTTTTGGCTACAGATGGCTTGATCCTGAGTCATTT
C

SEQ ID NO: 323
AATGTACAGTATTGCGTTTTGGTCAGGCCCATACCAAGGGAAAAGATC

SEQ ID NO: 324
AATGTACAGTATTGCGTTTTGACACTGAGTGATGTCTGGTCTTATGGCAT
T

SEQ ID NO: 325
AATGTACAGTATTGCGTTTTGCACTGAGCGTTTGTTAGTCCTGGTGTTTT

SEQ ID NO: 326
AATGTACAGTATTGCGTTTTGCAGATTCTCCACAATCTCACTCAGGTGGT
AAA

SEQ ID NO: 327
AATGTACAGTATTGCGTTTTGCCCCACAGCTACGAGATCATGGTGAAAT

SEQ ID NO: 328
AATGTACAGTATTGCGTTTTGTCTCTATTCATTTTTGAGGTTTGGTTGTT
AACACTT

SEQ ID NO: 329
AATGTACAGTATTGCGTTTTGGGGAGTGCACCATTATCGGGAAAATGG

SEQ ID NO: 330
AATGTACAGTATTGCGTTTTGGCTTATTCTCATTCGTTTCATCCAGGATC
TCAAAA

SEQ ID NO: 331
AATGTACAGTATTGCGTTTTGGGGCGACGAGATTAGGCTGTTATGC

SEQ ID NO: 332
AATGTACAGTATTGCGTTTTGCCCCTCTGCATTATAAGCAGTGCCAAAA

SEQ ID NO: 333
AATGTACAGTATTGCGTTTTGGCCCACATCGTTGTAAGCCTTACATTCAA

SEQ ID NO: 334
AATGTACAGTATTGCGTTTTGCCGTTTGGAAAGCTAGTGGTTCAGAGTTC

SEQ ID NO: 335
AATGTACAGTATTGCGTTTTGGAGATCCCATCCTGCCAAAGTTTGTGATT

SEQ ID NO: 336
AATGTACAGTATTGCGTTTTGGGAAAGCCCCTGTTTCATACTGACCAAAA

SEQ ID NO: 337
AATGTACAGTATTGCGTTTTGCTTTCTCCCCACAGAAACCCATGTATGAA
G

SEQ ID NO: 338
AATGTACAGTATTGCGTTTTGGTTTGCCAGTTGTGCTTTTTGCTAAAATG
C

SEQ ID NO: 339
AATGTACAGTATTGCGTTTTGCCCTCCCACCCTCAGGACTATACCAAT

SEQ ID NO: 340
AATGTACAGTATTGCGTTTTGTGCTCGGCAGATTGGTATAGTCCTG

SEQ ID NO: 341
AATGTACAGTATTGCGTTTTGGGCATCCTCTGTCCTATCTCCCAGATACA

SEQ ID NO: 342
AATGTACAGTATTGCGTTTTGAGGTTTTATACTAAACTTACTTTGACTGG
GTTTGG

SEQ ID NO: 343
AATGTACAGTATTGCGTTTTGCCCCCAGAGGTAAGCGTCATATGG

SEQ ID NO: 344
AATGTACAGTATTGCGTTTTGGCACAGGGAAGTAGGTACTGGGAGATTG

SEQ ID NO: 345
AATGTACAGTATTGCGTTTTGAGGCCTGCAAGGTTTTAACTGGACCTA

SEQ ID NO: 346
AATGTACAGTATTGCGTTTTGCGGGAGCTGATAAGTGGTACCTGTATGT

SEQ ID NO: 347
AATGTACAGTATTGCGTTTTGGAAAAGGGTCCCAGGTAGGTCCAGTTAA

SEQ ID NO: 348
AATGTACAGTATTGCGTTTTGCTCTCGGTGTATTTCTCTACTTACCTGTA
ATAATGC

SEQ ID NO: 349
AATGTACAGTATTGCGTTTTGTTTATTGATGTCTATGAAGTGTTGTGGTT
CCTTAAC

SEQ ID NO: 350
AATGTACAGTATTGCGTTTTGCAGAAAACAAGCTGCCGCAAAGTTCTAC

SEQ ID NO: 351
AATGTACAGTATTGCGTTTTGCAGGTGTTGCGATGATGTCACTGTACG

SEQ ID NO: 352
AATGTACAGTATTGCGTTTTGTCATTTTTCATTGGACTTGTTTTGTCAGCTTTTTGG

SEQ ID NO: 353
AATGTACAGTATTGCGTTTTGGTTAGCCCCAATATGAAAAATAAAGCTGGTTGGA

SEQ ID NO: 354
AATGTACAGTATTGCGTTTTGCTGGTTGGAGGTTTTTGCTAAATCTGGAATGA

SEQ ID NO: 355
AATGTACAGTATTGCGTTTTGTTCTTTTTGACTAGAAAACTTCAGCCACTGTGTATT

SEQ ID NO: 356
AATGTACAGTATTGCGTTTTGCATATGACCAATTGCAGATGAGCCCATTATTGAA

SEQ ID NO: 357
AATGTACAGTATTGCGTTTTGAGGCATAGCTGACTCATCTATGTTTGTTCT

SEQ ID NO: 358
AATGTACAGTATTGCGTTTTGTTCCTCATTTCTTTCACTCTGACAGTATAAAGGTAA

SEQ ID NO: 359
AATGTACAGTATTGCGTTTTGGAACTATTCCAACAGAACAAACCGATAACATCA

SEQ ID NO: 360
AATGTACAGTATTGCGTTTTGTGGATAGCAAGACAATTAGAGCCCAACTTAGT

SEQ ID NO: 361
AATGTACAGTATTGCGTTTTGCTACTCCTCCTGTCTCTTTCCACATCATCAATT

SEQ ID NO: 362
AATGTACAGTATTGCGTTTTGAGGACCTTATGTTGTATGCTGTATAAATCTAAAGGT

SEQ ID NO: 363
AATGTACAGTATTGCGTTTTGGTTTGTCATCTTCTATGGTAAGTATCTTTCTGGATG

SEQ ID NO: 364
AATGTACAGTATTGCGTTTTGTGGAGGAGAAACAGATAAAAGTTGAGTATACGTTTA

SEQ ID NO: 365
AATGTACAGTATTGCGTTTTGGAGGATGACGACATGTTAGTAAGCACTACTACT

SEQ ID NO: 366
AATGTACAGTATTGCGTTTTGATTCCACCATCATTTCCTTCTCCAAAATTATCATCC

SEQ ID NO: 367
AATGTACAGTATTGCGTTTTGCTCAAAAGCACTGCCTTCTCTCATTATCTCAC

SEQ ID NO: 368
AATGTACAGTATTGCGTTTTGAATGTATTTGACCTTCTTTTAAAGTGACATCGATGT

SEQ ID NO: 369
AATGTACAGTATTGCGTTTTGTGATGTTCCCAACTTCTTCTCTCATGGTTATCTC

SEQ ID NO: 370
AATGTACAGTATTGCGTTTTGCCCTCTGATCCCTAGATAATTTATGGTAGCTAGA

SEQ ID NO: 371
AATGTACAGTATTGCGTTTTGCACGAAATGCAGGTTTTGGAATATGATTAATGTT

SEQ ID NO: 372
AATGTACAGTATTGCGTTTTGGAACAATGTTCTACGCACATTTTGTTCTCAGTAAA

SEQ ID NO: 373
AATGTACAGTATTGCGTTTTGTCCACGCTGCTCTCTAAATTACACTCGAA

SEQ ID NO: 374
AATGTACAGTATTGCGTTTTGACGTAGAACACATTTCATTTTACTCCTCTTTGG

SEQ ID NO: 375
AATGTACAGTATTGCGTTTTGGTCACATGAATGTAAATCAAGAAAACAGATGTTGTT

SEQ ID NO: 376
AATGTACAGTATTGCGTTTTGTTCTGAACTATTTATGGACAACAGTCAAACAACAAT

SEQ ID NO: 377
AATGTACAGTATTGCGTTTTGTGAAGCCATTGCGAGAACTTTATCCATAAGTATTTC

SEQ ID NO: 378
AATGTACAGTATTGCGTTTTGGCCAGAGCACATGAATAAATGAGCATCCAT

SEQ ID NO: 379
AATGTACAGTATTGCGTTTTGGGAAGCTCTCAGGGTACAAATTCTCAGATCAT

SEQ ID NO: 380
AATGTACAGTATTGCGTTTTGCTCAGGGTACAAATTCTCAGATCATCAGTCCTC

SEQ ID NO: 381
AATGTACAGTATTGCGTTTTGCTCTACACAAGCTTCCTTTCCGTCATGC

SEQ ID NO: 382
AATGTACAGTATTGCGTTTTGCCCTTCAGATCTTCTCAGCATTCGAGAGATC

SEQ ID NO: 383
AATGTACAGTATTGCGTTTTGAATCGAAGCGCTACCTGATTCCAATTCC

SEQ ID NO: 384
AATGTACAGTATTGCGTTTTGCCGACCGTAACTATTCGGTGCGTTG

SEQ ID NO: 385
AATGTACAGTATTGCGTTTTGACATTCTATCCAAGCTGTGTTCTATCTTGAGAAACT

SEQ ID NO: 386
AATGTACAGTATTGCGTTTTGCGAGTGAGGGTTTTCGTGGTTCACATC

SEQ ID NO: 387
AATGTACAGTATTGCGTTTTGCGTGGGTCCCAGTCTGCAGTTAAG

SEQ ID NO: 388
AATGTACAGTATTGCGTTTTGGCTCAGAGCCGTTCCGAGATCTT

SEQ ID NO: 389
AATGTACAGTATTGCGTTTTGGCGTTCCATCTCCCACTTGTCGTAGTT

SEQ ID NO: 390
AATGTACAGTATTGCGTTTTGCTGGCCGAGTTGGTTCATCATCATTCAA

SEQ ID NO: 391
AATGTACAGTATTGCGTTTTGTATGGTGTGTCCCCCAACTACGACAAG

SEQ ID NO: 392
AATGTACAGTATTGCGTTTTGTGAAAAGCACTTCCTGAAATAATTTCACCTTCGTTT

SEQ ID NO: 393
AATGTACAGTATTGCGTTTTGAGGTACTCCATGGCTGACGAGATCTG

SEQ ID NO: 394
AATGTACAGTATTGCGTTTTGTTGCCTTTGTTCCAAGGTCCAATGTGT

SEQ ID NO: 395
AATGTACAGTATTGCGTTTTGCGTCCCCGCATTCCAACGTCTC

SEQ ID NO: 396
AATGTACAGTATTGCGTTTTGGGCGCGCCGTTTACTTGAAGG

SEQ ID NO: 397
AATGTACAGTATTGCGTTTTGGCCTGGCGGTGCACACTATTCTG

SEQ ID NO: 398
AATGTACAGTATTGCGTTTTGAGGTGCAGCCACAAAACTTACAGATGC

SEQ ID NO: 399
AATGTACAGTATTGCGTTTTGGTGCCGAACCAATACAACCCTCTG

SEQ ID NO: 400
AATGTACAGTATTGCGTTTTGGGGCGGGTCCACCAGTTTGAAT

SEQ ID NO: 401
AATGTACAGTATTGCGTTTTGCCGCAGAGGGTTGTATTGGTTCG

SEQ ID NO: 402
AATGTACAGTATTGCGTTTTGAGCCACTCGCATTGACCATTCAAACT

SEQ ID NO: 403
AATGTACAGTATTGCGTTTTGCCACGTCTGACAGGTAGCCATGG

SEQ ID NO: 404
AATGTACAGTATTGCGTTTTGGTGAGGCTGCTGGACGAGTACAAC

SEQ ID NO: 405
AATGTACAGTATTGCGTTTTGCGCACCAGGTTGTACTCGTCCA

SEQ ID NO: 406
AATGTACAGTATTGCGTTTTGCCGCCTTTGTGCTTCTGTTCTTCGT

SEQ ID NO: 407
AATGTACAGTATTGCGTTTTGCTGATTAATCGCGTAGAAAATGACCTTATTTTGGAG

SEQ ID NO: 408
AATGTACAGTATTGCGTTTTGGCTCCATCGTCTACCTGGAGATTGACAA

SEQ ID NO: 409
AATGTACAGTATTGCGTTTTGTCTGCACGGCCTCGATCTTGTAGG

SEQ ID NO: 410
AATGTACAGTATTGCGTTTTGGCCAGCAGATGATCTTCCCCTACTACG

SEQ ID NO: 411
AATGTACAGTATTGCGTTTTGCGTCACGCTTGAAGACCACGTTG

SEQ ID NO: 412
AATGTACAGTATTGCGTTTTGGCCAGCATGCAGTTCTAAGGCTCT

SEQ ID NO: 413
AATGTACAGTATTGCGTTTTGGTGCCCGTCTCGACTCTTAGGC

SEQ ID NO: 414
AATGTACAGTATTGCGTTTTGTGTAGCCGCTGATCGTCGTGTATATGTC

SEQ ID NO: 415
AATGTACAGTATTGCGTTTTGGACTGGTACTGGTTAGTAAAGGTTGATAATATTCCA

SEQ ID NO: 416
AATGTACAGTATTGCGTTTTGGGTGAAGTAATCAGTTTGTTCACTAGTTACGTGATT

SEQ ID NO: 417
AATGTACAGTATTGCGTTTTGCTGACATGCCTACTGATTATTCTTCAAACTCATCAC

SEQ ID NO: 418
AATGTACAGTATTGCGTTTTGTGTGTGTTTTAATTGTTCCACTTGAGATTCTTAACC

SEQ ID NO: 419
AATGTACAGTATTGCGTTTTGCGTCAGCATTTTGAATCACTTCATTCTGACATGATA

SEQ ID NO: 420
AATGTACAGTATTGCGTTTTGAGTAATTTTCAACTATTGGCCTAGTGAATTTAAGCT

SEQ ID NO: 421
AATGTACAGTATTGCGTTTTGAGAAAGAGGGAAGTCACATTTATAGAGTGCTAGC

SEQ ID NO: 422
AATGTACAGTATTGCGTTTTGCATCAACAGAAACAGAACAACAAACTGTGACAAATC

SEQ ID NO: 423
AATGTACAGTATTGCGTTTTGCCAAAGAATATCCCTTTATATAGCAGTGGAACAATT

SEQ ID NO: 424
AATGTACAGTATTGCGTTTTGCAGAATATGCAGTGATAAGTGCTGTTTCATCACT

SEQ ID NO: 425
AATGTACAGTATTGCGTTTTGTTCCCCCTGTGACGACTACTTTTCCTC

SEQ ID NO: 426
AATGTACAGTATTGCGTTTTGCGGTCCCTATTTCTTCCTCTGCTTCGT

SEQ ID NO: 427
AATGTACAGTATTGCGTTTTGCTGAACAGTTCTGTCTCTATTACCCGACCTC

SEQ ID NO: 428
AATGTACAGTATTGCGTTTTGCGTTCATAGCCTTCTATCCGAGTATGTAGCA

SEQ ID NO: 429
AATGTACAGTATTGCGTTTTGCCCCTTCTGTCCTCGCAGGTTAATCC

SEQ ID NO: 430
AATGTACAGTATTGCGTTTTGGCTTCCAGCCATTTCTGAGATATCCTCACAGT

SEQ ID NO: 431
AATGTACAGTATTGCGTTTTGACCAGGAGGAACAAAGACACATGAAGATCAT

SEQ ID NO: 432
AATGTACAGTATTGCGTTTTGGCGCCCCCGAGTTTCTTACGAATC

SEQ ID NO: 433
AATGTACAGTATTGCGTTTTGTTTATACACAGTTTGGAGTTTGAGAATCAGAAGACT

SEQ ID NO: 434
AATGTACAGTATTGCGTTTTGGGTTATCTCTGGCTGATGAGATTATGAGTGATTCTC

SEQ ID NO: 435
AATGTACAGTATTGCGTTTTGGCCAAGCTAGTGATTGATGTGATTCGCTAT

SEQ ID NO: 436
AATGTACAGTATTGCGTTTTGCCCCTCCTCTAGTACTCCCTGTTTGT

SEQ ID NO: 437
AATGTACAGTATTGCGTTTTGCTCCTTCCTGTCCCAATCAACTAGTCTAGC

SEQ ID NO: 438
AATGTACAGTATTGCGTTTTGGCCTCGTCCCTCTTCCCTTAGGTAA

SEQ ID NO: 439
AATGTACAGTATTGCGTTTTGTCTCTCTTCCCATTAGTCTGAGTACTGAGTGATT

SEQ ID NO: 440
AATGTACAGTATTGCGTTTTGAGCATTTCTTGAGACTTAAAGTGGCATTCTAAAGG

SEQ ID NO: 441
AATGTACAGTATTGCGTTTTGATTTTTATTCTCAAGAGGCAGAAATACCAACTTACC

SEQ ID NO: 442
AATGTACAGTATTGCGTTTTGAATTTATAGCTCTTTTCATCTGCTTTGGTATCATCA

SEQ ID NO: 443
AATGTACAGTATTGCGTTTTGGCCTCTAATCTGATATACAGCCTTAGAAAGTCACA

SEQ ID NO: 444
AATGTACAGTATTGCGTTTTGTGTGCCATTGTCCTGGAGCAACAATT

SEQ ID NO: 445
AATGTACAGTATTGCGTTTTGAGTGTACTGCTCGTTTTCTTAATTTGAAAAGTGAGT

SEQ ID NO: 446
AATGTACAGTATTGCGTTTTGACCCATGAACTAATACTTATTTTGAGATTGGTCCAT

SEQ ID NO: 447
AATGTACAGTATTGCGTTTTGCATGGTGCAACAAAAGTAAGAATCCAACAGTTTT

SEQ ID NO: 448
AATGTACAGTATTGCGTTTTGTTGAAATGTTAAGTAAGCTTGAAATACCGATAGCAT

SEQ ID NO: 449
AATGTACAGTATTGCGTTTTGGGGAGGAAGAAAATGAAGCACGAGGAAAAC

SEQ ID NO: 450
AATGTACAGTATTGCGTTTTGATTTGGGATGTACTCTAAATTTAAAGCAGCAAATCA

SEQ ID NO: 451
AATGTACAGTATTGCGTTTTGTCAAGAGCAGAATTTGGAGACTTTGATATTAAAACT

SEQ ID NO: 452
AATGTACAGTATTGCGTTTTGCGGTTACTAACATGTTTAGGGAAATAGACAACTGTT

SEQ ID NO: 453
AATGTACAGTATTGCGTTTTGCCTGACAACAGATCCCATATAATTAACTTTCATACC

SEQ ID NO: 454
AATGTACAGTATTGCGTTTTGAGATGAAGAAGATGAGGAACGAGAGAGTAAAAGC

The foregoing description of the specific embodiments will so fully reveal the general nature of the invention that others can, by applying knowledge within the skill of the art, readily modify and/or adapt for various applications, without departing from the general concept of the invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be herein incorporated by reference. U.S. Appl. No. 62/648,174, filed Mar. 26, 2018, is incorporated herein by reference in its entirety.

What is claimed is:

1. A method for preparing DNA and cDNA libraries in a same sample comprising DNA and RNA molecules, comprising:
    ligating a DNA tag comprising a single-stranded portion to a 3' end of a double-stranded DNA molecule in the same sample to form a tagged DNA, wherein the DNA tag comprises a unique molecular identifier (UMI) and a DNA identifier;
    performing reverse transcription of a RNA molecule in the same sample in the presence of a RNA tag to form a tagged cDNA, wherein the RNA tag comprises a RNA identifier, a UMI, and a poly(T); and
    generating DNA and cDNA libraries in the same sample.

2. The method of claim 1, wherein the reverse transcription is performed in the presence of a second RNA tag, wherein the second RNA tag comprises a RNA identifier, a UMI, and a template switching oligonucleotide (TSO).

3. The method of claim 1, further comprising amplifying the tagged DNA and the tagged cDNA for enrichment with a set of gene specific primers.

4. The method of claim 3, further comprising separating the same sample into first and second samples.

5. The method of claim 1, wherein the same sample is a biological sample.

6. The method of claim 1, wherein the DNA and RNA molecules are fragmented DNA and RNA.

7. The method of claim 1, wherein the double-stranded DNA molecule contains polished ends for ligation.

8. The method of claim 1, wherein the RNA molecule is polyadenylated.

9. The method of claim 1, wherein the method does not require ribosomal depletion.

10. The method of claim 4, further comprising amplifying the first sample with primers specific for the DNA tag.

11. The method of claim 10, wherein the amplification generates the DNA library corresponding to the tagged DNA in the first sample.

12. The method of claim 4, further comprising amplifying the second sample with primers specific for the RNA tag.

13. The method of claim 12, wherein the amplification generates the cDNA library corresponding to the tagged RNA in the second sample.

14. The method of claim 1, further comprising sequencing the DNA and/or cDNA libraries.

15. The method of claim 1, wherein the DNA molecules are genomic DNA.

16. A method for preparing targeted DNA and cDNA libraries in a same sample, comprising:
    (a) obtaining purified DNA and RNA from a same biological sample;

(b) fragmenting the DNA and RNA;
(c) polishing the ends of double-stranded DNA fragments for ligation;
(d) polishing RNA fragments by polyadenylation;
(e) ligating a DNA tag comprising a single-stranded portion to a 3' end of the polished double-stranded DNA fragments in the same sample to form a tagged DNA, wherein the DNA tag comprises in a 5' to 3' direction a unique molecular identifier (UMI) and a DNA identifier;
(f) performing reverse transcription of the polished RNA fragments in the same sample in the presence of a first RNA tag to form a tagged cDNA, wherein the first RNA tag comprises in a 5' to 3' direction a RNA identifier, a UMI, and a poly(T), and a second RNA tag, wherein the second RNA tag comprises in a 5' to 3' direction a RNA identifier, a UMI, and a template switching oligonucleotide (TSO);
(g) amplifying the tagged DNA and tagged cDNA for enrichment with a set of gene specific primers to form an amplified sample;
(h) further amplifying the first amplified sample with primers specific for the DNA tag;
(i) further amplifying the amplified sample with primers specific for the RNA tag; and
(j) generating the targeted DNA and cDNA libraries in the same sample.

\* \* \* \* \*

SEQUENCE LISTING

<160> NUMBER OF SEQ ID NOS: 454

<210> SEQ ID NO 1
<211> LENGTH: 55
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (11)..(22)
<223> OTHER INFORMATION: n is a, c, g, or t
<220> FEATURE:
<221> NAME/KEY: misc_feature
<222> LOCATION: (55)..(55)
<223> OTHER INFORMATION: c is dideoxy cytosine

<400> SEQUENCE: 1
ggactccaat nnnnnnnnnn nnacgctaag aaagatcgga agagcacacg tctgc         55

<210> SEQ ID NO 2
<211> LENGTH: 11
<212> TYPE: DNA
<213> ORGANISM: Artificial Sequence
<220> FEATURE:
<223> OTHER INFORMATION: adaptor

<400> SEQUENCE: 2
attggagtcc t                                                         11

<210> SEQ ID NO 3
<211> LENGTH: 62
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (30)..(39)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (62)..(62)
<223> OTHER INFORMATION: v is a, c, or g

<400> SEQUENCE: 3
cgactcacta tagggctgga attctgacgn nnnnnnnna cgttttttt tttttttttt      60 nv                                                                   62

<210> SEQ ID NO 4
<211> LENGTH: 56
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: c is 5methyl-deoxyisocytidine
<220> FEATURE:
<221> NAME/KEY: misc_feature
<222> LOCATION: (2)..(3)
<223> OTHER INFORMATION: g is deoxyiso guanosine
<220> FEATURE:
<221> NAME/KEY: misc_feature
<222> LOCATION: (38)..(47)
<223> OTHER INFORMATION: n is a, c, g, t or u

```
<220> FEATURE:
<221> NAME/KEY: misc_feature
<222> LOCATION: (54)..(56)
<223> OTHER INFORMATION: g is riboguanosine

<400> SEQUENCE: 4
cggtaatacg actcactata gggctggaat tctgacgnnn nnnnnnatc tgcggg          56

<210> SEQ ID NO 5
<211> LENGTH: 98
<212> TYPE: DNA
<213> ORGANISM: Artificial Sequence
<220> FEATURE:
<223> OTHER INFORMATION: Primer

<400> SEQUENCE: 5
agcagtggta tcaacgcaga gtcaagcaga agacggcata cgagattccg aaacgtgact    60
ggagttcaga cgtgtgctct tccgatcttt cttagcgt                            98

<210> SEQ ID NO 6
<211> LENGTH: 115
<212> TYPE: DNA
<213> ORGANISM: Artificial Sequence
<220> FEATURE:
<223> OTHER INFORMATION: Primer

<400> SEQUENCE: 6
gtgagtgatg gttgaggatg tgtgcaagca gaagacggca tacgagatta cgtacggtga   60
ctggagttca gacgtgtgct cttccgatct cgactcacta tagggctgga attct        115

<210> SEQ ID NO 7
<211> LENGTH: 84
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (59)..(63)
<223> OTHER INFORMATION: n is a, c, g, or t

<400> SEQUENCE: 7
aatgatacgg cgaccaccga gatctacact ctttccctac acgacgctct tccgatctnn   60
nnnaatgtac agtattgcgt tttg                                          84

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
aagcagtggt atcaacgcag agt                                           23

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
gtgagtgatg gttgaggatg tgtg                                          24
```

<210> SEQ ID NO 10
<211> LENGTH: 47
<212> TYPE: DNA
<213> ORGANISM: Artificial Sequence
<220> FEATURE:
<223> OTHER INFORMATION: primer

<400> SEQUENCE: 10
aatgtacagt attgcgtttt gagccccaag tcctatgaga acctctg            47

<210> SEQ ID NO 11
<211> LENGTH: 46
<212> TYPE: DNA
<213> ORGANISM: Artificial Sequence
<220> FEATURE:
<223> OTHER INFORMATION: primer

<400> SEQUENCE: 11
aatgtacagt attgcgtttt gtggcaccag cgatcaggtc ctttat              46

<210> SEQ ID NO 12
<211> LENGTH: 47
<212> TYPE: DNA
<213> ORGANISM: Artificial Sequence
<220> FEATURE:
<223> OTHER INFORMATION: Primer

<400> SEQUENCE: 12
aatgtacagt attgcgtttt gctgagtgga gtcacagcgg agatagt             47

<210> SEQ ID NO 13
<211> LENGTH: 51
<212> TYPE: DNA
<213> ORGANISM: Artificial Sequence
<220> FEATURE:
<223> OTHER INFORMATION: Primer

<400> SEQUENCE: 13
aatgtacagt attgcgtttt gtgttccacc agtaacaaca gttgaatgtc c        51

<210> SEQ ID NO 14
<211> LENGTH: 51
<212> TYPE: DNA
<213> ORGANISM: Artificial Sequence
<220> FEATURE:
<223> OTHER INFORMATION: Primer

<400> SEQUENCE: 14
aatgtacagt attgcgtttt ggtgtgagga acatactagt gctttgcaag t        51

<210> SEQ ID NO 15
<211> LENGTH: 50
<212> TYPE: DNA
<213> ORGANISM: Artificial Sequence
<220> FEATURE:
<223> OTHER INFORMATION: Primer

<400> SEQUENCE: 15
aatgtacagt attgcgtttt gttcaaagtt gggtctgctt cagtccaaag          50

<210> SEQ ID NO 16
<211> LENGTH: 48
<212> TYPE: DNA
<213> ORGANISM: Artificial Sequence
<220> FEATURE:
<223> OTHER INFORMATION: Primer

<400> SEQUENCE: 16
aatgtacagt attgcgtttt gcccccagct tcttctctct gcactaag        48

<210> SEQ ID NO 17
<211> LENGTH: 51
<212> TYPE: DNA
<213> ORGANISM: Artificial Sequence
<220> FEATURE:
<223> OTHER INFORMATION: Primer

<400> SEQUENCE: 17
aatgtacagt attgcgtttt ggccttccca acatgcattc taacttcttc c        51

<210> SEQ ID NO 18
<211> LENGTH: 51
<212> TYPE: DNA
<213> ORGANISM: Artificial Sequence
<220> FEATURE:
<223> OTHER INFORMATION: Primer

<400> SEQUENCE: 18
aatgtacagt attgcgtttt gccagctact ctcaaaatca gcatcctttg g        51

<210> SEQ ID NO 19
<211> LENGTH: 51
<212> TYPE: DNA
<213> ORGANISM: Artificial Sequence
<220> FEATURE:
<223> OTHER INFORMATION: Primer

<400> SEQUENCE: 19
aatgtacagt attgcgtttt gccagtcctt ctgtgagtct atcctcagtt c        51

<210> SEQ ID NO 20
<211> LENGTH: 49
<212> TYPE: DNA
<213> ORGANISM: Artificial Sequence
<220> FEATURE:
<223> OTHER INFORMATION: Primer

<400> SEQUENCE: 20
aatgtacagt attgcgtttt gagagcgaac caagaatgcc tgtttacag        49

<210> SEQ ID NO 21
<211> LENGTH: 50
<212> TYPE: DNA
<213> ORGANISM: Artificial Sequence
<220> FEATURE:
<223> OTHER INFORMATION: Primer

<400> SEQUENCE: 21
aatgtacagt attgcgtttt ggagaggcac gagaacacac atctattctg        50

<210> SEQ ID NO 22
<211> LENGTH: 50
<212> TYPE: DNA
<213> ORGANISM: Artificial Sequence
<220> FEATURE:
<223> OTHER INFORMATION: Primer

<400> SEQUENCE: 22
aatgtacagt attgcgtttt gttctcttca gaagttcctt cgtcatcctt        50

<210> SEQ ID NO 23

```
<211> LENGTH: 48
<212> TYPE: DNA
<213> ORGANISM: Artificial Sequence
<220> FEATURE:
<223> OTHER INFORMATION: Primer

<400> SEQUENCE: 23
aatgtacagt attgcgttttt gtgatgacat gccccatcac taaaacac                    48

<210> SEQ ID NO 24
<211> LENGTH: 56
<212> TYPE: DNA
<213> ORGANISM: Artificial Sequence
<220> FEATURE:
<223> OTHER INFORMATION: Primer

<400> SEQUENCE: 24
aatgtacagt attgcgttttt gtgatagaga catgatgtaa ccgtgggaat ttcttc           56

<210> SEQ ID NO 25
<211> LENGTH: 55
<212> TYPE: DNA
<213> ORGANISM: Artificial Sequence
<220> FEATURE:
<223> OTHER INFORMATION: Primer

<400> SEQUENCE: 25
aatgtacagt attgcgttttt gcgttctaag agagtgacag aaaggtaaag aggag            55

<210> SEQ ID NO 26
<211> LENGTH: 57
<212> TYPE: DNA
<213> ORGANISM: Artificial Sequence
<220> FEATURE:
<223> OTHER INFORMATION: Primer

<400> SEQUENCE: 26
aatgtacagt attgcgttttt gatcacaaag tatctttttc tgtggcttag aaatctt          57

<210> SEQ ID NO 27
<211> LENGTH: 57
<212> TYPE: DNA
<213> ORGANISM: Artificial Sequence
<220> FEATURE:
<223> OTHER INFORMATION: Primer

<400> SEQUENCE: 27
aatgtacagt attgcgttttt gtcaaatgtt agctcatttt tgttaatggt ggctttt          57

<210> SEQ ID NO 28
<211> LENGTH: 57
<212> TYPE: DNA
<213> ORGANISM: Artificial Sequence
<220> FEATURE:
<223> OTHER INFORMATION: Primer

<400> SEQUENCE: 28
aatgtacagt attgcgttttt gtgtcacatt ataaagattc aggcaatgtt tgttagt          57

<210> SEQ ID NO 29
<211> LENGTH: 57
<212> TYPE: DNA
<213> ORGANISM: Artificial Sequence
<220> FEATURE:
<223> OTHER INFORMATION: Primer

<400> SEQUENCE: 29
```

```
aatgtacagt attgcgttttt gagtttgtat gcaacatttc taaagttacc tacttgt        57

<210> SEQ ID NO 30
<211> LENGTH: 57
<212> TYPE: DNA
<213> ORGANISM: Artificial Sequence
<220> FEATURE:
<223> OTHER INFORMATION: Primer

<400> SEQUENCE: 30
aatgtacagt attgcgtttt gaaaatctgt tttccaataa attctcagat ccaggaa        57

<210> SEQ ID NO 31
<211> LENGTH: 57
<212> TYPE: DNA
<213> ORGANISM: Artificial Sequence
<220> FEATURE:
<223> OTHER INFORMATION: Primer

<400> SEQUENCE: 31
aatgtacagt attgcgtttt gcgacccagt taccatagca atttagtgaa ataacta        57

<210> SEQ ID NO 32
<211> LENGTH: 57
<212> TYPE: DNA
<213> ORGANISM: Artificial Sequence
<220> FEATURE:
<223> OTHER INFORMATION: Primer

<400> SEQUENCE: 32
aatgtacagt attgcgtttt gagaggcgct atgtgtatta ttatagctac ctgttaa        57

<210> SEQ ID NO 33
<211> LENGTH: 55
<212> TYPE: DNA
<213> ORGANISM: Artificial Sequence
<220> FEATURE:
<223> OTHER INFORMATION: Primer

<400> SEQUENCE: 33
aatgtacagt attgcgtttt gcgttttttga cagtttgaca gttaaaggca tttcc         55

<210> SEQ ID NO 34
<211> LENGTH: 57
<212> TYPE: DNA
<213> ORGANISM: Artificial Sequence
<220> FEATURE:
<223> OTHER INFORMATION: Primer

<400> SEQUENCE: 34
aatgtacagt attgcgtttt gctgtcctta ttttggatat ttctcccaat gaaagta        57

<210> SEQ ID NO 35
<211> LENGTH: 57
<212> TYPE: DNA
<213> ORGANISM: Artificial Sequence
<220> FEATURE:
<223> OTHER INFORMATION: Primer

<400> SEQUENCE: 35
aatgtacagt attgcgtttt ggacttttttg caaatgttta acataggtga cagattt        57

<210> SEQ ID NO 36
<211> LENGTH: 57
<212> TYPE: DNA
```

```
<213> ORGANISM: Artificial Sequence
<220> FEATURE:
<223> OTHER INFORMATION: Primer

<400> SEQUENCE: 36
aatgtacagt attgcgtttt gaagtagaaa atggaagtct atgtgatcaa gaaatcg        57

<210> SEQ ID NO 37
<211> LENGTH: 55
<212> TYPE: DNA
<213> ORGANISM: Artificial Sequence
<220> FEATURE:
<223> OTHER INFORMATION: Primer

<400> SEQUENCE: 37
aatgtacagt attgcgtttt gggcctctta aagatcatgt tgttacagt gctta           55

<210> SEQ ID NO 38
<211> LENGTH: 57
<212> TYPE: DNA
<213> ORGANISM: Artificial Sequence
<220> FEATURE:
<223> OTHER INFORMATION: Primer

<400> SEQUENCE: 38
aatgtacagt attgcgtttt gacaagattg gtcaggaaaa gagaattgtt cctataa        57

<210> SEQ ID NO 39
<211> LENGTH: 57
<212> TYPE: DNA
<213> ORGANISM: Artificial Sequence
<220> FEATURE:
<223> OTHER INFORMATION: Primer

<400> SEQUENCE: 39
aatgtacagt attgcgtttt gagaccctgt ctcaaaagta aaagtaagt taacatg         57

<210> SEQ ID NO 40
<211> LENGTH: 56
<212> TYPE: DNA
<213> ORGANISM: Artificial Sequence
<220> FEATURE:
<223> OTHER INFORMATION: Primer

<400> SEQUENCE: 40
aatgtacagt attgcgtttt gtcagtgtct tccaaatcct tatgtatagc agcaat         56

<210> SEQ ID NO 41
<211> LENGTH: 48
<212> TYPE: DNA
<213> ORGANISM: Artificial Sequence
<220> FEATURE:
<223> OTHER INFORMATION: Primer

<400> SEQUENCE: 41
aatgtacagt attgcgtttt gagggtcgag gaagccagtt tacatcaa                  48

<210> SEQ ID NO 42
<211> LENGTH: 57
<212> TYPE: DNA
<213> ORGANISM: Artificial Sequence
<220> FEATURE:
<223> OTHER INFORMATION: Primer

<400> SEQUENCE: 42
aatgtacagt attgcgtttt gaacaaaaag atattttcaa tatttctgcg caggttt        57
```

<210> SEQ ID NO 43
<211> LENGTH: 57
<212> TYPE: DNA
<213> ORGANISM: Artificial Sequence
<220> FEATURE:
<223> OTHER INFORMATION: primer

<400> SEQUENCE: 43
aatgtacagt attgcgttttt ggtctcgact tgaattgcaa aaagatgtta gaaaagc       57

<210> SEQ ID NO 44
<211> LENGTH: 57
<212> TYPE: DNA
<213> ORGANISM: Artificial Sequence
<220> FEATURE:
<223> OTHER INFORMATION: Primer

<400> SEQUENCE: 44
aatgtacagt attgcgttttt gaaaatgttg gcagtcataa catttgaaac taatgga       57

<210> SEQ ID NO 45
<211> LENGTH: 55
<212> TYPE: DNA
<213> ORGANISM: Artificial Sequence
<220> FEATURE:
<223> OTHER INFORMATION: Primer

<400> SEQUENCE: 45
aatgtacagt attgcgttttt gagcctcaaa caggttggtt ttaaatttga agtct         55

<210> SEQ ID NO 46
<211> LENGTH: 56
<212> TYPE: DNA
<213> ORGANISM: Artificial Sequence
<220> FEATURE:
<223> OTHER INFORMATION: Primer

<400> SEQUENCE: 46
aatgtacagt attgcgttttt gcctctgtgt gtatgtttta actacaaagc gaaaca        56

<210> SEQ ID NO 47
<211> LENGTH: 57
<212> TYPE: DNA
<213> ORGANISM: Artificial Sequence
<220> FEATURE:
<223> OTHER INFORMATION: Primer

<400> SEQUENCE: 47
aatgtacagt attgcgttttt ggattcacct ggtaatgagg aaaacagctt taaaatc       57

<210> SEQ ID NO 48
<211> LENGTH: 56
<212> TYPE: DNA
<213> ORGANISM: Artificial Sequence
<220> FEATURE:
<223> OTHER INFORMATION: Primer

<400> SEQUENCE: 48
aatgtacagt attgcgttttt gagatctgct gaaagaaat ttgttaaagc acaatt         56

<210> SEQ ID NO 49
<211> LENGTH: 45
<212> TYPE: DNA
<213> ORGANISM: Artificial Sequence
<220> FEATURE:

<223> OTHER INFORMATION: Primer

<400> SEQUENCE: 49
aatgtacagt attgcgttttt gcggcatccc ctacatcgag acctc          45

<210> SEQ ID NO 50
<211> LENGTH: 46
<212> TYPE: DNA
<213> ORGANISM: Artificial Sequence
<220> FEATURE:
<223> OTHER INFORMATION: Primer

<400> SEQUENCE: 50
aatgtacagt attgcgtttt gcagggagca gatcaaacgg gtgaag          46

<210> SEQ ID NO 51
<211> LENGTH: 51
<212> TYPE: DNA
<213> ORGANISM: Artificial Sequence
<220> FEATURE:
<223> OTHER INFORMATION: Primer

<400> SEQUENCE: 51
aatgtacagt attgcgtttt gcaagtcttt tgaggacatc caccagtaca g          51

<210> SEQ ID NO 52
<211> LENGTH: 46
<212> TYPE: DNA
<213> ORGANISM: Artificial Sequence
<220> FEATURE:
<223> OTHER INFORMATION: Primer

<400> SEQUENCE: 52
aatgtacagt attgcgtttt gacgtgcctg ttggacatcc tggata          46

<210> SEQ ID NO 53
<211> LENGTH: 50
<212> TYPE: DNA
<213> ORGANISM: Artificial Sequence
<220> FEATURE:
<223> OTHER INFORMATION: Primer

<400> SEQUENCE: 53
aatgtacagt attgcgtttt gcctgtactg gtggatgtcc tcaaaagact          50

<210> SEQ ID NO 54
<211> LENGTH: 49
<212> TYPE: DNA
<213> ORGANISM: Artificial Sequence
<220> FEATURE:
<223> OTHER INFORMATION: Primer

<400> SEQUENCE: 54
aatgtacagt attgcgtttt gccctgagga gcgatgacgg aatataagc          49

<210> SEQ ID NO 55
<211> LENGTH: 52
<212> TYPE: DNA
<213> ORGANISM: Artificial Sequence
<220> FEATURE:
<223> OTHER INFORMATION: primer

<400> SEQUENCE: 55
aatgtacagt attgcgtttt ggtcgtattc gtccacaaaa tggttctgga tc          52

```
<210> SEQ ID NO 56
<211> LENGTH: 50
<212> TYPE: DNA
<213> ORGANISM: Artificial Sequence
<220> FEATURE:
<223> OTHER INFORMATION: Primer

<400> SEQUENCE: 56
aatgtacagt attgcgtttt gtgactggca attgtgtcaa caggtgaaaa          50

<210> SEQ ID NO 57
<211> LENGTH: 46
<212> TYPE: DNA
<213> ORGANISM: Artificial Sequence
<220> FEATURE:
<223> OTHER INFORMATION: Primer

<400> SEQUENCE: 57
aatgtacagt attgcgtttt gcgccagctg gagtttggtc atgttt              46

<210> SEQ ID NO 58
<211> LENGTH: 57
<212> TYPE: DNA
<213> ORGANISM: Artificial Sequence
<220> FEATURE:
<223> OTHER INFORMATION: Primer

<400> SEQUENCE: 58
aatgtacagt attgcgtttt gaatccctct catcacaatt tcattccaca atagttt  57

<210> SEQ ID NO 59
<211> LENGTH: 56
<212> TYPE: DNA
<213> ORGANISM: Artificial Sequence
<220> FEATURE:
<223> OTHER INFORMATION: Primer

<400> SEQUENCE: 59
aatgtacagt attgcgtttt gtcaacaaca aagagaatca tgaaatcaac cctagc   56

<210> SEQ ID NO 60
<211> LENGTH: 46
<212> TYPE: DNA
<213> ORGANISM: Artificial Sequence
<220> FEATURE:
<223> OTHER INFORMATION: Primer

<400> SEQUENCE: 60
aatgtacagt attgcgtttt ggatatggag ccagcgtgtt ccgatt              46

<210> SEQ ID NO 61
<211> LENGTH: 43
<212> TYPE: DNA
<213> ORGANISM: Artificial Sequence
<220> FEATURE:
<223> OTHER INFORMATION: Primer

<400> SEQUENCE: 61
aatgtacagt attgcgtttt gggcgcggaa agtcctcact ctc                 43

<210> SEQ ID NO 62
<211> LENGTH: 48
<212> TYPE: DNA
<213> ORGANISM: Artificial Sequence
<220> FEATURE:
<223> OTHER INFORMATION: Primer
```

<400> SEQUENCE: 62
aatgtacagt attgcgtttt gtatggtgag gttcggcgtg tttaaacg    48

<210> SEQ ID NO 63
<211> LENGTH: 48
<212> TYPE: DNA
<213> ORGANISM: Artificial Sequence
<220> FEATURE:
<223> OTHER INFORMATION: Primer

<400> SEQUENCE: 63
aatgtacagt attgcgtttt gtggtgacaa agttagaagg gtccatgg    48

<210> SEQ ID NO 64
<211> LENGTH: 50
<212> TYPE: DNA
<213> ORGANISM: Artificial Sequence
<220> FEATURE:
<223> OTHER INFORMATION: Primer

<400> SEQUENCE: 64
aatgtacagt attgcgtttt gcttctttac caccccagat acgacgacta    50

<210> SEQ ID NO 65
<211> LENGTH: 45
<212> TYPE: DNA
<213> ORGANISM: Artificial Sequence
<220> FEATURE:
<223> OTHER INFORMATION: Primer

<400> SEQUENCE: 65
aatgtacagt attgcgtttt gcgctcgtgg tggtagtcgt cgtat    45

<210> SEQ ID NO 66
<211> LENGTH: 47
<212> TYPE: DNA
<213> ORGANISM: Artificial Sequence
<220> FEATURE:
<223> OTHER INFORMATION: Primer

<400> SEQUENCE: 66
aatgtacagt attgcgtttt gccaggaggc cctttctgtt tacaacc    47

<210> SEQ ID NO 67
<211> LENGTH: 53
<212> TYPE: DNA
<213> ORGANISM: Artificial Sequence
<220> FEATURE:
<223> OTHER INFORMATION: Primer

<400> SEQUENCE: 67
aatgtacagt attgcgtttt gcccacaagc ccaaaatatt ctactcactt tgc    53

<210> SEQ ID NO 68
<211> LENGTH: 49
<212> TYPE: DNA
<213> ORGANISM: Artificial Sequence
<220> FEATURE:
<223> OTHER INFORMATION: Primer

<400> SEQUENCE: 68
aatgtacagt attgcgtttt gatcgcctgc atcaaggaaa aggtaatgg    49

<210> SEQ ID NO 69
<211> LENGTH: 50

<212> TYPE: DNA
<213> ORGANISM: Artificial Sequence
<220> FEATURE:
<223> OTHER INFORMATION: Primer

<400> SEQUENCE: 69
aatgtacagt attgcgtttt gcgcgtaagg atagcaactg aggttatcac                50

<210> SEQ ID NO 70
<211> LENGTH: 47
<212> TYPE: DNA
<213> ORGANISM: Artificial Sequence
<220> FEATURE:
<223> OTHER INFORMATION: Primer

<400> SEQUENCE: 70
aatgtacagt attgcgtttt gcgacctgac gtaacccctt gcttatc                   47

<210> SEQ ID NO 71
<211> LENGTH: 51
<212> TYPE: DNA
<213> ORGANISM: Artificial Sequence
<220> FEATURE:
<223> OTHER INFORMATION: Primer

<400> SEQUENCE: 71
aatgtacagt attgcgtttt gggaaatgct ctcacgtagt ctctcatgtc t              51

<210> SEQ ID NO 72
<211> LENGTH: 51
<212> TYPE: DNA
<213> ORGANISM: Artificial Sequence
<220> FEATURE:
<223> OTHER INFORMATION: Primer

<400> SEQUENCE: 72
aatgtacagt attgcgtttt ggtcataacc cgaagaacaa tgttgccact a              51

<210> SEQ ID NO 73
<211> LENGTH: 50
<212> TYPE: DNA
<213> ORGANISM: Artificial Sequence
<220> FEATURE:
<223> OTHER INFORMATION: Primer

<400> SEQUENCE: 73
aatgtacagt attgcgtttt ggtcagctca ggataaagca cggatggata               50

<210> SEQ ID NO 74
<211> LENGTH: 57
<212> TYPE: DNA
<213> ORGANISM: Artificial Sequence
<220> FEATURE:
<223> OTHER INFORMATION: Primer

<400> SEQUENCE: 74
aatgtacagt attgcgtttt gctcaggata aaagcttcct tcttaacaag tttttcc        57

<210> SEQ ID NO 75
<211> LENGTH: 53
<212> TYPE: DNA
<213> ORGANISM: Artificial Sequence
<220> FEATURE:
<223> OTHER INFORMATION: Primer

<400> SEQUENCE: 75
aatgtacagt attgcgttttt gagagattgt tcccttgcat tgacctcttt ttc    53

<210> SEQ ID NO 76
<211> LENGTH: 50
<212> TYPE: DNA
<213> ORGANISM: Artificial Sequence
<220> FEATURE:
<223> OTHER INFORMATION: Primer

<400> SEQUENCE: 76
aatgtacagt attgcgttttt gcccctcacc tttggaattt acagtctgaa    50

<210> SEQ ID NO 77
<211> LENGTH: 56
<212> TYPE: DNA
<213> ORGANISM: Artificial Sequence
<220> FEATURE:
<223> OTHER INFORMATION: Primer

<400> SEQUENCE: 77
aatgtacagt attgcgttttt gtaggttctt caggtctcta cactctcctt taaact    56

<210> SEQ ID NO 78
<211> LENGTH: 52
<212> TYPE: DNA
<213> ORGANISM: Artificial Sequence
<220> FEATURE:
<223> OTHER INFORMATION: Primer

<400> SEQUENCE: 78
aatgtacagt attgcgttttt ggagaaggag tgcaatgcca agattatgat cc    52

<210> SEQ ID NO 79
<211> LENGTH: 50
<212> TYPE: DNA
<213> ORGANISM: Artificial Sequence
<220> FEATURE:
<223> OTHER INFORMATION: Primer

<400> SEQUENCE: 79
aatgtacagt attgcgttttt ggacgttctc cattgtattg gcagtaacca    50

<210> SEQ ID NO 80
<211> LENGTH: 57
<212> TYPE: DNA
<213> ORGANISM: Artificial Sequence
<220> FEATURE:
<223> OTHER INFORMATION: Primer

<400> SEQUENCE: 80
aatgtacagt attgcgttttt gcacatctca caggctctaa aggaattcta tatccta    57

<210> SEQ ID NO 81
<211> LENGTH: 52
<212> TYPE: DNA
<213> ORGANISM: Artificial Sequence
<220> FEATURE:
<223> OTHER INFORMATION: Primer

<400> SEQUENCE: 81
aatgtacagt attgcgttttt ggaggcaaga ggtgagtagt accaatactg tc    52

<210> SEQ ID NO 82
<211> LENGTH: 47
<212> TYPE: DNA
<213> ORGANISM: Artificial Sequence

```
<220> FEATURE:
<223> OTHER INFORMATION: Prmer

<400> SEQUENCE: 82
aatgtacagt attgcgtttt ggagcccctc cgcttacttg taatctg          47

<210> SEQ ID NO 83
<211> LENGTH: 57
<212> TYPE: DNA
<213> ORGANISM: Artificial Sequence
<220> FEATURE:
<223> OTHER INFORMATION: Primer

<400> SEQUENCE: 83
aatgtacagt attgcgtttt gccagtaaaa cgtattgaga aaaggtaaa agcgtta    57

<210> SEQ ID NO 84
<211> LENGTH: 57
<212> TYPE: DNA
<213> ORGANISM: Artificial Sequence
<220> FEATURE:
<223> OTHER INFORMATION: Primer

<400> SEQUENCE: 84
aatgtacagt attgcgtttt ggctcagaat aaatcgtaac aatctcaaag tgcattt    57

<210> SEQ ID NO 85
<211> LENGTH: 49
<212> TYPE: DNA
<213> ORGANISM: Artificial Sequence
<220> FEATURE:
<223> OTHER INFORMATION: Primer

<400> SEQUENCE: 85
aatgtacagt attgcgtttt gtgaggtgtc cacagggctc aatctttac          49

<210> SEQ ID NO 86
<211> LENGTH: 57
<212> TYPE: DNA
<213> ORGANISM: Artificial Sequence
<220> FEATURE:
<223> OTHER INFORMATION: Primer

<400> SEQUENCE: 86
aatgtacagt attgcgtttt gccccttgta tcagtaaagg ctatataata ccgaatt    57

<210> SEQ ID NO 87
<211> LENGTH: 55
<212> TYPE: DNA
<213> ORGANISM: Artificial Sequence
<220> FEATURE:
<223> OTHER INFORMATION: Primer

<400> SEQUENCE: 87
aatgtacagt attgcgtttt gtcatgaaga gagtatcatc agctcgttca tcatc      55

<210> SEQ ID NO 88
<211> LENGTH: 53
<212> TYPE: DNA
<213> ORGANISM: Artificial Sequence
<220> FEATURE:
<223> OTHER INFORMATION: Primer

<400> SEQUENCE: 88
aatgtacagt attgcgtttt gtgtcctttc tgccgatgtg aaattaaagg tac          53
```

<210> SEQ ID NO 89
<211> LENGTH: 47
<212> TYPE: DNA
<213> ORGANISM: Artificial Sequence
<220> FEATURE:
<223> OTHER INFORMATION: Primer

<400> SEQUENCE: 89
aatgtacagt attgcgtttt gtcgccccaa ataatttcct gcgaaca    47

<210> SEQ ID NO 90
<211> LENGTH: 53
<212> TYPE: DNA
<213> ORGANISM: Artificial Sequence
<220> FEATURE:
<223> OTHER INFORMATION: Primer

<400> SEQUENCE: 90
aatgtacagt attgcgtttt gctcatacct ccattccaag ctttcattgt ctc    53

<210> SEQ ID NO 91
<211> LENGTH: 52
<212> TYPE: DNA
<213> ORGANISM: Artificial Sequence
<220> FEATURE:
<223> OTHER INFORMATION: Primer

<400> SEQUENCE: 91
aatgtacagt attgcgtttt gcctgccctt atttttaaca gcaggaacga at    52

<210> SEQ ID NO 92
<211> LENGTH: 48
<212> TYPE: DNA
<213> ORGANISM: Artificial Sequence
<220> FEATURE:
<223> OTHER INFORMATION: Primer

<400> SEQUENCE: 92
aatgtacagt attgcgtttt gtcgatagcg aaagtcctct ttggtcag    48

<210> SEQ ID NO 93
<211> LENGTH: 57
<212> TYPE: DNA
<213> ORGANISM: Artificial Sequence
<220> FEATURE:
<223> OTHER INFORMATION: Primer

<400> SEQUENCE: 93
aatgtacagt attgcgtttt ggttaaagac caaccactaa ctaagagact ttccaag    57

<210> SEQ ID NO 94
<211> LENGTH: 52
<212> TYPE: DNA
<213> ORGANISM: Artificial Sequence
<220> FEATURE:
<223> OTHER INFORMATION: Primer

<400> SEQUENCE: 94
aatgtacagt attgcgtttt gaaacctctt ccagtacctt cttcatggtt ct    52

<210> SEQ ID NO 95
<211> LENGTH: 51
<212> TYPE: DNA
<213> ORGANISM: Artificial Sequence
<220> FEATURE:
<223> OTHER INFORMATION: Primer

<400> SEQUENCE: 95
aatgtacagt attgcgttttt gtttccaggt gatgtgctct atgaactcct t    51

<210> SEQ ID NO 96
<211> LENGTH: 45
<212> TYPE: DNA
<213> ORGANISM: Artificial Sequence
<220> FEATURE:
<223> OTHER INFORMATION: Primer

<400> SEQUENCE: 96
aatgtacagt attgcgttttt gggagcggtg caacagttca atggt    45

<210> SEQ ID NO 97
<211> LENGTH: 48
<212> TYPE: DNA
<213> ORGANISM: Artificial Sequence
<220> FEATURE:
<223> OTHER INFORMATION: Primer

<400> SEQUENCE: 97
aatgtacagt attgcgttttt gcatccgtgg ataatgtgca ccataacc    48

<210> SEQ ID NO 98
<211> LENGTH: 47
<212> TYPE: DNA
<213> ORGANISM: Artificial Sequence
<220> FEATURE:
<223> OTHER INFORMATION: Primer

<400> SEQUENCE: 98
aatgtacagt attgcgttttt gtcggagagc ctggactgtt tgaaatc    47

<210> SEQ ID NO 99
<211> LENGTH: 46
<212> TYPE: DNA
<213> ORGANISM: Artificial Sequence
<220> FEATURE:
<223> OTHER INFORMATION: Primer

<400> SEQUENCE: 99
aatgtacagt attgcgttttt gaagccaggt cttcccgatg agagag    46

<210> SEQ ID NO 100
<211> LENGTH: 46
<212> TYPE: DNA
<213> ORGANISM: Artificial Sequence
<220> FEATURE:
<223> OTHER INFORMATION: Primer

<400> SEQUENCE: 100
aatgtacagt attgcgttttt gggcactccg tggatttcaa acagtc    46

<210> SEQ ID NO 101
<211> LENGTH: 53
<212> TYPE: DNA
<213> ORGANISM: Artificial Sequence
<220> FEATURE:
<223> OTHER INFORMATION: Primer

<400> SEQUENCE: 101
aatgtacagt attgcgttttt gcagatatct gctgcccttt taccttatgg ttt    53

<210> SEQ ID NO 102

```
<211> LENGTH: 54
<212> TYPE: DNA
<213> ORGANISM: Artificial Sequence
<220> FEATURE:
<223> OTHER INFORMATION: Primer

<400> SEQUENCE: 102
aatgtacagt attgcgtttt gtgtagactg ctttgggatt acgtctatca gttg          54

<210> SEQ ID NO 103
<211> LENGTH: 52
<212> TYPE: DNA
<213> ORGANISM: Artificial Sequence
<220> FEATURE:
<223> OTHER INFORMATION: primer

<400> SEQUENCE: 103
aatgtacagt attgcgtttt gggaaaggag aaaaaggaag tgctacctga ac            52

<210> SEQ ID NO 104
<211> LENGTH: 51
<212> TYPE: DNA
<213> ORGANISM: Artificial Sequence
<220> FEATURE:
<223> OTHER INFORMATION: Primer

<400> SEQUENCE: 104
aatgtacagt attgcgtttt gttttctcc cttcctcctt tgaacaaaca g              51

<210> SEQ ID NO 105
<211> LENGTH: 55
<212> TYPE: DNA
<213> ORGANISM: Artificial Sequence
<220> FEATURE:
<223> OTHER INFORMATION: Primer

<400> SEQUENCE: 105
aatgtacagt attgcgtttt gacagcttta ggaaaatgga atctcttacc tcctc         55

<210> SEQ ID NO 106
<211> LENGTH: 48
<212> TYPE: DNA
<213> ORGANISM: Artificial Sequence
<220> FEATURE:
<223> OTHER INFORMATION: Primer

<400> SEQUENCE: 106
aatgtacagt attgcgtttt ggggtgttat ggtcgcgttg gatttctg                 48

<210> SEQ ID NO 107
<211> LENGTH: 45
<212> TYPE: DNA
<213> ORGANISM: Artificial Sequence
<220> FEATURE:
<223> OTHER INFORMATION: Primer

<400> SEQUENCE: 107
aatgtacagt attgcgtttt ggctacggcg tgcaactcac agaac                    45

<210> SEQ ID NO 108
<211> LENGTH: 44
<212> TYPE: DNA
<213> ORGANISM: Artificial Sequence
<220> FEATURE:
<223> OTHER INFORMATION: Primer

<400> SEQUENCE: 108
```
aatgtacagt attgcgtttt gaccgacctc ttccagcgct actt                    44

<210> SEQ ID NO 109
<211> LENGTH: 44
<212> TYPE: DNA
<213> ORGANISM: Artificial Sequence
<220> FEATURE:
<223> OTHER INFORMATION: Primer

<400> SEQUENCE: 109
aatgtacagt attgcgtttt gcgggcaggg cttacttacc ttgg                    44

<210> SEQ ID NO 110
<211> LENGTH: 49
<212> TYPE: DNA
<213> ORGANISM: Artificial Sequence
<220> FEATURE:
<223> OTHER INFORMATION: Primer

<400> SEQUENCE: 110
aatgtacagt attgcgtttt gtagctactg cctgccttcg aagaacgat               49

<210> SEQ ID NO 111
<211> LENGTH: 54
<212> TYPE: DNA
<213> ORGANISM: Artificial Sequence
<220> FEATURE:
<223> OTHER INFORMATION: Primer

<400> SEQUENCE: 111
aatgtacagt attgcgtttt gtgtgggtgg aaaaagatgt ggttaagaaa caac         54

<210> SEQ ID NO 112
<211> LENGTH: 50
<212> TYPE: DNA
<213> ORGANISM: Artificial Sequence
<220> FEATURE:
<223> OTHER INFORMATION: Primer

<400> SEQUENCE: 112
aatgtacagt attgcgtttt gcccccatat agcttaatct gatgggcatc              50

<210> SEQ ID NO 113
<211> LENGTH: 51
<212> TYPE: DNA
<213> ORGANISM: Artificial Sequence
<220> FEATURE:
<223> OTHER INFORMATION: Primer

<400> SEQUENCE: 113
aatgtacagt attgcgtttt ggaaagagca tcaggaacaa gccttgagta c            51

<210> SEQ ID NO 114
<211> LENGTH: 51
<212> TYPE: DNA
<213> ORGANISM: Artificial Sequence
<220> FEATURE:
<223> OTHER INFORMATION: Primer

<400> SEQUENCE: 114
aatgtacagt attgcgtttt gttgagatgc ctgacaacct ttacaccttt g            51

<210> SEQ ID NO 115
<211> LENGTH: 49
<212> TYPE: DNA

```
<213> ORGANISM: Artificial Sequence
<220> FEATURE:
<223> OTHER INFORMATION: Primer

<400> SEQUENCE: 115
aatgtacagt attgcgtttt gctctagggc tgagggaata tgcatctct         49

<210> SEQ ID NO 116
<211> LENGTH: 49
<212> TYPE: DNA
<213> ORGANISM: Artificial Sequence
<220> FEATURE:
<223> OTHER INFORMATION: Primer

<400> SEQUENCE: 116
aatgtacagt attgcgtttt gcgtacccag aagacaatgg cctagctat         49

<210> SEQ ID NO 117
<211> LENGTH: 45
<212> TYPE: DNA
<213> ORGANISM: Artificial Sequence
<220> FEATURE:
<223> OTHER INFORMATION: Primer

<400> SEQUENCE: 117
aatgtacagt attgcgtttt ggggcagcac agattccctt aacca             45

<210> SEQ ID NO 118
<211> LENGTH: 49
<212> TYPE: DNA
<213> ORGANISM: Artificial Sequence
<220> FEATURE:
<223> OTHER INFORMATION: Primer

<400> SEQUENCE: 118
aatgtacagt attgcgtttt gccataccttt ggctatcccc tgaaagttg        49

<210> SEQ ID NO 119
<211> LENGTH: 46
<212> TYPE: DNA
<213> ORGANISM: Artificial Sequence
<220> FEATURE:
<223> OTHER INFORMATION: Primer

<400> SEQUENCE: 119
aatgtacagt attgcgtttt ggccctgatg ctcatggagt gttcct            46

<210> SEQ ID NO 120
<211> LENGTH: 44
<212> TYPE: DNA
<213> ORGANISM: Artificial Sequence
<220> FEATURE:
<223> OTHER INFORMATION: Primer

<400> SEQUENCE: 120
aatgtacagt attgcgtttt gcctggtggt tgggagacga ctac              44

<210> SEQ ID NO 121
<211> LENGTH: 49
<212> TYPE: DNA
<213> ORGANISM: Artificial Sequence
<220> FEATURE:
<223> OTHER INFORMATION: Primer

<400> SEQUENCE: 121
aatgtacagt attgcgtttt gtgctgacag gacacagaac aagatacct         49
```

<210> SEQ ID NO 122
<211> LENGTH: 52
<212> TYPE: DNA
<213> ORGANISM: Artificial Sequence
<220> FEATURE:
<223> OTHER INFORMATION: Primer

<400> SEQUENCE: 122
aatgtacagt attgcgtttt gggtacaggt atcttgttct gtgtcctgtc ag    52

<210> SEQ ID NO 123
<211> LENGTH: 43
<212> TYPE: DNA
<213> ORGANISM: Artificial Sequence
<220> FEATURE:
<223> OTHER INFORMATION: Primer

<400> SEQUENCE: 123
aatgtacagt attgcgtttt ggagtcccgg gctcgattca cag    43

<210> SEQ ID NO 124
<211> LENGTH: 50
<212> TYPE: DNA
<213> ORGANISM: Artificial Sequence
<220> FEATURE:
<223> OTHER INFORMATION: Primer

<400> SEQUENCE: 124
aatgtacagt attgcgtttt gctggtcaga gaggtgtgta ctgattgtct    50

<210> SEQ ID NO 125
<211> LENGTH: 57
<212> TYPE: DNA
<213> ORGANISM: Artificial Sequence
<220> FEATURE:
<223> OTHER INFORMATION: Primer

<400> SEQUENCE: 125
aatgtacagt attgcgtttt gaggaaagat caattacatt cacaagttca cacttct    57

<210> SEQ ID NO 126
<211> LENGTH: 55
<212> TYPE: DNA
<213> ORGANISM: Artificial Sequence
<220> FEATURE:
<223> OTHER INFORMATION: Primer

<400> SEQUENCE: 126
aatgtacagt attgcgtttt gctgcacagt tcagaggata tttaagctca atgac    55

<210> SEQ ID NO 127
<211> LENGTH: 49
<212> TYPE: DNA
<213> ORGANISM: Artificial Sequence
<220> FEATURE:
<223> OTHER INFORMATION: Primer

<400> SEQUENCE: 127
aatgtacagt attgcgtttt gcacagaccg tcatgcattt ctgacactc    49

<210> SEQ ID NO 128
<211> LENGTH: 47
<212> TYPE: DNA
<213> ORGANISM: Artificial Sequence
<220> FEATURE:

```
<223> OTHER INFORMATION: Primer

<400> SEQUENCE: 128
aatgtacagt attgcgtttt gaggctggta cctgctcttc ttcaatc                47

<210> SEQ ID NO 129
<211> LENGTH: 53
<212> TYPE: DNA
<213> ORGANISM: Artificial Sequence
<220> FEATURE:
<223> OTHER INFORMATION: Primer

<400> SEQUENCE: 129
aatgtacagt attgcgtttt gcgaaatcaa acagttgtct atcagagcct gtc         53

<210> SEQ ID NO 130
<211> LENGTH: 55
<212> TYPE: DNA
<213> ORGANISM: Artificial Sequence
<220> FEATURE:
<223> OTHER INFORMATION: Primer

<400> SEQUENCE: 130
aatgtacagt attgcgtttt gacaaaagaa aagaagtcat gtctgtatgt ggaaa       55

<210> SEQ ID NO 131
<211> LENGTH: 57
<212> TYPE: DNA
<213> ORGANISM: Artificial Sequence
<220> FEATURE:
<223> OTHER INFORMATION: Primer

<400> SEQUENCE: 131
aatgtacagt attgcgtttt gtccaggata atacacatca cagtaaataa cactctg     57

<210> SEQ ID NO 132
<211> LENGTH: 55
<212> TYPE: DNA
<213> ORGANISM: Artificial Sequence
<220> FEATURE:
<223> OTHER INFORMATION: Primer

<400> SEQUENCE: 132
aatgtacagt attgcgtttt gcatcctctt tgtcatcaag ctacagtctt tttga       55

<210> SEQ ID NO 133
<211> LENGTH: 51
<212> TYPE: DNA
<213> ORGANISM: Artificial Sequence
<220> FEATURE:
<223> OTHER INFORMATION: Primer

<400> SEQUENCE: 133
aatgtacagt attgcgtttt gctcccattt ttgtgcatct ttgttgctgt c           51

<210> SEQ ID NO 134
<211> LENGTH: 55
<212> TYPE: DNA
<213> ORGANISM: Artificial Sequence
<220> FEATURE:
<223> OTHER INFORMATION: Primer

<400> SEQUENCE: 134
aatgtacagt attgcgtttt gcagaactgc ctattcctaa ctgactcatc atttc       55
```

```
<210> SEQ ID NO 135
<211> LENGTH: 54
<212> TYPE: DNA
<213> ORGANISM: Artificial Sequence
<220> FEATURE:
<223> OTHER INFORMATION: Primer

<400> SEQUENCE: 135
aatgtacagt attgcgtttt ggaattctgt ttcatcgctg agtgacactc tttt        54

<210> SEQ ID NO 136
<211> LENGTH: 57
<212> TYPE: DNA
<213> ORGANISM: Artificial Sequence
<220> FEATURE:
<223> OTHER INFORMATION: Primer

<400> SEQUENCE: 136
aatgtacagt attgcgtttt gttttttacct tgcttttac ctttttgtac ttgtgac     57

<210> SEQ ID NO 137
<211> LENGTH: 53
<212> TYPE: DNA
<213> ORGANISM: Artificial Sequence
<220> FEATURE:
<223> OTHER INFORMATION: Primer

<400> SEQUENCE: 137
aatgtacagt attgcgtttt gagaaggagt ctggaataga aaggctaaca gaa         53

<210> SEQ ID NO 138
<211> LENGTH: 49
<212> TYPE: DNA
<213> ORGANISM: Artificial Sequence
<220> FEATURE:
<223> OTHER INFORMATION: Primer

<400> SEQUENCE: 138
aatgtacagt attgcgtttt gcacaagatg tgccaaggga attgtatgc              49

<210> SEQ ID NO 139
<211> LENGTH: 57
<212> TYPE: DNA
<213> ORGANISM: Artificial Sequence
<220> FEATURE:
<223> OTHER INFORMATION: Primer

<400> SEQUENCE: 139
aatgtacagt attgcgtttt gaagagtcaa taggtcagag agttttatgt tcttcca     57

<210> SEQ ID NO 140
<211> LENGTH: 52
<212> TYPE: DNA
<213> ORGANISM: Artificial Sequence
<220> FEATURE:
<223> OTHER INFORMATION: Primer

<400> SEQUENCE: 140
aatgtacagt attgcgtttt gactgatctt ctcaaagtcg tcatccttca gt          52

<210> SEQ ID NO 141
<211> LENGTH: 57
<212> TYPE: DNA
<213> ORGANISM: Artificial Sequence
<220> FEATURE:
<223> OTHER INFORMATION: Primer
```

```
<400> SEQUENCE: 141
aatgtacagt attgcgtttt gaccctgaga ataatccaa ttacctgtta atcaagg        57

<210> SEQ ID NO 142
<211> LENGTH: 57
<212> TYPE: DNA
<213> ORGANISM: Artificial Sequence
<220> FEATURE:
<223> OTHER INFORMATION: Primer

<400> SEQUENCE: 142
aatgtacagt attgcgtttt gaaaaggtat tgagtaaaat cagtcttcct tctaccc        57

<210> SEQ ID NO 143
<211> LENGTH: 55
<212> TYPE: DNA
<213> ORGANISM: Artificial Sequence
<220> FEATURE:
<223> OTHER INFORMATION: Primer

<400> SEQUENCE: 143
aatgtacagt attgcgtttt gccttcctcc ctctttcttt cataaaacct ctctt         55

<210> SEQ ID NO 144
<211> LENGTH: 45
<212> TYPE: DNA
<213> ORGANISM: Artificial Sequence
<220> FEATURE:
<223> OTHER INFORMATION: Primer

<400> SEQUENCE: 144
aatgtacagt attgcgtttt ggccagagcc acccaactct taagg                    45

<210> SEQ ID NO 145
<211> LENGTH: 57
<212> TYPE: DNA
<213> ORGANISM: Artificial Sequence
<220> FEATURE:
<223> OTHER INFORMATION: Primer

<400> SEQUENCE: 145
aatgtacagt attgcgtttt gtggaagagg aatttaataa cgaacgtttt aagagga       57

<210> SEQ ID NO 146
<211> LENGTH: 47
<212> TYPE: DNA
<213> ORGANISM: Artificial Sequence
<220> FEATURE:
<223> OTHER INFORMATION: Primer

<400> SEQUENCE: 146
aatgtacagt attgcgtttt ggcatctact gccgaggatg ttccaag                  47

<210> SEQ ID NO 147
<211> LENGTH: 46
<212> TYPE: DNA
<213> ORGANISM: Artificial Sequence
<220> FEATURE:
<223> OTHER INFORMATION: Primer

<400> SEQUENCE: 147
aatgtacagt attgcgtttt gcacagtgag ctcaagtgcg acatca                   46

<210> SEQ ID NO 148
<211> LENGTH: 43
```

```
<212> TYPE: DNA
<213> ORGANISM: Artificial Sequence
<220> FEATURE:
<223> OTHER INFORMATION: Primer

<400> SEQUENCE: 148
aatgtacagt attgcgtttt gccgactggc catctcctcg tag              43

<210> SEQ ID NO 149
<211> LENGTH: 45
<212> TYPE: DNA
<213> ORGANISM: Artificial Sequence
<220> FEATURE:
<223> OTHER INFORMATION: Primer

<400> SEQUENCE: 149
aatgtacagt attgcgtttt ggtaccagcg cgactacgag gagat            45

<210> SEQ ID NO 150
<211> LENGTH: 57
<212> TYPE: DNA
<213> ORGANISM: Artificial Sequence
<220> FEATURE:
<223> OTHER INFORMATION: Primer

<400> SEQUENCE: 150
aatgtacagt attgcgtttt gtcttttctg tcaaatggag atgatctctt ctgactc   57

<210> SEQ ID NO 151
<211> LENGTH: 48
<212> TYPE: DNA
<213> ORGANISM: Artificial Sequence
<220> FEATURE:
<223> OTHER INFORMATION: Primer

<400> SEQUENCE: 151
aatgtacagt attgcgtttt ggggagccca tcatctgcaa aaacatcc         48

<210> SEQ ID NO 152
<211> LENGTH: 52
<212> TYPE: DNA
<213> ORGANISM: Artificial Sequence
<220> FEATURE:
<223> OTHER INFORMATION: Primer

<400> SEQUENCE: 152
aatgtacagt attgcgtttt gaagctgaag aagatgtgga aaagtcccaa tg    52

<210> SEQ ID NO 153
<211> LENGTH: 47
<212> TYPE: DNA
<213> ORGANISM: Artificial Sequence
<220> FEATURE:
<223> OTHER INFORMATION: Primer

<400> SEQUENCE: 153
aatgtacagt attgcgtttt ggcgtgggat gttttttgcag atgatgg         47

<210> SEQ ID NO 154
<211> LENGTH: 44
<212> TYPE: DNA
<213> ORGANISM: Artificial Sequence
<220> FEATURE:
<223> OTHER INFORMATION: Primer

<400> SEQUENCE: 154
```

-continued aatgtacagt attgcgtttt gcgacgctga ggacgctatg gatg      44

<210> SEQ ID NO 155
<211> LENGTH: 43
<212> TYPE: DNA
<213> ORGANISM: Artificial Sequence
<220> FEATURE:
<223> OTHER INFORMATION: Primer

<400> SEQUENCE: 155
aatgtacagt attgcgtttt ggctgaggcg cgtcttcgag aag      43

<210> SEQ ID NO 156
<211> LENGTH: 44
<212> TYPE: DNA
<213> ORGANISM: Artificial Sequence
<220> FEATURE:
<223> OTHER INFORMATION: Primer

<400> SEQUENCE: 156
aatgtacagt attgcgtttt ggcgcttgtc gtgaaagcga acga      44

<210> SEQ ID NO 157
<211> LENGTH: 42
<212> TYPE: DNA
<213> ORGANISM: Artificial Sequence
<220> FEATURE:
<223> OTHER INFORMATION: Primer

<400> SEQUENCE: 157
aatgtacagt attgcgtttt ggctgcccgc ccagttgtta ct      42

<210> SEQ ID NO 158
<211> LENGTH: 51
<212> TYPE: DNA
<213> ORGANISM: Artificial Sequence
<220> FEATURE:
<223> OTHER INFORMATION: Primer

<400> SEQUENCE: 158
aatgtacagt attgcgtttt gagactctgg actgatgaag caattctgag t      51

<210> SEQ ID NO 159
<211> LENGTH: 48
<212> TYPE: DNA
<213> ORGANISM: Artificial Sequence
<220> FEATURE:
<223> OTHER INFORMATION: Primer

<400> SEQUENCE: 159
aatgtacagt attgcgtttt gtcaccggtg acaccttaaa accaaagc      48

<210> SEQ ID NO 160
<211> LENGTH: 50
<212> TYPE: DNA
<213> ORGANISM: Artificial Sequence
<220> FEATURE:
<223> OTHER INFORMATION: Primer

<400> SEQUENCE: 160
aatgtacagt attgcgtttt gggctccttt gtacctcctc catcttgatc      50

<210> SEQ ID NO 161
<211> LENGTH: 57
<212> TYPE: DNA
<213> ORGANISM: Artificial Sequence

```
<220> FEATURE:
<223> OTHER INFORMATION: Primer

<400> SEQUENCE: 161
aatgtacagt attgcgtttt ggtcagttgt ctaacaataa caaagatctg ctcttgg      57

<210> SEQ ID NO 162
<211> LENGTH: 49
<212> TYPE: DNA
<213> ORGANISM: Artificial Sequence
<220> FEATURE:
<223> OTHER INFORMATION: Primer

<400> SEQUENCE: 162
aatgtacagt attgcgtttt gggtgggcag caagaaaaag tccagtaaa               49

<210> SEQ ID NO 163
<211> LENGTH: 49
<212> TYPE: DNA
<213> ORGANISM: Artificial Sequence
<220> FEATURE:
<223> OTHER INFORMATION: Primer

<400> SEQUENCE: 163
aatgtacagt attgcgtttt ggccaaggct ttctctggca tgatctttt               49

<210> SEQ ID NO 164
<211> LENGTH: 55
<212> TYPE: DNA
<213> ORGANISM: Artificial Sequence
<220> FEATURE:
<223> OTHER INFORMATION: Primer

<400> SEQUENCE: 164
aatgtacagt attgcgtttt gggataactt tctcagcatt tccaccagtt tcaag        55

<210> SEQ ID NO 165
<211> LENGTH: 57
<212> TYPE: DNA
<213> ORGANISM: Artificial Sequence
<220> FEATURE:
<223> OTHER INFORMATION: Primer

<400> SEQUENCE: 165
aatgtacagt attgcgtttt gtgtccctaa gttgagtaaa atgatagaga atgagtc      57

<210> SEQ ID NO 166
<211> LENGTH: 50
<212> TYPE: DNA
<213> ORGANISM: Artificial Sequence
<220> FEATURE:
<223> OTHER INFORMATION: Primer

<400> SEQUENCE: 166
aatgtacagt attgcgtttt ggctgccaga atccagcat ccaaaatttg               50

<210> SEQ ID NO 167
<211> LENGTH: 51
<212> TYPE: DNA
<213> ORGANISM: Artificial Sequence
<220> FEATURE:
<223> OTHER INFORMATION: Primer

<400> SEQUENCE: 167
aatgtacagt attgcgtttt ggtcgctttc ttttcttagt gccaggaaac t            51
```

<210> SEQ ID NO 168
<211> LENGTH: 50
<212> TYPE: DNA
<213> ORGANISM: Artificial Sequence
<220> FEATURE:
<223> OTHER INFORMATION: Primer

<400> SEQUENCE: 168
aatgtacagt attgcgtttt gacagtcgag acgattcatg agggaacttc                    50

<210> SEQ ID NO 169
<211> LENGTH: 48
<212> TYPE: DNA
<213> ORGANISM: Artificial Sequence
<220> FEATURE:
<223> OTHER INFORMATION: Primer

<400> SEQUENCE: 169
aatgtacagt attgcgtttt gggaaagctc ggcgtgttgg ataagaag                      48

<210> SEQ ID NO 170
<211> LENGTH: 48
<212> TYPE: DNA
<213> ORGANISM: Artificial Sequence
<220> FEATURE:
<223> OTHER INFORMATION: Primer

<400> SEQUENCE: 170
aatgtacagt attgcgtttt gacgccacaa gtgactgaaa gttggaag                      48

<210> SEQ ID NO 171
<211> LENGTH: 50
<212> TYPE: DNA
<213> ORGANISM: Artificial Sequence
<220> FEATURE:
<223> OTHER INFORMATION: Primer

<400> SEQUENCE: 171
aatgtacagt attgcgtttt gtgatgggct ggagatttgg catagttttc                    50

<210> SEQ ID NO 172
<211> LENGTH: 50
<212> TYPE: DNA
<213> ORGANISM: Artificial Sequence
<220> FEATURE:
<223> OTHER INFORMATION: Primer

<400> SEQUENCE: 172
aatgtacagt attgcgtttt gctatgcacc cactttcaac acagttaggt                    50

<210> SEQ ID NO 173
<211> LENGTH: 47
<212> TYPE: DNA
<213> ORGANISM: Artificial Sequence
<220> FEATURE:
<223> OTHER INFORMATION: Primer

<400> SEQUENCE: 173
aatgtacagt attgcgtttt ggcttggtca gaagtgctgt tgttgtc                       47

<210> SEQ ID NO 174
<211> LENGTH: 47
<212> TYPE: DNA
<213> ORGANISM: Artificial Sequence
<220> FEATURE:
<223> OTHER INFORMATION: Primer

<400> SEQUENCE: 174
aatgtacagt attgcgttttt gcgtgggcca gaaagttgtc cacaatg                    47

<210> SEQ ID NO 175
<211> LENGTH: 52
<212> TYPE: DNA
<213> ORGANISM: Artificial Sequence
<220> FEATURE:
<223> OTHER INFORMATION: Primer

<400> SEQUENCE: 175
aatgtacagt attgcgttttt ggggatatgg attctcgtgg tagaaggtgt aa              52

<210> SEQ ID NO 176
<211> LENGTH: 54
<212> TYPE: DNA
<213> ORGANISM: Artificial Sequence
<220> FEATURE:
<223> OTHER INFORMATION: Primer

<400> SEQUENCE: 176
aatgtacagt attgcgttttt gctaatcacc aagttccaag tgttcagaat ctcc            54

<210> SEQ ID NO 177
<211> LENGTH: 55
<212> TYPE: DNA
<213> ORGANISM: Artificial Sequence
<220> FEATURE:
<223> OTHER INFORMATION: Primer

<400> SEQUENCE: 177
aatgtacagt attgcgttttt gaccgtaata accaaggttc atcataggca ttgat           55

<210> SEQ ID NO 178
<211> LENGTH: 49
<212> TYPE: DNA
<213> ORGANISM: Artificial Sequence
<220> FEATURE:
<223> OTHER INFORMATION: Primer

<400> SEQUENCE: 178
aatgtacagt attgcgttttt gtcccagtgg aagttactat gcaccctat                  49

<210> SEQ ID NO 179
<211> LENGTH: 54
<212> TYPE: DNA
<213> ORGANISM: Artificial Sequence
<220> FEATURE:
<223> OTHER INFORMATION: Primer

<400> SEQUENCE: 179
aatgtacagt attgcgttttt gtgcttatgc ttgtgtttgt gtttcctctt atgg            54

<210> SEQ ID NO 180
<211> LENGTH: 54
<212> TYPE: DNA
<213> ORGANISM: Artificial Sequence
<220> FEATURE:
<223> OTHER INFORMATION: Primer

<400> SEQUENCE: 180
aatgtacagt attgcgttttt ggcttctgtt tctccttatg cttgttcttc tcac            54

<210> SEQ ID NO 181

```
<211> LENGTH: 47
<212> TYPE: DNA
<213> ORGANISM: Artificial Sequence
<220> FEATURE:
<223> OTHER INFORMATION: Primer

<400> SEQUENCE: 181
aatgtacagt attgcgtttt gcctgagtgg tcttttgca ggcaaag                         47

<210> SEQ ID NO 182
<211> LENGTH: 47
<212> TYPE: DNA
<213> ORGANISM: Artificial Sequence
<220> FEATURE:
<223> OTHER INFORMATION: Primer

<400> SEQUENCE: 182
aatgtacagt attgcgtttt gccggccaca agcttctaa gaacaac                        47

<210> SEQ ID NO 183
<211> LENGTH: 47
<212> TYPE: DNA
<213> ORGANISM: Artificial Sequence
<220> FEATURE:
<223> OTHER INFORMATION: Primer

<400> SEQUENCE: 183
aatgtacagt attgcgtttt ggcggttcat cttgaaggct tggatgt                       47

<210> SEQ ID NO 184
<211> LENGTH: 51
<212> TYPE: DNA
<213> ORGANISM: Artificial Sequence
<220> FEATURE:
<223> OTHER INFORMATION: Primer

<400> SEQUENCE: 184
aatgtacagt attgcgtttt gttcagtgaa atgaaccctt cgaatgacaa g                  51

<210> SEQ ID NO 185
<211> LENGTH: 48
<212> TYPE: DNA
<213> ORGANISM: Artificial Sequence
<220> FEATURE:
<223> OTHER INFORMATION: Primer

<400> SEQUENCE: 185
aatgtacagt attgcgtttt gctcctcctc ctctttgcgt ttcttgtc                      48

<210> SEQ ID NO 186
<211> LENGTH: 51
<212> TYPE: DNA
<213> ORGANISM: Artificial Sequence
<220> FEATURE:
<223> OTHER INFORMATION: Primer

<400> SEQUENCE: 186
aatgtacagt attgcgtttt ggcagcagag aaacaaatga aggacaaaca g                  51

<210> SEQ ID NO 187
<211> LENGTH: 52
<212> TYPE: DNA
<213> ORGANISM: Artificial Sequence
<220> FEATURE:
<223> OTHER INFORMATION: Primer

<400> SEQUENCE: 187
```

```
aatgtacagt attgcgtttt gtaaggagga ggaagaagac aagaaacgca aa        52
```

<210> SEQ ID NO 188
<211> LENGTH: 50
<212> TYPE: DNA
<213> ORGANISM: Artificial Sequence
<220> FEATURE:
<223> OTHER INFORMATION: Primer

<400> SEQUENCE: 188

```
aatgtacagt attgcgtttt gtaaggcagg tctgtgagca caaaatttgg            50
```

<210> SEQ ID NO 189
<211> LENGTH: 45
<212> TYPE: DNA
<213> ORGANISM: Artificial Sequence
<220> FEATURE:
<223> OTHER INFORMATION: Primer

<400> SEQUENCE: 189

```
aatgtacagt attgcgtttt gtggagctga ccagtgacaa tgacc                 45
```

<210> SEQ ID NO 190
<211> LENGTH: 46
<212> TYPE: DNA
<213> ORGANISM: Artificial Sequence
<220> FEATURE:
<223> OTHER INFORMATION: Primer

<400> SEQUENCE: 190

```
aatgtacagt attgcgtttt gggccaagaa gtcggtggac aagaac                46
```

<210> SEQ ID NO 191
<211> LENGTH: 43
<212> TYPE: DNA
<213> ORGANISM: Artificial Sequence
<220> FEATURE:
<223> OTHER INFORMATION: Primer

<400> SEQUENCE: 191

```
aatgtacagt attgcgtttt ggcgcaggcg gtcattgtca ctg                   43
```

<210> SEQ ID NO 192
<211> LENGTH: 48
<212> TYPE: DNA
<213> ORGANISM: Artificial Sequence
<220> FEATURE:
<223> OTHER INFORMATION: Primer

<400> SEQUENCE: 192

```
aatgtacagt attgcgtttt gttgctgttc ttgtccaccg acttcttg              48
```

<210> SEQ ID NO 193
<211> LENGTH: 42
<212> TYPE: DNA
<213> ORGANISM: Artificial Sequence
<220> FEATURE:
<223> OTHER INFORMATION: Primer

<400> SEQUENCE: 193

```
aatgtacagt attgcgtttt ggcagtgcgc gatctggaac tg                    42
```

<210> SEQ ID NO 194
<211> LENGTH: 42
<212> TYPE: DNA

```
<213> ORGANISM: Artificial Sequence
<220> FEATURE:
<223> OTHER INFORMATION: Primer

<400> SEQUENCE: 194
aatgtacagt attgcgtttt gcggcggcga ctttgactac cc              42

<210> SEQ ID NO 195
<211> LENGTH: 45
<212> TYPE: DNA
<213> ORGANISM: Artificial Sequence
<220> FEATURE:
<223> OTHER INFORMATION: Primer

<400> SEQUENCE: 195
aatgtacagt attgcgtttt ggagcacgag acgtccatcg acatc           45

<210> SEQ ID NO 196
<211> LENGTH: 43
<212> TYPE: DNA
<213> ORGANISM: Artificial Sequence
<220> FEATURE:
<223> OTHER INFORMATION: Primer

<400> SEQUENCE: 196
aatgtacagt attgcgtttt gcggccagga actcgtcgtt gaa             43

<210> SEQ ID NO 197
<211> LENGTH: 45
<212> TYPE: DNA
<213> ORGANISM: Artificial Sequence
<220> FEATURE:
<223> OTHER INFORMATION: Primer

<400> SEQUENCE: 197
aatgtacagt attgcgtttt ggccatgccg ggagaactct aactc           45

<210> SEQ ID NO 198
<211> LENGTH: 54
<212> TYPE: DNA
<213> ORGANISM: Artificial Sequence
<220> FEATURE:
<223> OTHER INFORMATION: Primer

<400> SEQUENCE: 198
aatgtacagt attgcgtttt gtgtaaccct cctaagtgtt catacgttgt cttg 54

<210> SEQ ID NO 199
<211> LENGTH: 57
<212> TYPE: DNA
<213> ORGANISM: Artificial Sequence
<220> FEATURE:
<223> OTHER INFORMATION: Primer

<400> SEQUENCE: 199
aatgtacagt attgcgtttt ggtcttggtc tctgttatat cttgagtcta gaacagt 57

<210> SEQ ID NO 200
<211> LENGTH: 49
<212> TYPE: DNA
<213> ORGANISM: Artificial Sequence
<220> FEATURE:
<223> OTHER INFORMATION: Primer

<400> SEQUENCE: 200
aatgtacagt attgcgtttt gcaggagaac atggaggcga gaagaaaat       49
```

```
<210> SEQ ID NO 201
<211> LENGTH: 48
<212> TYPE: DNA
<213> ORGANISM: Artificial Sequence
<220> FEATURE:
<223> OTHER INFORMATION: Primer

<400> SEQUENCE: 201
aatgtacagt attgcgtttt ggggaaagat tggatgccgg gaatcaac          48

<210> SEQ ID NO 202
<211> LENGTH: 46
<212> TYPE: DNA
<213> ORGANISM: Artificial Sequence
<220> FEATURE:
<223> OTHER INFORMATION: Primer

<400> SEQUENCE: 202
aatgtacagt attgcgtttt gcggaggctt gattaggtag gaggtg            46

<210> SEQ ID NO 203
<211> LENGTH: 45
<212> TYPE: DNA
<213> ORGANISM: Artificial Sequence
<220> FEATURE:
<223> OTHER INFORMATION: Primer

<400> SEQUENCE: 203
aatgtacagt attgcgtttt ggcggcagct caacgagaat aaaca             45

<210> SEQ ID NO 204
<211> LENGTH: 45
<212> TYPE: DNA
<213> ORGANISM: Artificial Sequence
<220> FEATURE:
<223> OTHER INFORMATION: Primer

<400> SEQUENCE: 204
aatgtacagt attgcgtttt ggcccgcatc cttactccgc ttatc             45

<210> SEQ ID NO 205
<211> LENGTH: 49
<212> TYPE: DNA
<213> ORGANISM: Artificial Sequence
<220> FEATURE:
<223> OTHER INFORMATION: Primer

<400> SEQUENCE: 205
aatgtacagt attgcgtttt ggctggtttc aaggtaagtg gactcttcc         49

<210> SEQ ID NO 206
<211> LENGTH: 47
<212> TYPE: DNA
<213> ORGANISM: Artificial Sequence
<220> FEATURE:
<223> OTHER INFORMATION: Primer

<400> SEQUENCE: 206
aatgtacagt attgcgtttt ggggaatgac tgacggagaa tcccaac           47

<210> SEQ ID NO 207
<211> LENGTH: 48
<212> TYPE: DNA
<213> ORGANISM: Artificial Sequence
<220> FEATURE:
```

```
<223> OTHER INFORMATION: Primer

<400> SEQUENCE: 207
aatgtacagt attgcgtttt gctaagaccg agagcctgta ggagcttt          48

<210> SEQ ID NO 208
<211> LENGTH: 42
<212> TYPE: DNA
<213> ORGANISM: Artificial Sequence
<220> FEATURE:
<223> OTHER INFORMATION: Primer

<400> SEQUENCE: 208
aatgtacagt attgcgtttt ggccgggctt gtctggtcat ct                42

<210> SEQ ID NO 209
<211> LENGTH: 51
<212> TYPE: DNA
<213> ORGANISM: Artificial Sequence
<220> FEATURE:
<223> OTHER INFORMATION: Primer

<400> SEQUENCE: 209
aatgtacagt attgcgtttt gcagctcacc tccaaaaagg caaaattctt g       51

<210> SEQ ID NO 210
<211> LENGTH: 48
<212> TYPE: DNA
<213> ORGANISM: Artificial Sequence
<220> FEATURE:
<223> OTHER INFORMATION: Primer

<400> SEQUENCE: 210
aatgtacagt attgcgtttt ggcaggaggc catgatggat ttcttcaa          48

<210> SEQ ID NO 211
<211> LENGTH: 53
<212> TYPE: DNA
<213> ORGANISM: Artificial Sequence
<220> FEATURE:
<223> OTHER INFORMATION: Primer

<400> SEQUENCE: 211
aatgtacagt attgcgtttt gcatgagtga aaggaaagag gaaatcccaa tcc     53

<210> SEQ ID NO 212
<211> LENGTH: 56
<212> TYPE: DNA
<213> ORGANISM: Artificial Sequence
<220> FEATURE:
<223> OTHER INFORMATION: Primer

<400> SEQUENCE: 212
aatgtacagt attgcgtttt gcctatcttc cacagtactt acacaacttc ctaagc  56

<210> SEQ ID NO 213
<211> LENGTH: 45
<212> TYPE: DNA
<213> ORGANISM: Artificial Sequence
<220> FEATURE:
<223> OTHER INFORMATION: Primer

<400> SEQUENCE: 213
aatgtacagt attgcgtttt gctcgccgta gactgtccag gtttt            45
```

```
<210> SEQ ID NO 214
<211> LENGTH: 47
<212> TYPE: DNA
<213> ORGANISM: Artificial Sequence
<220> FEATURE:
<223> OTHER INFORMATION: Primer

<400> SEQUENCE: 214
aatgtacagt attgcgtttt gctcacctga tccgtgacgt tgatgtc          47

<210> SEQ ID NO 215
<211> LENGTH: 44
<212> TYPE: DNA
<213> ORGANISM: Artificial Sequence
<220> FEATURE:
<223> OTHER INFORMATION: Primer

<400> SEQUENCE: 215
aatgtacagt attgcgtttt ggccctgatg gactctcggc tact             44

<210> SEQ ID NO 216
<211> LENGTH: 53
<212> TYPE: DNA
<213> ORGANISM: Artificial Sequence
<220> FEATURE:
<223> OTHER INFORMATION: Primer

<400> SEQUENCE: 216
aatgtacagt attgcgtttt ggagaaagat caggaacact tgtcccctac tag   53

<210> SEQ ID NO 217
<211> LENGTH: 48
<212> TYPE: DNA
<213> ORGANISM: Artificial Sequence
<220> FEATURE:
<223> OTHER INFORMATION: Primer

<400> SEQUENCE: 217
aatgtacagt attgcgtttt ggtcctccac gatctcctca tactcctc         48

<210> SEQ ID NO 218
<211> LENGTH: 47
<212> TYPE: DNA
<213> ORGANISM: Artificial Sequence
<220> FEATURE:
<223> OTHER INFORMATION: Primer

<400> SEQUENCE: 218
aatgtacagt attgcgtttt gtcgatggac ttgacaagcc cgtactt          47

<210> SEQ ID NO 219
<211> LENGTH: 48
<212> TYPE: DNA
<213> ORGANISM: Artificial Sequence
<220> FEATURE:
<223> OTHER INFORMATION: Primer

<400> SEQUENCE: 219
aatgtacagt attgcgtttt gctggacgac gaggagtatg aggagatc         48

<210> SEQ ID NO 220
<211> LENGTH: 46
<212> TYPE: DNA
<213> ORGANISM: Artificial Sequence
<220> FEATURE:
<223> OTHER INFORMATION: Primer
```

<400> SEQUENCE: 220
aatgtacagt attgcgtttt gtaccagaag tcccggcggt gataag        46

<210> SEQ ID NO 221
<211> LENGTH: 49
<212> TYPE: DNA
<213> ORGANISM: Artificial Sequence
<220> FEATURE:
<223> OTHER INFORMATION: Primer

<400> SEQUENCE: 221
aatgtacagt attgcgtttt ggttcacctc tgtgtttgac tgccagaaa        49

<210> SEQ ID NO 222
<211> LENGTH: 57
<212> TYPE: DNA
<213> ORGANISM: Artificial Sequence
<220> FEATURE:
<223> OTHER INFORMATION: Primer

<400> SEQUENCE: 222
aatgtacagt attgcgtttt gcaatgagta ttctcttcat ttcaggtcag ttgattt        57

<210> SEQ ID NO 223
<211> LENGTH: 49
<212> TYPE: DNA
<213> ORGANISM: Artificial Sequence
<220> FEATURE:
<223> OTHER INFORMATION: Primer

<400> SEQUENCE: 223
aatgtacagt attgcgtttt gggctgcttt cttgaaggct attgggtat        49

<210> SEQ ID NO 224
<211> LENGTH: 53
<212> TYPE: DNA
<213> ORGANISM: Artificial Sequence
<220> FEATURE:
<223> OTHER INFORMATION: Primer

<400> SEQUENCE: 224
aatgtacagt attgcgtttt gaggagactg gaattctcga ataaggatta aca        53

<210> SEQ ID NO 225
<211> LENGTH: 57
<212> TYPE: DNA
<213> ORGANISM: Artificial Sequence
<220> FEATURE:
<223> OTHER INFORMATION: Primer

<400> SEQUENCE: 225
aatgtacagt attgcgtttt ggcatagtta aaacctgtgt ttggttttgt aggtctt        57

<210> SEQ ID NO 226
<211> LENGTH: 48
<212> TYPE: DNA
<213> ORGANISM: Artificial Sequence
<220> FEATURE:
<223> OTHER INFORMATION: Primer

<400> SEQUENCE: 226
aatgtacagt attgcgtttt gctctgtgtt ggcggatacc cttccata        48

<210> SEQ ID NO 227
<211> LENGTH: 53

```
<212> TYPE: DNA
<213> ORGANISM: Artificial Sequence
<220> FEATURE:
<223> OTHER INFORMATION: Primer

<400> SEQUENCE: 227
aatgtacagt attgcgtttt gggcattcct tctttattgc ccttcttaaa agc        53

<210> SEQ ID NO 228
<211> LENGTH: 50
<212> TYPE: DNA
<213> ORGANISM: Artificial Sequence
<220> FEATURE:
<223> OTHER INFORMATION: Primer

<400> SEQUENCE: 228
aatgtacagt attgcgtttt ggctgctggt ctggctacta tgatctctac             50

<210> SEQ ID NO 229
<211> LENGTH: 53
<212> TYPE: DNA
<213> ORGANISM: Artificial Sequence
<220> FEATURE:
<223> OTHER INFORMATION: Primer

<400> SEQUENCE: 229
aatgtacagt attgcgtttt ggcacacagc ttttaagaag gcaataaag aag         53

<210> SEQ ID NO 230
<211> LENGTH: 57
<212> TYPE: DNA
<213> ORGANISM: Artificial Sequence
<220> FEATURE:
<223> OTHER INFORMATION: Primer

<400> SEQUENCE: 230
aatgtacagt attgcgtttt gtgtatgttt aattctgtac atgagcattt catcagt    57

<210> SEQ ID NO 231
<211> LENGTH: 57
<212> TYPE: DNA
<213> ORGANISM: Artificial Sequence
<220> FEATURE:
<223> OTHER INFORMATION: Primer

<400> SEQUENCE: 231
aatgtacagt attgcgtttt gatttcatac cttgcttaat gggtgtagat accaaaa    57

<210> SEQ ID NO 232
<211> LENGTH: 48
<212> TYPE: DNA
<213> ORGANISM: Artificial Sequence
<220> FEATURE:
<223> OTHER INFORMATION: Primer

<400> SEQUENCE: 232
aatgtacagt attgcgtttt gttggcgtca aatgtgccac tatcactc               48

<210> SEQ ID NO 233
<211> LENGTH: 57
<212> TYPE: DNA
<213> ORGANISM: Artificial Sequence
<220> FEATURE:
<223> OTHER INFORMATION: Primer

<400> SEQUENCE: 233
```
aatgtacagt attgcgttttt gttctctttc aagctatgat ttaggcatag agaatcg        57

<210> SEQ ID NO 234
<211> LENGTH: 57
<212> TYPE: DNA
<213> ORGANISM: Artificial Sequence
<220> FEATURE:
<223> OTHER INFORMATION: Primer

<400> SEQUENCE: 234
aatgtacagt attgcgttttt gctgcagttg taggttataa ctatccattt gtctgaa        57

<210> SEQ ID NO 235
<211> LENGTH: 52
<212> TYPE: DNA
<213> ORGANISM: Artificial Sequence
<220> FEATURE:
<223> OTHER INFORMATION: Primer

<400> SEQUENCE: 235
aatgtacagt attgcgttttt gccctaggtc agatcaccca gtcagttaaa ac        52

<210> SEQ ID NO 236
<211> LENGTH: 52
<212> TYPE: DNA
<213> ORGANISM: Artificial Sequence
<220> FEATURE:
<223> OTHER INFORMATION: Primer

<400> SEQUENCE: 236
aatgtacagt attgcgttttt gtggttaaag gtcagcccac ttaccagata tg        52

<210> SEQ ID NO 237
<211> LENGTH: 49
<212> TYPE: DNA
<213> ORGANISM: Artificial Sequence
<220> FEATURE:
<223> OTHER INFORMATION: Primer

<400> SEQUENCE: 237
aatgtacagt attgcgttttt ggggtatgct ccccatttag aggataagg        49

<210> SEQ ID NO 238
<211> LENGTH: 50
<212> TYPE: DNA
<213> ORGANISM: Artificial Sequence
<220> FEATURE:
<223> OTHER INFORMATION: Primer

<400> SEQUENCE: 238
aatgtacagt attgcgttttt gacgtcagat ctacagcgaa cacaactact        50

<210> SEQ ID NO 239
<211> LENGTH: 50
<212> TYPE: DNA
<213> ORGANISM: Artificial Sequence
<220> FEATURE:
<223> OTHER INFORMATION: Primer

<400> SEQUENCE: 239
aatgtacagt attgcgttttt gagtggtgcc agactcacat tcagttctaa        50

<210> SEQ ID NO 240
<211> LENGTH: 54
<212> TYPE: DNA
<213> ORGANISM: Artificial Sequence

```
<220> FEATURE:
<223> OTHER INFORMATION: Primer

<400> SEQUENCE: 240
aatgtacagt attgcgtttt gcttggccag ttcctttctc taatgtatca tctc        54

<210> SEQ ID NO 241
<211> LENGTH: 56
<212> TYPE: DNA
<213> ORGANISM: Artificial Sequence
<220> FEATURE:
<223> OTHER INFORMATION: Primer

<400> SEQUENCE: 241
aatgtacagt attgcgtttt gaagttttct tgtctagtat cactttccct catagg      56

<210> SEQ ID NO 242
<211> LENGTH: 49
<212> TYPE: DNA
<213> ORGANISM: Artificial Sequence
<220> FEATURE:
<223> OTHER INFORMATION: Primer

<400> SEQUENCE: 242
aatgtacagt attgcgtttt ggggctcaac agatggtatg tgttctctg              49

<210> SEQ ID NO 243
<211> LENGTH: 54
<212> TYPE: DNA
<213> ORGANISM: Artificial Sequence
<220> FEATURE:
<223> OTHER INFORMATION: Primer

<400> SEQUENCE: 243
aatgtacagt attgcgtttt ggctctcgtt tctaacagtt ctttgcattg gata        54

<210> SEQ ID NO 244
<211> LENGTH: 50
<212> TYPE: DNA
<213> ORGANISM: Artificial Sequence
<220> FEATURE:
<223> OTHER INFORMATION: Primer

<400> SEQUENCE: 244
aatgtacagt attgcgtttt ggaggtgacc ttcaaagtca gaggctgtat             50

<210> SEQ ID NO 245
<211> LENGTH: 49
<212> TYPE: DNA
<213> ORGANISM: Artificial Sequence
<220> FEATURE:
<223> OTHER INFORMATION: Primer

<400> SEQUENCE: 245
aatgtacagt attgcgtttt ggagcaacca tcccatctgt ccttgtaac              49

<210> SEQ ID NO 246
<211> LENGTH: 50
<212> TYPE: DNA
<213> ORGANISM: Artificial Sequence
<220> FEATURE:
<223> OTHER INFORMATION: Primer

<400> SEQUENCE: 246
aatgtacagt attgcgtttt gggacaagga tgagaaaccc aattggaacc             50
```

<210> SEQ ID NO 247
<211> LENGTH: 46
<212> TYPE: DNA
<213> ORGANISM: Artificial Sequence
<220> FEATURE:
<223> OTHER INFORMATION: Primer

<400> SEQUENCE: 247
aatgtacagt attgcgtttt gcggtccgcc aaaagatccc agattc                46

<210> SEQ ID NO 248
<211> LENGTH: 46
<212> TYPE: DNA
<213> ORGANISM: Artificial Sequence
<220> FEATURE:
<223> OTHER INFORMATION: Primer

<400> SEQUENCE: 248
aatgtacagt attgcgtttt gggaggccac taacccactt gtgatg                46

<210> SEQ ID NO 249
<211> LENGTH: 54
<212> TYPE: DNA
<213> ORGANISM: Artificial Sequence
<220> FEATURE:
<223> OTHER INFORMATION: Primer

<400> SEQUENCE: 249
aatgtacagt attgcgtttt gtccagtttc ctagaggatg taatgggatt tgtc        54

<210> SEQ ID NO 250
<211> LENGTH: 52
<212> TYPE: DNA
<213> ORGANISM: Artificial Sequence
<220> FEATURE:
<223> OTHER INFORMATION: Primer

<400> SEQUENCE: 250
aatgtacagt attgcgtttt gtcacatttg gagatgagaa acgaggtgtt ct          52

<210> SEQ ID NO 251
<211> LENGTH: 48
<212> TYPE: DNA
<213> ORGANISM: Artificial Sequence
<220> FEATURE:
<223> OTHER INFORMATION: Primer

<400> SEQUENCE: 251
aatgtacagt attgcgtttt gcccttggcc tgtaacattg ctctgatc              48

<210> SEQ ID NO 252
<211> LENGTH: 52
<212> TYPE: DNA
<213> ORGANISM: Artificial Sequence
<220> FEATURE:
<223> OTHER INFORMATION: Primer

<400> SEQUENCE: 252
aatgtacagt attgcgtttt gcacctcgtt tctcatctcc aaatgtgatc tc          52

<210> SEQ ID NO 253
<211> LENGTH: 47
<212> TYPE: DNA
<213> ORGANISM: Artificial Sequence
<220> FEATURE:
<223> OTHER INFORMATION: Primer

<400> SEQUENCE: 253
aatgtacagt attgcgtttt gccagtagct ttcctgttct cggcatt                47

<210> SEQ ID NO 254
<211> LENGTH: 50
<212> TYPE: DNA
<213> ORGANISM: Artificial Sequence
<220> FEATURE:
<223> OTHER INFORMATION: Primer

<400> SEQUENCE: 254
aatgtacagt attgcgtttt ggcagcgtca agaatgagaa gacttttgtg             50

<210> SEQ ID NO 255
<211> LENGTH: 47
<212> TYPE: DNA
<213> ORGANISM: Artificial Sequence
<220> FEATURE:
<223> OTHER INFORMATION: Primer

<400> SEQUENCE: 255
aatgtacagt attgcgtttt gttgcccttc tggaaattac cccgaga              47

<210> SEQ ID NO 256
<211> LENGTH: 55
<212> TYPE: DNA
<213> ORGANISM: Artificial Sequence
<220> FEATURE:
<223> OTHER INFORMATION: Primer

<400> SEQUENCE: 256
aatgtacagt attgcgtttt gagttccacc agctttaatt attcctctag ctctc      55

<210> SEQ ID NO 257
<211> LENGTH: 56
<212> TYPE: DNA
<213> ORGANISM: Artificial Sequence
<220> FEATURE:
<223> OTHER INFORMATION: Primer

<400> SEQUENCE: 257
aatgtacagt attgcgtttt ggtttcccat ggccataatt tattatctca ccacaa     56

<210> SEQ ID NO 258
<211> LENGTH: 48
<212> TYPE: DNA
<213> ORGANISM: Artificial Sequence
<220> FEATURE:
<223> OTHER INFORMATION: Primer

<400> SEQUENCE: 258
aatgtacagt attgcgtttt ggtcacgatg actgtattgg accctcaa              48

<210> SEQ ID NO 259
<211> LENGTH: 56
<212> TYPE: DNA
<213> ORGANISM: Artificial Sequence
<220> FEATURE:
<223> OTHER INFORMATION: Primer

<400> SEQUENCE: 259
aatgtacagt attgcgtttt gtccagacct ttgctttaga ttggcaatta ttactg     56

<210> SEQ ID NO 260

```
<211> LENGTH: 51
<212> TYPE: DNA
<213> ORGANISM: Artificial Sequence
<220> FEATURE:
<223> OTHER INFORMATION: Primer

<400> SEQUENCE: 260
aatgtacagt attgcgtttt gccctaacaa cacagaagca aagcgttctt t            51

<210> SEQ ID NO 261
<211> LENGTH: 45
<212> TYPE: DNA
<213> ORGANISM: Artificial Sequence
<220> FEATURE:
<223> OTHER INFORMATION: Primer

<400> SEQUENCE: 261
aatgtacagt attgcgtttt gcgccctcct accacctgta ctacg                  45

<210> SEQ ID NO 262
<211> LENGTH: 46
<212> TYPE: DNA
<213> ORGANISM: Artificial Sequence
<220> FEATURE:
<223> OTHER INFORMATION: Primer

<400> SEQUENCE: 262
aatgtacagt attgcgtttt gactatccag gcgccttcac ctactc                 46

<210> SEQ ID NO 263
<211> LENGTH: 47
<212> TYPE: DNA
<213> ORGANISM: Artificial Sequence
<220> FEATURE:
<223> OTHER INFORMATION: Primer

<400> SEQUENCE: 263
aatgtacagt attgcgtttt gctcctaggc ggtatcatcc tgggtag                47

<210> SEQ ID NO 264
<211> LENGTH: 51
<212> TYPE: DNA
<213> ORGANISM: Artificial Sequence
<220> FEATURE:
<223> OTHER INFORMATION: Primer

<400> SEQUENCE: 264
aatgtacagt attgcgtttt gtctgattct cttcagatac aaggcagatc c           51

<210> SEQ ID NO 265
<211> LENGTH: 55
<212> TYPE: DNA
<213> ORGANISM: Artificial Sequence
<220> FEATURE:
<223> OTHER INFORMATION: Primer

<400> SEQUENCE: 265
aatgtacagt attgcgtttt ggcagatact tggacttgag taggcttatt aaacc       55

<210> SEQ ID NO 266
<211> LENGTH: 57
<212> TYPE: DNA
<213> ORGANISM: Artificial Sequence
<220> FEATURE:
<223> OTHER INFORMATION: Primer

<400> SEQUENCE: 266
```
aatgtacagt attgcgtttt ggcggctcta taaagaattg tccttatttt cgaactt    57

<210> SEQ ID NO 267
<211> LENGTH: 48
<212> TYPE: DNA
<213> ORGANISM: Artificial Sequence
<220> FEATURE:
<223> OTHER INFORMATION: Primer

<400> SEQUENCE: 267
aatgtacagt attgcgtttt ggttcgaggc ctttctctga gcatcaag    48

<210> SEQ ID NO 268
<211> LENGTH: 51
<212> TYPE: DNA
<213> ORGANISM: Artificial Sequence
<220> FEATURE:
<223> OTHER INFORMATION: Primer

<400> SEQUENCE: 268
aatgtacagt attgcgtttt gacatcggca gaaactagat gatcagacca a    51

<210> SEQ ID NO 269
<211> LENGTH: 57
<212> TYPE: DNA
<213> ORGANISM: Artificial Sequence
<220> FEATURE:
<223> OTHER INFORMATION: Primer

<400> SEQUENCE: 269
aatgtacagt attgcgtttt gtttaggaaa tccacaatac tttttctgat ctcttcc    57

<210> SEQ ID NO 270
<211> LENGTH: 53
<212> TYPE: DNA
<213> ORGANISM: Artificial Sequence
<220> FEATURE:
<223> OTHER INFORMATION: Primer

<400> SEQUENCE: 270
aatgtacagt attgcgtttt ggccaccaac ctcattctgt tttgttctct atc    53

<210> SEQ ID NO 271
<211> LENGTH: 51
<212> TYPE: DNA
<213> ORGANISM: Artificial Sequence
<220> FEATURE:
<223> OTHER INFORMATION: Primer

<400> SEQUENCE: 271
aatgtacagt attgcgtttt gctgcatttg tcctttgact ggtgtttagg t    51

<210> SEQ ID NO 272
<211> LENGTH: 52
<212> TYPE: DNA
<213> ORGANISM: Artificial Sequence
<220> FEATURE:
<223> OTHER INFORMATION: Primer

<400> SEQUENCE: 272
aatgtacagt attgcgtttt gcttcgaccg acaaacctga ggtcattaaa tc    52

<210> SEQ ID NO 273
<211> LENGTH: 46
<212> TYPE: DNA

```
<213> ORGANISM: Artificial Sequence
<220> FEATURE:
<223> OTHER INFORMATION: Primer

<400> SEQUENCE: 273
aatgtacagt attgcgtttt gccccacatc ccaagctagg aagacc          46

<210> SEQ ID NO 274
<211> LENGTH: 45
<212> TYPE: DNA
<213> ORGANISM: Artificial Sequence
<220> FEATURE:
<223> OTHER INFORMATION: Primer

<400> SEQUENCE: 274
aatgtacagt attgcgtttt gcgggccagt accttgaaag cgatg           45

<210> SEQ ID NO 275
<211> LENGTH: 51
<212> TYPE: DNA
<213> ORGANISM: Artificial Sequence
<220> FEATURE:
<223> OTHER INFORMATION: Primer

<400> SEQUENCE: 275
aatgtacagt attgcgtttt gctaactcaa tcggcttgtt gtgatgcgta t    51

<210> SEQ ID NO 276
<211> LENGTH: 51
<212> TYPE: DNA
<213> ORGANISM: Artificial Sequence
<220> FEATURE:
<223> OTHER INFORMATION: Primer

<400> SEQUENCE: 276
aatgtacagt attgcgtttt gccctcctgg actgttagta acttagtctc c    51

<210> SEQ ID NO 277
<211> LENGTH: 42
<212> TYPE: DNA
<213> ORGANISM: Artificial Sequence
<220> FEATURE:
<223> OTHER INFORMATION: Primer

<400> SEQUENCE: 277
aatgtacagt attgcgtttt gccctccgag ctccgcgaaa at              42

<210> SEQ ID NO 278
<211> LENGTH: 57
<212> TYPE: DNA
<213> ORGANISM: Artificial Sequence
<220> FEATURE:
<223> OTHER INFORMATION: Primer

<400> SEQUENCE: 278
aatgtacagt attgcgtttt ggtgctaaaa agtgtaagaa gaaatgagct agcaaaa   57

<210> SEQ ID NO 279
<211> LENGTH: 55
<212> TYPE: DNA
<213> ORGANISM: Artificial Sequence
<220> FEATURE:
<223> OTHER INFORMATION: Primer

<400> SEQUENCE: 279
aatgtacagt attgcgtttt gcatatgcct cagtttgaat tcctctcaca aacaa    55
```

<210> SEQ ID NO 280
<211> LENGTH: 51
<212> TYPE: DNA
<213> ORGANISM: Artificial Sequence
<220> FEATURE:
<223> OTHER INFORMATION: Primer

<400> SEQUENCE: 280
aatgtacagt attgcgtttt ggggagaaga aagagagatg tagggctaga g         51

<210> SEQ ID NO 281
<211> LENGTH: 54
<212> TYPE: DNA
<213> ORGANISM: Artificial Sequence
<220> FEATURE:
<223> OTHER INFORMATION: Primer

<400> SEQUENCE: 281
aatgtacagt attgcgtttt ggcaagcact tctgtttttg tcttttcagt ttcg      54

<210> SEQ ID NO 282
<211> LENGTH: 57
<212> TYPE: DNA
<213> ORGANISM: Artificial Sequence
<220> FEATURE:
<223> OTHER INFORMATION: Primer

<400> SEQUENCE: 282
aatgtacagt attgcgtttt gtctctgata tacttggatt ggtaattgag aaagtct   57

<210> SEQ ID NO 283
<211> LENGTH: 57
<212> TYPE: DNA
<213> ORGANISM: Artificial Sequence
<220> FEATURE:
<223> OTHER INFORMATION: Primer

<400> SEQUENCE: 283
aatgtacagt attgcgtttt ggtttgatat cttcccagca aaataatcag ctctcat   57

<210> SEQ ID NO 284
<211> LENGTH: 51
<212> TYPE: DNA
<213> ORGANISM: Artificial Sequence
<220> FEATURE:
<223> OTHER INFORMATION: Primer

<400> SEQUENCE: 284
aatgtacagt attgcgtttt gtagccaacc tcttttcgat gagctcacta g         51

<210> SEQ ID NO 285
<211> LENGTH: 51
<212> TYPE: DNA
<213> ORGANISM: Artificial Sequence
<220> FEATURE:
<223> OTHER INFORMATION: Primer

<400> SEQUENCE: 285
aatgtacagt attgcgtttt gtggaacaga caaactatcg actgaagttg t         51

<210> SEQ ID NO 286
<211> LENGTH: 48
<212> TYPE: DNA
<213> ORGANISM: Artificial Sequence
<220> FEATURE:

<223> OTHER INFORMATION: Primer

<400> SEQUENCE: 286
aatgtacagt attgcgtttt ggaggctgag tgcaaatttg gtctggaa  48

<210> SEQ ID NO 287
<211> LENGTH: 50
<212> TYPE: DNA
<213> ORGANISM: Artificial Sequence
<220> FEATURE:
<223> OTHER INFORMATION: Primer

<400> SEQUENCE: 287
aatgtacagt attgcgtttt ggatggtggt ggttgtctct gatgattacc  50

<210> SEQ ID NO 288
<211> LENGTH: 46
<212> TYPE: DNA
<213> ORGANISM: Artificial Sequence
<220> FEATURE:
<223> OTHER INFORMATION: Primer

<400> SEQUENCE: 288
aatgtacagt attgcgtttt ggcaaggcga gtccagaacc aagatt  46

<210> SEQ ID NO 289
<211> LENGTH: 47
<212> TYPE: DNA
<213> ORGANISM: Artificial Sequence
<220> FEATURE:
<223> OTHER INFORMATION: Primer

<400> SEQUENCE: 289
aatgtacagt attgcgtttt gtcagaagcg actgatcccc atcaagt  47

<210> SEQ ID NO 290
<211> LENGTH: 56
<212> TYPE: DNA
<213> ORGANISM: Artificial Sequence
<220> FEATURE:
<223> OTHER INFORMATION: Primer

<400> SEQUENCE: 290
aatgtacagt attgcgtttt gcatatggtc acatcacctt aactaaaccc atgttt  56

<210> SEQ ID NO 291
<211> LENGTH: 57
<212> TYPE: DNA
<213> ORGANISM: Artificial Sequence
<220> FEATURE:
<223> OTHER INFORMATION: Primer

<400> SEQUENCE: 291
aatgtacagt attgcgtttt gtttctcggt actgtttatt ttgaacaaaa ccaatcc  57

<210> SEQ ID NO 292
<211> LENGTH: 51
<212> TYPE: DNA
<213> ORGANISM: Artificial Sequence
<220> FEATURE:
<223> OTHER INFORMATION: Primer

<400> SEQUENCE: 292
aatgtacagt attgcgtttt gcctcctccc caaattccag gaacaatatg a  51

```
<210> SEQ ID NO 293
<211> LENGTH: 57
<212> TYPE: DNA
<213> ORGANISM: Artificial Sequence
<220> FEATURE:
<223> OTHER INFORMATION: Primer

<400> SEQUENCE: 293
aatgtacagt attgcgtttt gtgtgcgtca ttttatttgg gaaaatttga tactaac       57

<210> SEQ ID NO 294
<211> LENGTH: 46
<212> TYPE: DNA
<213> ORGANISM: Artificial Sequence
<220> FEATURE:
<223> OTHER INFORMATION: Primer

<400> SEQUENCE: 294
aatgtacagt attgcgtttt gcatgcagga gaagtcatcc cccttc                   46

<210> SEQ ID NO 295
<211> LENGTH: 51
<212> TYPE: DNA
<213> ORGANISM: Artificial Sequence
<220> FEATURE:
<223> OTHER INFORMATION: Primer

<400> SEQUENCE: 295
aatgtacagt attgcgtttt gtctgaaaac tggtggttgc ctctaggtta a             51

<210> SEQ ID NO 296
<211> LENGTH: 48
<212> TYPE: DNA
<213> ORGANISM: Artificial Sequence
<220> FEATURE:
<223> OTHER INFORMATION: Primer

<400> SEQUENCE: 296
aatgtacagt attgcgtttt ggccccttc ttgctcttct tggacttg                  48

<210> SEQ ID NO 297
<211> LENGTH: 48
<212> TYPE: DNA
<213> ORGANISM: Artificial Sequence
<220> FEATURE:
<223> OTHER INFORMATION: Primer

<400> SEQUENCE: 297
aatgtacagt attgcgtttt gccaagccaa gccaagctgg atattgtg                 48

<210> SEQ ID NO 298
<211> LENGTH: 49
<212> TYPE: DNA
<213> ORGANISM: Artificial Sequence
<220> FEATURE:
<223> OTHER INFORMATION: Primer

<400> SEQUENCE: 298
aatgtacagt attgcgtttt gcactcacat tgtgcagctt gtagtagag                49

<210> SEQ ID NO 299
<211> LENGTH: 48
<212> TYPE: DNA
<213> ORGANISM: Artificial Sequence
<220> FEATURE:
<223> OTHER INFORMATION: Primer
```

<400> SEQUENCE: 299
aatgtacagt attgcgtttt ggcaaagcgt ctgcatttga aggagttt        48

<210> SEQ ID NO 300
<211> LENGTH: 45
<212> TYPE: DNA
<213> ORGANISM: Artificial Sequence
<220> FEATURE:
<223> OTHER INFORMATION: Primer

<400> SEQUENCE: 300
aatgtacagt attgcgtttt gccctcccga gaacttgccg gttaa            45

<210> SEQ ID NO 301
<211> LENGTH: 46
<212> TYPE: DNA
<213> ORGANISM: Artificial Sequence
<220> FEATURE:
<223> OTHER INFORMATION: Primer

<400> SEQUENCE: 301
aatgtacagt attgcgtttt ggctccccac cacaaaaacg caaatg           46

<210> SEQ ID NO 302
<211> LENGTH: 48
<212> TYPE: DNA
<213> ORGANISM: Artificial Sequence
<220> FEATURE:
<223> OTHER INFORMATION: Primer

<400> SEQUENCE: 302
aatgtacagt attgcgtttt ggtgtcactg acggagagca tgaagatg         48

<210> SEQ ID NO 303
<211> LENGTH: 46
<212> TYPE: DNA
<213> ORGANISM: Artificial Sequence
<220> FEATURE:
<223> OTHER INFORMATION: Primer

<400> SEQUENCE: 303
aatgtacagt attgcgtttt gccacccaaa gaagtgtctc ctgacc           46

<210> SEQ ID NO 304
<211> LENGTH: 47
<212> TYPE: DNA
<213> ORGANISM: Artificial Sequence
<220> FEATURE:
<223> OTHER INFORMATION: Primer

<400> SEQUENCE: 304
aatgtacagt attgcgtttt gtccgtcagt gacacctggt acttgac          47

<210> SEQ ID NO 305
<211> LENGTH: 48
<212> TYPE: DNA
<213> ORGANISM: Artificial Sequence
<220> FEATURE:
<223> OTHER INFORMATION: Primer

<400> SEQUENCE: 305
aatgtacagt attgcgtttt gccctagctc tgcctaccct gatctttc         48

<210> SEQ ID NO 306
<211> LENGTH: 47

```
<212> TYPE: DNA
<213> ORGANISM: Artificial Sequence
<220> FEATURE:
<223> OTHER INFORMATION: Primer

<400> SEQUENCE: 306
aatgtacagt attgcgtttt gacgaggtgg acgtcttctt caatcac                47

<210> SEQ ID NO 307
<211> LENGTH: 43
<212> TYPE: DNA
<213> ORGANISM: Artificial Sequence
<220> FEATURE:
<223> OTHER INFORMATION: Primer

<400> SEQUENCE: 307
aatgtacagt attgcgtttt ggccctgcga gtcgaggtga ttg                    43

<210> SEQ ID NO 308
<211> LENGTH: 53
<212> TYPE: DNA
<213> ORGANISM: Artificial Sequence
<220> FEATURE:
<223> OTHER INFORMATION: Primer

<400> SEQUENCE: 308
aatgtacagt attgcgtttt gccatgactc tcaggaattg gccctatact tag         53

<210> SEQ ID NO 309
<211> LENGTH: 56
<212> TYPE: DNA
<213> ORGANISM: Artificial Sequence
<220> FEATURE:
<223> OTHER INFORMATION: Primer

<400> SEQUENCE: 309
aatgtacagt attgcgtttt gcttgggacc ttcatttcta tataacccct atctgg      56

<210> SEQ ID NO 310
<211> LENGTH: 49
<212> TYPE: DNA
<213> ORGANISM: Artificial Sequence
<220> FEATURE:
<223> OTHER INFORMATION: Primer

<400> SEQUENCE: 310
aatgtacagt attgcgtttt gtgccaggaa acttttcatt gtgcctctc              49

<210> SEQ ID NO 311
<211> LENGTH: 50
<212> TYPE: DNA
<213> ORGANISM: Artificial Sequence
<220> FEATURE:
<223> OTHER INFORMATION: Primer

<400> SEQUENCE: 311
aatgtacagt attgcgtttt ggttaccccca tggaacttac caagcactag            50

<210> SEQ ID NO 312
<211> LENGTH: 54
<212> TYPE: DNA
<213> ORGANISM: Artificial Sequence
<220> FEATURE:
<223> OTHER INFORMATION: Primer

<400> SEQUENCE: 312
```
aatgtacagt attgcgtttt ggtatgaaat tcgctggagg gtcattgaat caat        54

<210> SEQ ID NO 313
<211> LENGTH: 52
<212> TYPE: DNA
<213> ORGANISM: Artificial Sequence
<220> FEATURE:
<223> OTHER INFORMATION: Primer

<400> SEQUENCE: 313
aatgtacagt attgcgtttt gcaggaagga gcacttacgt tttagcatct tc        52

<210> SEQ ID NO 314
<211> LENGTH: 57
<212> TYPE: DNA
<213> ORGANISM: Artificial Sequence
<220> FEATURE:
<223> OTHER INFORMATION: Primer

<400> SEQUENCE: 314
aatgtacagt attgcgtttt ggattttgag aaattccctt aatatcccca tgctcaa        57

<210> SEQ ID NO 315
<211> LENGTH: 49
<212> TYPE: DNA
<213> ORGANISM: Artificial Sequence
<220> FEATURE:
<223> OTHER INFORMATION: Primer

<400> SEQUENCE: 315
aatgtacagt attgcgtttt gcacaaccac atgtgtccag tgaaaatcc        49

<210> SEQ ID NO 316
<211> LENGTH: 49
<212> TYPE: DNA
<213> ORGANISM: Artificial Sequence
<220> FEATURE:
<223> OTHER INFORMATION: Primer

<400> SEQUENCE: 316
aatgtacagt attgcgtttt gtgctttcat cagcagggtt caatccaaa        49

<210> SEQ ID NO 317
<211> LENGTH: 57
<212> TYPE: DNA
<213> ORGANISM: Artificial Sequence
<220> FEATURE:
<223> OTHER INFORMATION: Primer

<400> SEQUENCE: 317
aatgtacagt attgcgtttt gcatttacat catcacagag tattgcttct atggaga        57

<210> SEQ ID NO 318
<211> LENGTH: 56
<212> TYPE: DNA
<213> ORGANISM: Artificial Sequence
<220> FEATURE:
<223> OTHER INFORMATION: Primer

<400> SEQUENCE: 318
aatgtacagt attgcgtttt ggtgatctct ggatgtcgga atatttagaa acctct        56

<210> SEQ ID NO 319
<211> LENGTH: 57
<212> TYPE: DNA
<213> ORGANISM: Artificial Sequence

```
<220> FEATURE:
<223> OTHER INFORMATION: Primer

<400> SEQUENCE: 319
aatgtacagt attgcgtttt gatctttga aaacaatggt gactacatgg acatgaa        57

<210> SEQ ID NO 320
<211> LENGTH: 54
<212> TYPE: DNA
<213> ORGANISM: Artificial Sequence
<220> FEATURE:
<223> OTHER INFORMATION: Primer

<400> SEQUENCE: 320
aatgtacagt attgcgtttt gggtctaaaa aggtctgtgt tccttgaact taca           54

<210> SEQ ID NO 321
<211> LENGTH: 56
<212> TYPE: DNA
<213> ORGANISM: Artificial Sequence
<220> FEATURE:
<223> OTHER INFORMATION: Primer

<400> SEQUENCE: 321
aatgtacagt attgcgtttt gccagcacca atacatttaa tttctttct gcagac          56

<210> SEQ ID NO 322
<211> LENGTH: 51
<212> TYPE: DNA
<213> ORGANISM: Artificial Sequence
<220> FEATURE:
<223> OTHER INFORMATION: Primer

<400> SEQUENCE: 322
aatgtacagt attgcgtttt ggctacagat ggcttgatcc tgagtcattt c              51

<210> SEQ ID NO 323
<211> LENGTH: 48
<212> TYPE: DNA
<213> ORGANISM: Artificial Sequence
<220> FEATURE:
<223> OTHER INFORMATION: Primer

<400> SEQUENCE: 323
aatgtacagt attgcgtttt ggtcaggccc ataccaaggg aaaagatc                  48

<210> SEQ ID NO 324
<211> LENGTH: 51
<212> TYPE: DNA
<213> ORGANISM: Artificial Sequence
<220> FEATURE:
<223> OTHER INFORMATION: Primer

<400> SEQUENCE: 324
aatgtacagt attgcgtttt gacactgagt gatgtctggt cttatggcat t              51

<210> SEQ ID NO 325
<211> LENGTH: 50
<212> TYPE: DNA
<213> ORGANISM: Artificial Sequence
<220> FEATURE:
<223> OTHER INFORMATION: Primer

<400> SEQUENCE: 325
aatgtacagt attgcgtttt gcactgagcg tttgttagtc ctggtgtttt                50
```

-continued

<210> SEQ ID NO 326
<211> LENGTH: 53
<212> TYPE: DNA
<213> ORGANISM: Artificial Sequence
<220> FEATURE:
<223> OTHER INFORMATION: Primer

<400> SEQUENCE: 326
aatgtacagt attgcgtttt gcagattctc cacaatctca ctcaggtggt aaa        53

<210> SEQ ID NO 327
<211> LENGTH: 49
<212> TYPE: DNA
<213> ORGANISM: Artificial Sequence
<220> FEATURE:
<223> OTHER INFORMATION: Primer

<400> SEQUENCE: 327
aatgtacagt attgcgtttt gccccacagc tacgagatca tggtgaaat              49

<210> SEQ ID NO 328
<211> LENGTH: 57
<212> TYPE: DNA
<213> ORGANISM: Artificial Sequence
<220> FEATURE:
<223> OTHER INFORMATION: Primer

<400> SEQUENCE: 328
aatgtacagt attgcgtttt gtctctattc attttttgagg tttggttgtt aacactt    57

<210> SEQ ID NO 329
<211> LENGTH: 48
<212> TYPE: DNA
<213> ORGANISM: Artificial Sequence
<220> FEATURE:
<223> OTHER INFORMATION: Primer

<400> SEQUENCE: 329
aatgtacagt attgcgtttt ggggagtgca ccattatcgg gaaaatgg               48

<210> SEQ ID NO 330
<211> LENGTH: 56
<212> TYPE: DNA
<213> ORGANISM: Artificial Sequence
<220> FEATURE:
<223> OTHER INFORMATION: Primer

<400> SEQUENCE: 330
aatgtacagt attgcgtttt ggcttattct cattcgtttc atccaggatc tcaaaa      56

<210> SEQ ID NO 331
<211> LENGTH: 46
<212> TYPE: DNA
<213> ORGANISM: Artificial Sequence
<220> FEATURE:
<223> OTHER INFORMATION: Primer

<400> SEQUENCE: 331
aatgtacagt attgcgtttt ggggcgacga gattaggctg ttatgc                 46

<210> SEQ ID NO 332
<211> LENGTH: 49
<212> TYPE: DNA
<213> ORGANISM: Artificial Sequence
<220> FEATURE:
<223> OTHER INFORMATION: Primer -continued

<400> SEQUENCE: 332
aatgtacagt attgcgttttt gccctctgc attataagca gtgccaaaa       49

<210> SEQ ID NO 333
<211> LENGTH: 50
<212> TYPE: DNA
<213> ORGANISM: Artificial Sequence
<220> FEATURE:
<223> OTHER INFORMATION: Primer

<400> SEQUENCE: 333
aatgtacagt attgcgttttt ggcccacatc gttgtaagcc ttacattcaa       50

<210> SEQ ID NO 334
<211> LENGTH: 50
<212> TYPE: DNA
<213> ORGANISM: Artificial Sequence
<220> FEATURE:
<223> OTHER INFORMATION: Primer

<400> SEQUENCE: 334
aatgtacagt attgcgttttt gccgtttgga aagctagtgg ttcagagttc       50

<210> SEQ ID NO 335
<211> LENGTH: 50
<212> TYPE: DNA
<213> ORGANISM: Artificial Sequence
<220> FEATURE:
<223> OTHER INFORMATION: Primer

<400> SEQUENCE: 335
aatgtacagt attgcgttttt ggagatccca tcctgccaaa gtttgtgatt       50

<210> SEQ ID NO 336
<211> LENGTH: 50
<212> TYPE: DNA
<213> ORGANISM: Artificial Sequence
<220> FEATURE:
<223> OTHER INFORMATION: Primer

<400> SEQUENCE: 336
aatgtacagt attgcgttttt gggaaagccc ctgtttcata ctgaccaaaa       50

<210> SEQ ID NO 337
<211> LENGTH: 51
<212> TYPE: DNA
<213> ORGANISM: Artificial Sequence
<220> FEATURE:
<223> OTHER INFORMATION: Primer

<400> SEQUENCE: 337
aatgtacagt attgcgttttt gctttctccc cacagaaacc catgtatgaa g      51

<210> SEQ ID NO 338
<211> LENGTH: 51
<212> TYPE: DNA
<213> ORGANISM: Artificial Sequence
<220> FEATURE:
<223> OTHER INFORMATION: Primer

<400> SEQUENCE: 338
aatgtacagt attgcgttttt ggtttgccag ttgtgctttt tgctaaaatg c      51

<210> SEQ ID NO 339

-continued

<211> LENGTH: 48
<212> TYPE: DNA
<213> ORGANISM: Artificial Sequence
<220> FEATURE:
<223> OTHER INFORMATION: Primer

<400> SEQUENCE: 339
aatgtacagt attgcgtttt gccctcccac cctcaggact ataccaat          48

<210> SEQ ID NO 340
<211> LENGTH: 46
<212> TYPE: DNA
<213> ORGANISM: Artificial Sequence
<220> FEATURE:
<223> OTHER INFORMATION: Primer

<400> SEQUENCE: 340
aatgtacagt attgcgtttt gtgctcggca gattggtata gtcctg            46

<210> SEQ ID NO 341
<211> LENGTH: 50
<212> TYPE: DNA
<213> ORGANISM: Artificial Sequence
<220> FEATURE:
<223> OTHER INFORMATION: Primer

<400> SEQUENCE: 341
aatgtacagt attgcgtttt gggcatcctc tgtcctatct cccagataca        50

<210> SEQ ID NO 342
<211> LENGTH: 56
<212> TYPE: DNA
<213> ORGANISM: Artificial Sequence
<220> FEATURE:
<223> OTHER INFORMATION: Primer

<400> SEQUENCE: 342
aatgtacagt attgcgtttt gaggttttat actaaactta ctttgactgg gtttgg    56

<210> SEQ ID NO 343
<211> LENGTH: 45
<212> TYPE: DNA
<213> ORGANISM: Artificial Sequence
<220> FEATURE:
<223> OTHER INFORMATION: Primer

<400> SEQUENCE: 343
aatgtacagt attgcgtttt gcccccagag gtaagcgtca tatgg             45

<210> SEQ ID NO 344
<211> LENGTH: 49
<212> TYPE: DNA
<213> ORGANISM: Artificial Sequence
<220> FEATURE:
<223> OTHER INFORMATION: Primer

<400> SEQUENCE: 344
aatgtacagt attgcgtttt ggcacaggga agtaggtact gggagattg         49

<210> SEQ ID NO 345
<211> LENGTH: 48
<212> TYPE: DNA
<213> ORGANISM: Artificial Sequence
<220> FEATURE:
<223> OTHER INFORMATION: Primer

<400> SEQUENCE: 345

```
aatgtacagt attgcgtttt gaggcctgca aggttttaac tggaccta          48
```

<210> SEQ ID NO 346
<211> LENGTH: 49
<212> TYPE: DNA
<213> ORGANISM: Artificial Sequence
<220> FEATURE:
<223> OTHER INFORMATION: Primer

<400> SEQUENCE: 346

```
aatgtacagt attgcgtttt gcgggagctg ataagtggta cctgtatgt          49
```

<210> SEQ ID NO 347
<211> LENGTH: 49
<212> TYPE: DNA
<213> ORGANISM: Artificial Sequence
<220> FEATURE:
<223> OTHER INFORMATION: Primer

<400> SEQUENCE: 347

```
aatgtacagt attgcgtttt ggaaaagggt cccaggtagg tccagttaa          49
```

<210> SEQ ID NO 348
<211> LENGTH: 57
<212> TYPE: DNA
<213> ORGANISM: Artificial Sequence
<220> FEATURE:
<223> OTHER INFORMATION: Primer

<400> SEQUENCE: 348

```
aatgtacagt attgcgtttt gctctcggtg tatttctcta cttacctgta ataatgc          57
```

<210> SEQ ID NO 349
<211> LENGTH: 57
<212> TYPE: DNA
<213> ORGANISM: Artificial Sequence
<220> FEATURE:
<223> OTHER INFORMATION: Primer

<400> SEQUENCE: 349

```
aatgtacagt attgcgtttt gtttattgat gtctatgaag tgttgtggtt ccttaac          57
```

<210> SEQ ID NO 350
<211> LENGTH: 49
<212> TYPE: DNA
<213> ORGANISM: Artificial Sequence
<220> FEATURE:
<223> OTHER INFORMATION: Primer

<400> SEQUENCE: 350

```
aatgtacagt attgcgtttt gcagaaaaca agctgccgca aagttctac          49
```

<210> SEQ ID NO 351
<211> LENGTH: 48
<212> TYPE: DNA
<213> ORGANISM: Artificial Sequence
<220> FEATURE:
<223> OTHER INFORMATION: Primer

<400> SEQUENCE: 351

```
aatgtacagt attgcgtttt gcaggtgttg cgatgatgtc actgtacg          48
```

<210> SEQ ID NO 352
<211> LENGTH: 57
<212> TYPE: DNA

```
<213> ORGANISM: Artificial Sequence
<220> FEATURE:
<223> OTHER INFORMATION: Primer

<400> SEQUENCE: 352
aatgtacagt attgcgtttt gtcattttc attggacttg ttttgtcagc tttttgg      57

<210> SEQ ID NO 353
<211> LENGTH: 55
<212> TYPE: DNA
<213> ORGANISM: Artificial Sequence
<220> FEATURE:
<223> OTHER INFORMATION: Primer

<400> SEQUENCE: 353
aatgtacagt attgcgtttt ggttagcccc aatatgaaaa ataaagctgg ttgga        55

<210> SEQ ID NO 354
<211> LENGTH: 53
<212> TYPE: DNA
<213> ORGANISM: Artificial Sequence
<220> FEATURE:
<223> OTHER INFORMATION: Primer

<400> SEQUENCE: 354
aatgtacagt attgcgtttt gctggttgga ggttttgct aaatctggaa tga           53

<210> SEQ ID NO 355
<211> LENGTH: 57
<212> TYPE: DNA
<213> ORGANISM: Artificial Sequence
<220> FEATURE:
<223> OTHER INFORMATION: Primer

<400> SEQUENCE: 355
aatgtacagt attgcgtttt gttcttttg actagaaaac ttcagccact gtgtatt       57

<210> SEQ ID NO 356
<211> LENGTH: 55
<212> TYPE: DNA
<213> ORGANISM: Artificial Sequence
<220> FEATURE:
<223> OTHER INFORMATION: Primer

<400> SEQUENCE: 356
aatgtacagt attgcgtttt gcatatgacc aattgcagat gagcccatta ttgaa        55

<210> SEQ ID NO 357
<211> LENGTH: 51
<212> TYPE: DNA
<213> ORGANISM: Artificial Sequence
<220> FEATURE:
<223> OTHER INFORMATION: Primer

<400> SEQUENCE: 357
aatgtacagt attgcgtttt gaggcatagc tgactcatct atgtttgttc t            51

<210> SEQ ID NO 358
<211> LENGTH: 57
<212> TYPE: DNA
<213> ORGANISM: Artificial Sequence
<220> FEATURE:
<223> OTHER INFORMATION: Primer

<400> SEQUENCE: 358
aatgtacagt attgcgtttt gttcctcatt tctttcactc tgacagtata aaggtaa      57
```

<210> SEQ ID NO 359
<211> LENGTH: 54
<212> TYPE: DNA
<213> ORGANISM: Artificial Sequence
<220> FEATURE:
<223> OTHER INFORMATION: Primer

<400> SEQUENCE: 359
aatgtacagt attgcgtttt ggaactattc caacagaaca aaccgataac atca    54

<210> SEQ ID NO 360
<211> LENGTH: 53
<212> TYPE: DNA
<213> ORGANISM: Artificial Sequence
<220> FEATURE:
<223> OTHER INFORMATION: Primer

<400> SEQUENCE: 360
aatgtacagt attgcgtttt gtggatagca agacaattag agcccaactt agt    53

<210> SEQ ID NO 361
<211> LENGTH: 54
<212> TYPE: DNA
<213> ORGANISM: Artificial Sequence
<220> FEATURE:
<223> OTHER INFORMATION: Primer

<400> SEQUENCE: 361
aatgtacagt attgcgtttt gctactcctc ctgtctcttt ccacatcatc aatt    54

<210> SEQ ID NO 362
<211> LENGTH: 57
<212> TYPE: DNA
<213> ORGANISM: Artificial Sequence
<220> FEATURE:
<223> OTHER INFORMATION: Primer

<400> SEQUENCE: 362
aatgtacagt attgcgtttt gaggacctta tgttgtatgc tgtataaatc taaaggt    57

<210> SEQ ID NO 363
<211> LENGTH: 57
<212> TYPE: DNA
<213> ORGANISM: Artificial Sequence
<220> FEATURE:
<223> OTHER INFORMATION: Primer

<400> SEQUENCE: 363
aatgtacagt attgcgtttt ggtttgtcat cttctatggt aagtatcttt ctggatg    57

<210> SEQ ID NO 364
<211> LENGTH: 57
<212> TYPE: DNA
<213> ORGANISM: Artificial Sequence
<220> FEATURE:
<223> OTHER INFORMATION: Primer

<400> SEQUENCE: 364
aatgtacagt attgcgtttt gtggaggaga aacagataaa agttgagtat acgttta    57

<210> SEQ ID NO 365
<211> LENGTH: 54
<212> TYPE: DNA
<213> ORGANISM: Artificial Sequence
<220> FEATURE:

<223> OTHER INFORMATION: Primer

<400> SEQUENCE: 365
aatgtacagt attgcgttttt ggaggatgac gacatgttag taagcactac tact    54

<210> SEQ ID NO 366
<211> LENGTH: 57
<212> TYPE: DNA
<213> ORGANISM: Artificial Sequence
<220> FEATURE:
<223> OTHER INFORMATION: Primer

<400> SEQUENCE: 366
aatgtacagt attgcgttttt gattccacca tcatttcctt ctccaaaatt atcatcc    57

<210> SEQ ID NO 367
<211> LENGTH: 53
<212> TYPE: DNA
<213> ORGANISM: Artificial Sequence
<220> FEATURE:
<223> OTHER INFORMATION: Primer

<400> SEQUENCE: 367
aatgtacagt attgcgttttt gctcaaaagc actgccttct ctcattatct cac    53

<210> SEQ ID NO 368
<211> LENGTH: 57
<212> TYPE: DNA
<213> ORGANISM: Artificial Sequence
<220> FEATURE:
<223> OTHER INFORMATION: Primer

<400> SEQUENCE: 368
aatgtacagt attgcgttttt gaatgtattt gaccttcttt taaagtgaca tcgatgt    57

<210> SEQ ID NO 369
<211> LENGTH: 55
<212> TYPE: DNA
<213> ORGANISM: Artificial Sequence
<220> FEATURE:
<223> OTHER INFORMATION: Primer

<400> SEQUENCE: 369
aatgtacagt attgcgttttt gtgatgttcc caacttcttc tctcatggtt atctc    55

<210> SEQ ID NO 370
<211> LENGTH: 56
<212> TYPE: DNA
<213> ORGANISM: Artificial Sequence
<220> FEATURE:
<223> OTHER INFORMATION: Primer

<400> SEQUENCE: 370
aatgtacagt attgcgttttt gccctctgat ccctagataa tttatgggta gctaga    56

<210> SEQ ID NO 371
<211> LENGTH: 55
<212> TYPE: DNA
<213> ORGANISM: Artificial Sequence
<220> FEATURE:
<223> OTHER INFORMATION: Primer

<400> SEQUENCE: 371
aatgtacagt attgcgttttt gcacgaaatg caggttttgg aatatgatta atgtt    55

```
<210> SEQ ID NO 372
<211> LENGTH: 56
<212> TYPE: DNA
<213> ORGANISM: Artificial Sequence
<220> FEATURE:
<223> OTHER INFORMATION: Primer

<400> SEQUENCE: 372
aatgtacagt attgcgtttt ggaacaatgt tctacgcaca ttttgttctc agtaaa        56

<210> SEQ ID NO 373
<211> LENGTH: 50
<212> TYPE: DNA
<213> ORGANISM: Artificial Sequence
<220> FEATURE:
<223> OTHER INFORMATION: Primer

<400> SEQUENCE: 373
aatgtacagt attgcgtttt gtccacgctg ctctctaaat tacactcgaa               50

<210> SEQ ID NO 374
<211> LENGTH: 54
<212> TYPE: DNA
<213> ORGANISM: Artificial Sequence
<220> FEATURE:
<223> OTHER INFORMATION: Primer

<400> SEQUENCE: 374
aatgtacagt attgcgtttt gacgtagaac acatttcatt ttactcctct ttgg          54

<210> SEQ ID NO 375
<211> LENGTH: 57
<212> TYPE: DNA
<213> ORGANISM: Artificial Sequence
<220> FEATURE:
<223> OTHER INFORMATION: Primer

<400> SEQUENCE: 375
aatgtacagt attgcgtttt ggtcacatga atgtaaatca agaaaacaga tgttgtt       57

<210> SEQ ID NO 376
<211> LENGTH: 57
<212> TYPE: DNA
<213> ORGANISM: Artificial Sequence
<220> FEATURE:
<223> OTHER INFORMATION: Primer

<400> SEQUENCE: 376
aatgtacagt attgcgtttt gttctgaact atttatggac aacagtcaaa caacaat       57

<210> SEQ ID NO 377
<211> LENGTH: 57
<212> TYPE: DNA
<213> ORGANISM: Artificial Sequence
<220> FEATURE:
<223> OTHER INFORMATION: Primer

<400> SEQUENCE: 377
aatgtacagt attgcgtttt gtgaagccat tgcgagaact ttatccataa gtatttc       57

<210> SEQ ID NO 378
<211> LENGTH: 51
<212> TYPE: DNA
<213> ORGANISM: Artificial Sequence
<220> FEATURE:
<223> OTHER INFORMATION: Primer
```

```
<400> SEQUENCE: 378
aatgtacagt attgcgtttt ggccagagca catgaataaa tgagcatcca t         51

<210> SEQ ID NO 379
<211> LENGTH: 53
<212> TYPE: DNA
<213> ORGANISM: Artificial Sequence
<220> FEATURE:
<223> OTHER INFORMATION: Primer

<400> SEQUENCE: 379
aatgtacagt attgcgtttt gggaagctct cagggtacaa attctcagat cat       53

<210> SEQ ID NO 380
<211> LENGTH: 54
<212> TYPE: DNA
<213> ORGANISM: Artificial Sequence
<220> FEATURE:
<223> OTHER INFORMATION: Primer

<400> SEQUENCE: 380
aatgtacagt attgcgtttt gctcagggta caaattctca gatcatcagt cctc      54

<210> SEQ ID NO 381
<211> LENGTH: 49
<212> TYPE: DNA
<213> ORGANISM: Artificial Sequence
<220> FEATURE:
<223> OTHER INFORMATION: Primer

<400> SEQUENCE: 381
aatgtacagt attgcgtttt gctctacaca agcttccttt ccgtcatgc            49

<210> SEQ ID NO 382
<211> LENGTH: 52
<212> TYPE: DNA
<213> ORGANISM: Artificial Sequence
<220> FEATURE:
<223> OTHER INFORMATION: Primer

<400> SEQUENCE: 382
aatgtacagt attgcgtttt gcccttcaga tcttctcagc attcgagaga tc        52

<210> SEQ ID NO 383
<211> LENGTH: 49
<212> TYPE: DNA
<213> ORGANISM: Artificial Sequence
<220> FEATURE:
<223> OTHER INFORMATION: Primer

<400> SEQUENCE: 383
aatgtacagt attgcgtttt gaatcgaagc gctacctgat tccaattcc            49

<210> SEQ ID NO 384
<211> LENGTH: 46
<212> TYPE: DNA
<213> ORGANISM: Artificial Sequence
<220> FEATURE:
<223> OTHER INFORMATION: Primer

<400> SEQUENCE: 384
aatgtacagt attgcgtttt gccgaccgta actattcggt gcgttg                46

<210> SEQ ID NO 385
<211> LENGTH: 57
```

<212> TYPE: DNA
<213> ORGANISM: Artificial Sequence
<220> FEATURE:
<223> OTHER INFORMATION: Primer

<400> SEQUENCE: 385
aatgtacagt attgcgtttt gacattctat ccaagctgtg ttctatcttg agaaact    57

<210> SEQ ID NO 386
<211> LENGTH: 48
<212> TYPE: DNA
<213> ORGANISM: Artificial Sequence
<220> FEATURE:
<223> OTHER INFORMATION: Primer

<400> SEQUENCE: 386
aatgtacagt attgcgtttt gcgagtgagg gttttcgtgg ttcacatc    48

<210> SEQ ID NO 387
<211> LENGTH: 45
<212> TYPE: DNA
<213> ORGANISM: Artificial Sequence
<220> FEATURE:
<223> OTHER INFORMATION: Primer

<400> SEQUENCE: 387
aatgtacagt attgcgtttt gcgtgggtcc cagtctgcag ttaag    45

<210> SEQ ID NO 388
<211> LENGTH: 44
<212> TYPE: DNA
<213> ORGANISM: Artificial Sequence
<220> FEATURE:
<223> OTHER INFORMATION: Primer

<400> SEQUENCE: 388
aatgtacagt attgcgtttt ggctcagagc cgttccgaga tctt    44

<210> SEQ ID NO 389
<211> LENGTH: 48
<212> TYPE: DNA
<213> ORGANISM: Artificial Sequence
<220> FEATURE:
<223> OTHER INFORMATION: Primer

<400> SEQUENCE: 389
aatgtacagt attgcgtttt ggcgttccat ctcccacttg tcgtagtt    48

<210> SEQ ID NO 390
<211> LENGTH: 49
<212> TYPE: DNA
<213> ORGANISM: Artificial Sequence
<220> FEATURE:
<223> OTHER INFORMATION: Primer

<400> SEQUENCE: 390
aatgtacagt attgcgtttt gctggccgag ttggttcatc atcattcaa    49

<210> SEQ ID NO 391
<211> LENGTH: 48
<212> TYPE: DNA
<213> ORGANISM: Artificial Sequence
<220> FEATURE:
<223> OTHER INFORMATION: Primer

<400> SEQUENCE: 391
aatgtacagt attgcgtttt gtatggtgtg tcccccaact acgacaag          48

<210> SEQ ID NO 392
<211> LENGTH: 57
<212> TYPE: DNA
<213> ORGANISM: Artificial Sequence
<220> FEATURE:
<223> OTHER INFORMATION: Primer

<400> SEQUENCE: 392
aatgtacagt attgcgtttt gtgaaaagca cttcctgaaa taatttcacc ttcgttt     57

<210> SEQ ID NO 393
<211> LENGTH: 47
<212> TYPE: DNA
<213> ORGANISM: Artificial Sequence
<220> FEATURE:
<223> OTHER INFORMATION: Primer

<400> SEQUENCE: 393
aatgtacagt attgcgtttt gaggtactcc atggctgacg agatctg           47

<210> SEQ ID NO 394
<211> LENGTH: 48
<212> TYPE: DNA
<213> ORGANISM: Artificial Sequence
<220> FEATURE:
<223> OTHER INFORMATION: Primer

<400> SEQUENCE: 394
aatgtacagt attgcgtttt gttgcctttg ttccaaggtc caatgtgt          48

<210> SEQ ID NO 395
<211> LENGTH: 43
<212> TYPE: DNA
<213> ORGANISM: Artificial Sequence
<220> FEATURE:
<223> OTHER INFORMATION: Primer

<400> SEQUENCE: 395
aatgtacagt attgcgtttt gcgtccccgc attccaacgt ctc               43

<210> SEQ ID NO 396
<211> LENGTH: 42
<212> TYPE: DNA
<213> ORGANISM: Artificial Sequence
<220> FEATURE:
<223> OTHER INFORMATION: Primer

<400> SEQUENCE: 396
aatgtacagt attgcgtttt gggcgcgccg tttacttgaa gg                42

<210> SEQ ID NO 397
<211> LENGTH: 44
<212> TYPE: DNA
<213> ORGANISM: Artificial Sequence
<220> FEATURE:
<223> OTHER INFORMATION: Primer

<400> SEQUENCE: 397
aatgtacagt attgcgtttt ggcctggcgg tgcacactat tctg              44

<210> SEQ ID NO 398
<211> LENGTH: 48
<212> TYPE: DNA
<213> ORGANISM: Artificial Sequence

```
<220> FEATURE:
<223> OTHER INFORMATION: Primer

<400> SEQUENCE: 398
aatgtacagt attgcgttttt gaggtgcagc cacaaaactt acagatgc          48

<210> SEQ ID NO 399
<211> LENGTH: 45
<212> TYPE: DNA
<213> ORGANISM: Artificial Sequence
<220> FEATURE:
<223> OTHER INFORMATION: Primer

<400> SEQUENCE: 399
aatgtacagt attgcgttttt ggtgccgaac caatacaacc ctctg             45

<210> SEQ ID NO 400
<211> LENGTH: 43
<212> TYPE: DNA
<213> ORGANISM: Artificial Sequence
<220> FEATURE:
<223> OTHER INFORMATION: Primer

<400> SEQUENCE: 400
aatgtacagt attgcgttttt ggggcgggtc caccagtttg aat               43

<210> SEQ ID NO 401
<211> LENGTH: 44
<212> TYPE: DNA
<213> ORGANISM: Artificial Sequence
<220> FEATURE:
<223> OTHER INFORMATION: Primer

<400> SEQUENCE: 401
aatgtacagt attgcgttttt gccgcagagg gttgtattgg ttcg              44

<210> SEQ ID NO 402
<211> LENGTH: 47
<212> TYPE: DNA
<213> ORGANISM: Artificial Sequence
<220> FEATURE:
<223> OTHER INFORMATION: Primer

<400> SEQUENCE: 402
aatgtacagt attgcgttttt gagccactcg cattgaccat tcaaact           47

<210> SEQ ID NO 403
<211> LENGTH: 44
<212> TYPE: DNA
<213> ORGANISM: Artificial Sequence
<220> FEATURE:
<223> OTHER INFORMATION: Primer

<400> SEQUENCE: 403
aatgtacagt attgcgttttt gccacgtctg acaggtagcc atgg              44

<210> SEQ ID NO 404
<211> LENGTH: 45
<212> TYPE: DNA
<213> ORGANISM: Artificial Sequence
<220> FEATURE:
<223> OTHER INFORMATION: Primer

<400> SEQUENCE: 404
aatgtacagt attgcgttttt ggtgaggctg ctggacgagt acaac             45
```

<210> SEQ ID NO 405
<211> LENGTH: 43
<212> TYPE: DNA
<213> ORGANISM: Artificial Sequence
<220> FEATURE:
<223> OTHER INFORMATION: Primer

<400> SEQUENCE: 405
aatgtacagt attgcgtttt gcgcaccagg ttgtactcgt cca                43

<210> SEQ ID NO 406
<211> LENGTH: 46
<212> TYPE: DNA
<213> ORGANISM: Artificial Sequence
<220> FEATURE:
<223> OTHER INFORMATION: Primer

<400> SEQUENCE: 406
aatgtacagt attgcgtttt gccgcctttg tgcttctgtt cttcgt             46

<210> SEQ ID NO 407
<211> LENGTH: 57
<212> TYPE: DNA
<213> ORGANISM: Artificial Sequence
<220> FEATURE:
<223> OTHER INFORMATION: Primer

<400> SEQUENCE: 407
aatgtacagt attgcgtttt gctgattaat cgcgtagaaa atgaccttat tttggag    57

<210> SEQ ID NO 408
<211> LENGTH: 49
<212> TYPE: DNA
<213> ORGANISM: Artificial Sequence
<220> FEATURE:
<223> OTHER INFORMATION: Primer

<400> SEQUENCE: 408
aatgtacagt attgcgtttt ggctccatcg tctacctgga gattgacaa          49

<210> SEQ ID NO 409
<211> LENGTH: 45
<212> TYPE: DNA
<213> ORGANISM: Artificial Sequence
<220> FEATURE:
<223> OTHER INFORMATION: Primer

<400> SEQUENCE: 409
aatgtacagt attgcgtttt gtctgcacgg cctcgatctt gtagg              45

<210> SEQ ID NO 410
<211> LENGTH: 48
<212> TYPE: DNA
<213> ORGANISM: Artificial Sequence
<220> FEATURE:
<223> OTHER INFORMATION: Primer

<400> SEQUENCE: 410
aatgtacagt attgcgtttt ggccagcaga tgatcttccc ctactacg           48

<210> SEQ ID NO 411
<211> LENGTH: 44
<212> TYPE: DNA
<213> ORGANISM: Artificial Sequence
<220> FEATURE:
<223> OTHER INFORMATION: Primer

<400> SEQUENCE: 411
aatgtacagt attgcgtttt gcgtcacgct tgaagaccac gttg                    44

<210> SEQ ID NO 412
<211> LENGTH: 45
<212> TYPE: DNA
<213> ORGANISM: Artificial Sequence
<220> FEATURE:
<223> OTHER INFORMATION: Primer

<400> SEQUENCE: 412
aatgtacagt attgcgtttt ggccagcatg cagttctaag gctct                   45

<210> SEQ ID NO 413
<211> LENGTH: 43
<212> TYPE: DNA
<213> ORGANISM: Artificial Sequence
<220> FEATURE:
<223> OTHER INFORMATION: Primer

<400> SEQUENCE: 413
aatgtacagt attgcgtttt ggtgcccgtc tcgactctta ggc                     43

<210> SEQ ID NO 414
<211> LENGTH: 49
<212> TYPE: DNA
<213> ORGANISM: Artificial Sequence
<220> FEATURE:
<223> OTHER INFORMATION: Primer

<400> SEQUENCE: 414
aatgtacagt attgcgtttt gtgtagccgc tgatcgtcgt gtatatgtc               49

<210> SEQ ID NO 415
<211> LENGTH: 57
<212> TYPE: DNA
<213> ORGANISM: Artificial Sequence
<220> FEATURE:
<223> OTHER INFORMATION: Primer

<400> SEQUENCE: 415
aatgtacagt attgcgtttt ggactggtac tggttagtaa aggttgataa tattcca      57

<210> SEQ ID NO 416
<211> LENGTH: 57
<212> TYPE: DNA
<213> ORGANISM: Artificial Sequence
<220> FEATURE:
<223> OTHER INFORMATION: Primer

<400> SEQUENCE: 416
aatgtacagt attgcgtttt gggtgaagta atcagtttgt tcactagtta cgtgatt      57

<210> SEQ ID NO 417
<211> LENGTH: 57
<212> TYPE: DNA
<213> ORGANISM: Artificial Sequence
<220> FEATURE:
<223> OTHER INFORMATION: Primer

<400> SEQUENCE: 417
aatgtacagt attgcgtttt gctgacatgc ctactgatta ttcttcaaac tcatcac      57

<210> SEQ ID NO 418

-continued

```
<211> LENGTH: 57
<212> TYPE: DNA
<213> ORGANISM: Artificial Sequence
<220> FEATURE:
<223> OTHER INFORMATION: Primer

<400> SEQUENCE: 418
aatgtacagt attgcgttttt gtgtgtgttt taattgttcc acttgagatt cttaacc      57

<210> SEQ ID NO 419
<211> LENGTH: 57
<212> TYPE: DNA
<213> ORGANISM: Artificial Sequence
<220> FEATURE:
<223> OTHER INFORMATION: Primer

<400> SEQUENCE: 419
aatgtacagt attgcgttttt gcgtcagcat tttgaatcac ttcattctga catgata      57

<210> SEQ ID NO 420
<211> LENGTH: 57
<212> TYPE: DNA
<213> ORGANISM: Artificial Sequence
<220> FEATURE:
<223> OTHER INFORMATION: Primer

<400> SEQUENCE: 420
aatgtacagt attgcgttttt gagtaatttt caactattgg cctagtgaat ttaagct      57

<210> SEQ ID NO 421
<211> LENGTH: 55
<212> TYPE: DNA
<213> ORGANISM: Artificial Sequence
<220> FEATURE:
<223> OTHER INFORMATION: Primer

<400> SEQUENCE: 421
aatgtacagt attgcgttttt gagaaagagg gaagtcacat ttatagagtg ctagc        55

<210> SEQ ID NO 422
<211> LENGTH: 57
<212> TYPE: DNA
<213> ORGANISM: Artificial Sequence
<220> FEATURE:
<223> OTHER INFORMATION: Primer

<400> SEQUENCE: 422
aatgtacagt attgcgttttt gcatcaacag aaacagaaca caaactgtg acaaatc       57

<210> SEQ ID NO 423
<211> LENGTH: 57
<212> TYPE: DNA
<213> ORGANISM: Artificial Sequence
<220> FEATURE:
<223> OTHER INFORMATION: Primer

<400> SEQUENCE: 423
aatgtacagt attgcgttttt gccaaagaat atccctttat atagcagtgg aacaatt      57

<210> SEQ ID NO 424
<211> LENGTH: 55
<212> TYPE: DNA
<213> ORGANISM: Artificial Sequence
<220> FEATURE:
<223> OTHER INFORMATION: Primer

<400> SEQUENCE: 424
```

-continued aatgtacagt attgcgtttt gcagaatatg cagtgataag tgctgtttca tcact     55

<210> SEQ ID NO 425
<211> LENGTH: 48
<212> TYPE: DNA
<213> ORGANISM: Artificial Sequence
<220> FEATURE:
<223> OTHER INFORMATION: Primer

<400> SEQUENCE: 425
aatgtacagt attgcgtttt gttccccctg tgacgactac ttttcctc     48

<210> SEQ ID NO 426
<211> LENGTH: 48
<212> TYPE: DNA
<213> ORGANISM: Artificial Sequence
<220> FEATURE:
<223> OTHER INFORMATION: Primer

<400> SEQUENCE: 426
aatgtacagt attgcgtttt gcggtcccta tttcttcctc tgcttcgt     48

<210> SEQ ID NO 427
<211> LENGTH: 52
<212> TYPE: DNA
<213> ORGANISM: Artificial Sequence
<220> FEATURE:
<223> OTHER INFORMATION: Primer

<400> SEQUENCE: 427
aatgtacagt attgcgtttt gctgaacagt tctgtctcta ttacccgacc tc     52

<210> SEQ ID NO 428
<211> LENGTH: 52
<212> TYPE: DNA
<213> ORGANISM: Artificial Sequence
<220> FEATURE:
<223> OTHER INFORMATION: Primer

<400> SEQUENCE: 428
aatgtacagt attgcgtttt gcgttcatag ccttctatcc gagtatgtag ca     52

<210> SEQ ID NO 429
<211> LENGTH: 47
<212> TYPE: DNA
<213> ORGANISM: Artificial Sequence
<220> FEATURE:
<223> OTHER INFORMATION: Primer

<400> SEQUENCE: 429
aatgtacagt attgcgtttt gccccttctg tcctcgcagg ttaatcc     47

<210> SEQ ID NO 430
<211> LENGTH: 53
<212> TYPE: DNA
<213> ORGANISM: Artificial Sequence
<220> FEATURE:
<223> OTHER INFORMATION: Primer

<400> SEQUENCE: 430
aatgtacagt attgcgtttt ggcttccagc catttctgag atatcctcac agt     53

<210> SEQ ID NO 431
<211> LENGTH: 52
<212> TYPE: DNA

```
<213> ORGANISM: Artificial Sequence
<220> FEATURE:
<223> OTHER INFORMATION: Primer

<400> SEQUENCE: 431
aatgtacagt attgcgtttt gaccaggagg aacaaagaca catgaagatc at        52

<210> SEQ ID NO 432
<211> LENGTH: 45
<212> TYPE: DNA
<213> ORGANISM: Artificial Sequence
<220> FEATURE:
<223> OTHER INFORMATION: Primer

<400> SEQUENCE: 432
aatgtacagt attgcgtttt ggcgcccccg agtttcttac gaatc                45

<210> SEQ ID NO 433
<211> LENGTH: 57
<212> TYPE: DNA
<213> ORGANISM: Artificial Sequence
<220> FEATURE:
<223> OTHER INFORMATION: Primer

<400> SEQUENCE: 433
aatgtacagt attgcgtttt gtttatacac agtttggagt ttgagaatca gaagact   57

<210> SEQ ID NO 434
<211> LENGTH: 57
<212> TYPE: DNA
<213> ORGANISM: Artificial Sequence
<220> FEATURE:
<223> OTHER INFORMATION: Primer

<400> SEQUENCE: 434
aatgtacagt attgcgtttt gggttatctc tggctgatga gattatgagt gattctc   57

<210> SEQ ID NO 435
<211> LENGTH: 51
<212> TYPE: DNA
<213> ORGANISM: Artificial Sequence
<220> FEATURE:
<223> OTHER INFORMATION: Primer

<400> SEQUENCE: 435
aatgtacagt attgcgtttt ggccaagcta gtgattgatg tgattcgcta t         51

<210> SEQ ID NO 436
<211> LENGTH: 47
<212> TYPE: DNA
<213> ORGANISM: Artificial Sequence
<220> FEATURE:
<223> OTHER INFORMATION: Primer

<400> SEQUENCE: 436
aatgtacagt attgcgtttt gccctcctc tagtactccc tgtttgt               47

<210> SEQ ID NO 437
<211> LENGTH: 51
<212> TYPE: DNA
<213> ORGANISM: Artificial Sequence
<220> FEATURE:
<223> OTHER INFORMATION: Primer

<400> SEQUENCE: 437
aatgtacagt attgcgtttt gctccttcct gtcccaatca actagtctag c         51
```

<210> SEQ ID NO 438
<211> LENGTH: 46
<212> TYPE: DNA
<213> ORGANISM: Artificial Sequence
<220> FEATURE:
<223> OTHER INFORMATION: Primer

<400> SEQUENCE: 438
aatgtacagt attgcgtttt ggcctcgtcc ctcttccctt aggtaa                    46

<210> SEQ ID NO 439
<211> LENGTH: 55
<212> TYPE: DNA
<213> ORGANISM: Artificial Sequence
<220> FEATURE:
<223> OTHER INFORMATION: Primer

<400> SEQUENCE: 439
aatgtacagt attgcgtttt gtctctcttc ccattagtct gagtactgag tgatt          55

<210> SEQ ID NO 440
<211> LENGTH: 56
<212> TYPE: DNA
<213> ORGANISM: Artificial Sequence
<220> FEATURE:
<223> OTHER INFORMATION: Primer

<400> SEQUENCE: 440
aatgtacagt attgcgtttt gagcatttct tgagacttaa agtggcattc taaagg         56

<210> SEQ ID NO 441
<211> LENGTH: 57
<212> TYPE: DNA
<213> ORGANISM: Artificial Sequence
<220> FEATURE:
<223> OTHER INFORMATION: Primer

<400> SEQUENCE: 441
aatgtacagt attgcgtttt gatttttatt ctcaagaggc agaaatacca acttacc        57

<210> SEQ ID NO 442
<211> LENGTH: 57
<212> TYPE: DNA
<213> ORGANISM: Artificial Sequence
<220> FEATURE:
<223> OTHER INFORMATION: Primer

<400> SEQUENCE: 442
aatgtacagt attgcgtttt gaatttatag ctcttttcat ctgctttggt atcatca        57

<210> SEQ ID NO 443
<211> LENGTH: 56
<212> TYPE: DNA
<213> ORGANISM: Artificial Sequence
<220> FEATURE:
<223> OTHER INFORMATION: Primer

<400> SEQUENCE: 443
aatgtacagt attgcgtttt ggcctctaat ctgatataca gccttagaaa gtcaca         56

<210> SEQ ID NO 444
<211> LENGTH: 47
<212> TYPE: DNA
<213> ORGANISM: Artificial Sequence
<220> FEATURE:

<223> OTHER INFORMATION: Primer

<400> SEQUENCE: 444
aatgtacagt attgcgttttt gtgtgccatt gtcctggagc aacaatt        47

<210> SEQ ID NO 445
<211> LENGTH: 57
<212> TYPE: DNA
<213> ORGANISM: Artificial Sequence
<220> FEATURE:
<223> OTHER INFORMATION: Primer

<400> SEQUENCE: 445
aatgtacagt attgcgtttt gagtgtactg ctcgtttttct taatttgaaa agtgagt        57

<210> SEQ ID NO 446
<211> LENGTH: 57
<212> TYPE: DNA
<213> ORGANISM: Artificial Sequence
<220> FEATURE:
<223> OTHER INFORMATION: Primer

<400> SEQUENCE: 446
aatgtacagt attgcgtttt gacccatgaa ctaatactta ttttgagatt ggtccat        57

<210> SEQ ID NO 447
<211> LENGTH: 55
<212> TYPE: DNA
<213> ORGANISM: Artificial Sequence
<220> FEATURE:
<223> OTHER INFORMATION: Primer

<400> SEQUENCE: 447
aatgtacagt attgcgtttt gcatggtgca acaaaagtaa gaatccaaca gtttt        55

<210> SEQ ID NO 448
<211> LENGTH: 57
<212> TYPE: DNA
<213> ORGANISM: Artificial Sequence
<220> FEATURE:
<223> OTHER INFORMATION: Primer

<400> SEQUENCE: 448
aatgtacagt attgcgtttt gttgaaatgt taagtaagct tgaaataccg atagcat        57

<210> SEQ ID NO 449
<211> LENGTH: 51
<212> TYPE: DNA
<213> ORGANISM: Artificial Sequence
<220> FEATURE:
<223> OTHER INFORMATION: Primer

<400> SEQUENCE: 449
aatgtacagt attgcgtttt ggggaggaag aaaatgaagc acgaggaaaa c        51

<210> SEQ ID NO 450
<211> LENGTH: 57
<212> TYPE: DNA
<213> ORGANISM: Artificial Sequence
<220> FEATURE:
<223> OTHER INFORMATION: Primer

<400> SEQUENCE: 450
aatgtacagt attgcgtttt gatttgggat gtactctaaa tttaaagcag caaatca        57

```
<210> SEQ ID NO 451
<211> LENGTH: 57
<212> TYPE: DNA
<213> ORGANISM: Artificial Sequence
<220> FEATURE:
<223> OTHER INFORMATION: Primer

<400> SEQUENCE: 451
aatgtacagt attgcgtttt gtcaagagca gaatttggag actttgatat taaaact       57

<210> SEQ ID NO 452
<211> LENGTH: 57
<212> TYPE: DNA
<213> ORGANISM: Artificial Sequence
<220> FEATURE:
<223> OTHER INFORMATION: Primer

<400> SEQUENCE: 452
aatgtacagt attgcgtttt gcggttacta acatgtttag ggaaatagac aactgtt       57

<210> SEQ ID NO 453
<211> LENGTH: 57
<212> TYPE: DNA
<213> ORGANISM: Artificial Sequence
<220> FEATURE:
<223> OTHER INFORMATION: Primer

<400> SEQUENCE: 453
aatgtacagt attgcgtttt gcctgacaac agatcccata taattaactt tcatacc       57

<210> SEQ ID NO 454
<211> LENGTH: 55
<212> TYPE: DNA
<213> ORGANISM: Artificial Sequence
<220> FEATURE:
<223> OTHER INFORMATION: Primer

<400> SEQUENCE: 454
aatgtacagt attgcgtttt gagatgaaga agatgaggaa cgagagagta aaagc         55
```